United States Patent
Roberts et al.

(10) Patent No.: US 10,407,665 B2
(45) Date of Patent: Sep. 10, 2019

(54) METHODS FOR GENERATION OF PLURIPOTENT AND MULTIPOTENT CELLS

(71) Applicant: THE UNITED STATES OF AMERICA, AS REPRESENTED BY THE SECRETARY, DEPARTMENT OF HEALTH & HUMAN SERVICES, Bethesda, MD (US)

(72) Inventors: David D. Roberts, Bethesda, MD (US); Sukhbir Kaur, Bethesda, MD (US); Jeffrey S. Isenberg, Mt. Lebanon, PA (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

(21) Appl. No.: 14/390,134

(22) PCT Filed: Apr. 9, 2013

(86) PCT No.: PCT/US2013/035838
§ 371 (c)(1),
(2) Date: Oct. 2, 2014

(87) PCT Pub. No.: WO2013/155109
PCT Pub. Date: Oct. 17, 2013

(65) Prior Publication Data
US 2015/0111768 A1    Apr. 23, 2015

Related U.S. Application Data

(60) Provisional application No. 61/621,994, filed on Apr. 9, 2012, provisional application No. 61/735,701, filed on Dec. 11, 2012.

(51) Int. Cl.
*C12N 5/074* (2010.01)
*C12N 5/079* (2010.01)
*C12N 5/0789* (2010.01)

(52) U.S. Cl.
CPC ......... *C12N 5/0696* (2013.01); *C12N 5/0618* (2013.01); *C12N 5/0647* (2013.01); *C12N 2501/599* (2013.01)

(58) Field of Classification Search
CPC .. C12N 5/0696; C12N 5/0618; C12N 5/0647; C12N 2501/599
See application file for complete search history.

(56) References Cited

FOREIGN PATENT DOCUMENTS

WO    WO 2010/070047 A1    6/2010
WO    WO 2011/041062 A1    4/2011

OTHER PUBLICATIONS

Thomson et al. PNAS, 92:7844-7848, Aug. 1995.*
Jaenisch et al., Cell, 132: 567-582, 2008.*
Sullivan et al. Reproductive BioMed. Online, 16(1): 41-50, Nov. 2008.*
Hochedlinger et al. Cell, 121: 465-477, May 6, 2005.*
Pera, J. of Cell Science, 113: 5-10, 2000.*
Eiges, FEBS Letters, 529: 135-141, 2002.*
Gerecht-Nir, Developmental Dynamics, 232: 487-497 (2005).*
Kaur et al., Journal of Biological Chemistry, 285(50): 38923-38932, 2010.*
Gonzalez et al., Nature Reviews, 12: 231-242, 2011.*
Daniel et al., Trends in Cell Biology, 26(3): 202-214, 2016.*
Cyranoski, Nature, 516: 162-164, 2014.*
Kelaini et al. Stem Cells and Cloning: Advances and Applications, 7: 19-29, 2014.*
Bras, M., et al., "Drp1 mediates caspase-independent type III cell death in normal and leukemic cells," Mol Cell Biol. Oct. 2007;27(20):7073-88.
Maxhimer, J.B., et al., "Radioprotection in normal tissue and delayed tumor growth by blockade of CD47 signaling," Sci Transl Med. Oct. 21, 2009;1(3):3ra7.
Official Action for Canada Patent Application No. 2,869,913, dated Oct. 1, 2015 4 pages.
Official Action for European Patent Application No. 13718439.6, dated Dec. 23, 2015 5 pages.
International Search Report prepared by the European Patent Office dated Jun. 25, 2013, for International Application No. PCT/US2013/035838.
Jaiswal Siddhartha et al: "CD47 Is Upregulated on Circulating Hematopoietic Stem Cells and Leukemia Cells to Avoid Phagocytosis", Cell, Cell Press, US, vol. 138, No. 2, Jul. 1, 2009 (Jul. 1, 2009), pp. 271-285, XP009160236.
David D. Roberts et al.: "The matricellular protein thrombospondin-1 globally regulates cardiovascular function and responses to stress via CD47", Matrix Biology, Elsevier, NL, vol. 31, No. 3, Dec. 10, 2011 (Dec. 10, 2011), pp. 162-169, XP028403333.
Mark P. Chao et al: "The CD47-SIRP[alpha] pathway in cancer immune evasion and potential therapeutic implications", Current Opinion in Immunology, vol. 24, No. 2, Apr. 1, 2012 (Apr. 1, 2012), pp. 225-232, XP055029985.
Isenberg J S et al: "Treatment of liver ischemia-reperfusion injury by limiting thrombospondin-1/CD47 signaling", Surgery, C.V. Mosby Co., St. Louis, US, vol. 144, No. 5, Nov. 1, 2008 (Nov. 1, 2008).
Official Action for European Patent Application No. 13718439.6, dated Nov. 29, 2016 4 pages.
Official Action for Australia Patent Application No. 2013246040, dated Nov. 21, 2017 4 pages.

(Continued)

*Primary Examiner* — Thaian N Ton

(74) *Attorney, Agent, or Firm* — Sheridan Ross P.C.

(57) ABSTRACT

This disclosure relates to methods of producing induced pluripotent (iPS), multipotent, and/or lineage-committed stem cells from differentiated cells, maintaining iPS, multipotent, and/or lineage-committed cells in culture, and re-differentiating the iPS and multipotent stem cells into any desired lineage-committed cell type.

14 Claims, 31 Drawing Sheets

Specification includes a Sequence Listing.

(56) References Cited

OTHER PUBLICATIONS

Official Action for Canada Patent Application No. 2,869,913, dated Jan. 2, 2018 3 pages.
Intention to Grant for European Patent Application No. 13718439.6, dated Dec. 8, 2017 111 pages.

* cited by examiner

FIG. 2A
Mouse lung endothelial cell mRNA levels (ΔCt)
|  | c-Myc | P16 INK4A | TRP53 | Rb |
|---|---|---|---|---|
| WT | 31.94 | 34.3 | 37.8 | 33.1 |
| CD47-/- | 25.4 | 32.4 | 37.36 | 31.6 |
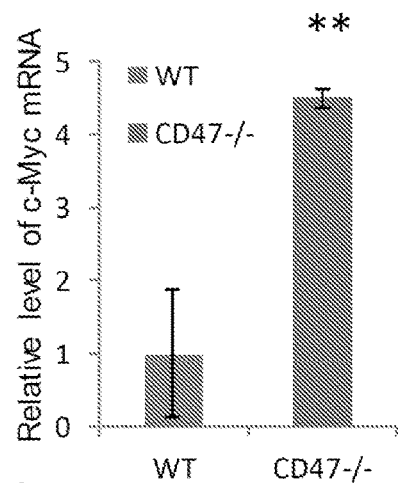
FIG. 2B
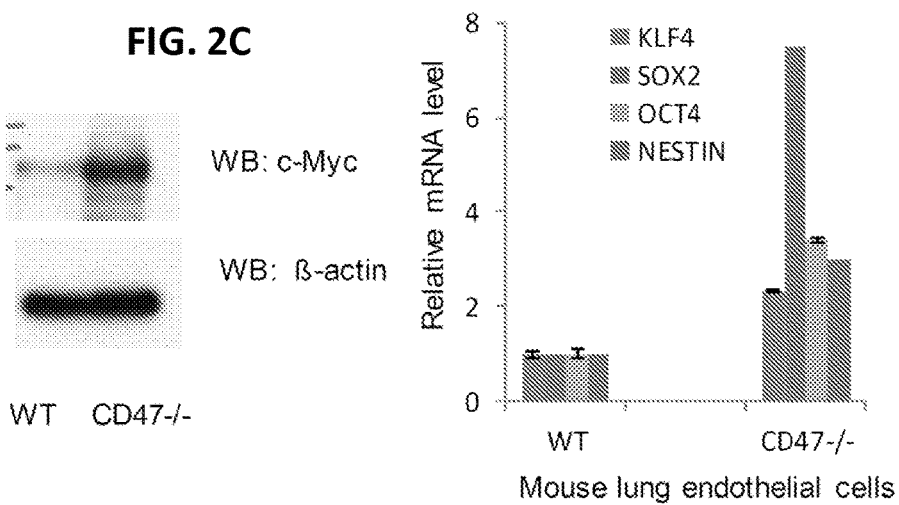
FIG. 2C
FIG. 2D

FIG. 3C
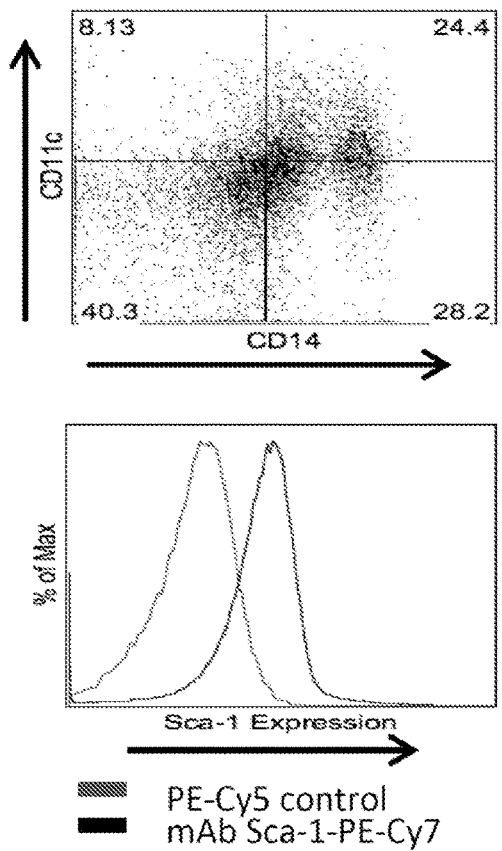
FIG. 3D
FIG. 3F
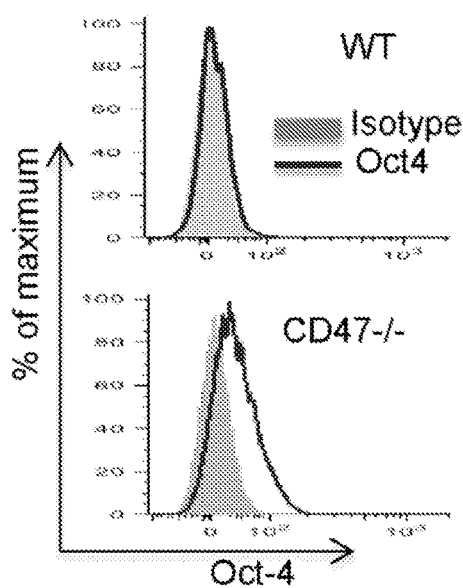
FIG. 3E
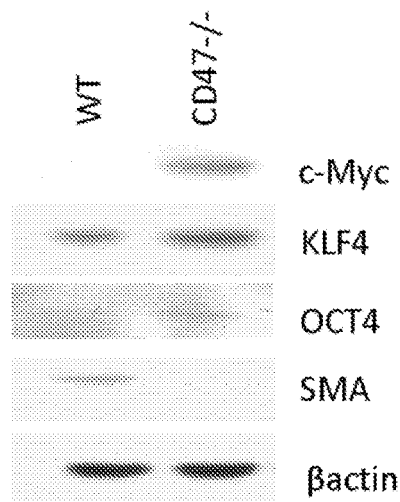
FIG. 3G
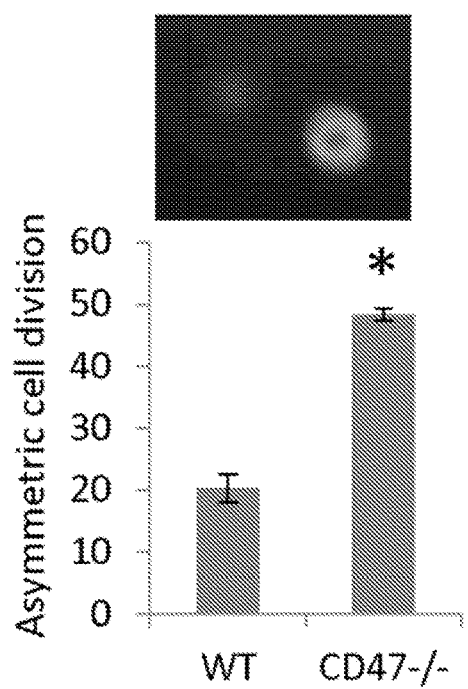

EB-like clusters

DAPI
phalloidin
BrdU

CD47-/- EB-like clusters      V6.5 ES cells

FIG. 4A
FIG. 4B
FIG. 4C
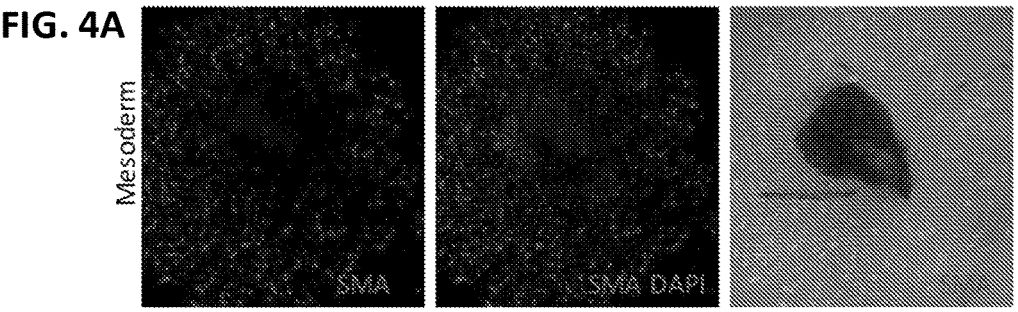
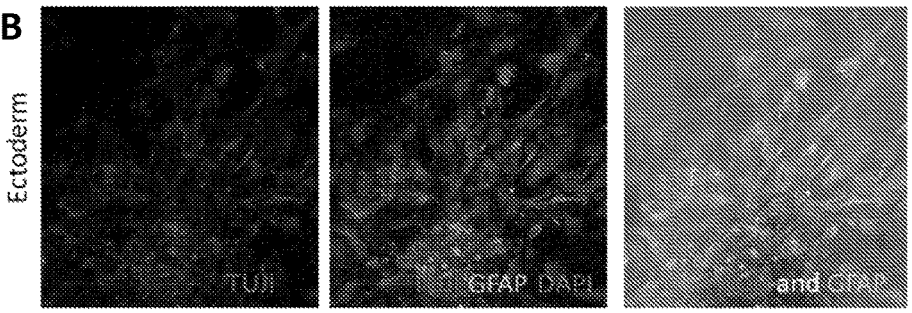
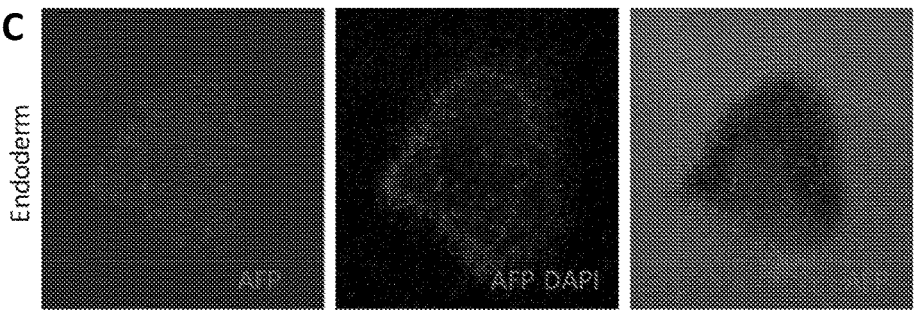
FIG. 4D  FIG. 4E  FIG. 4F
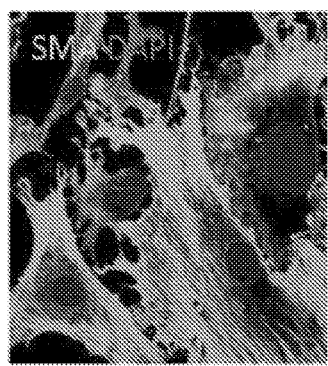
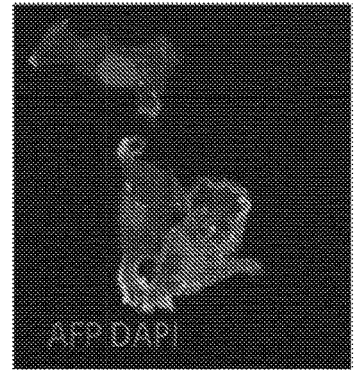

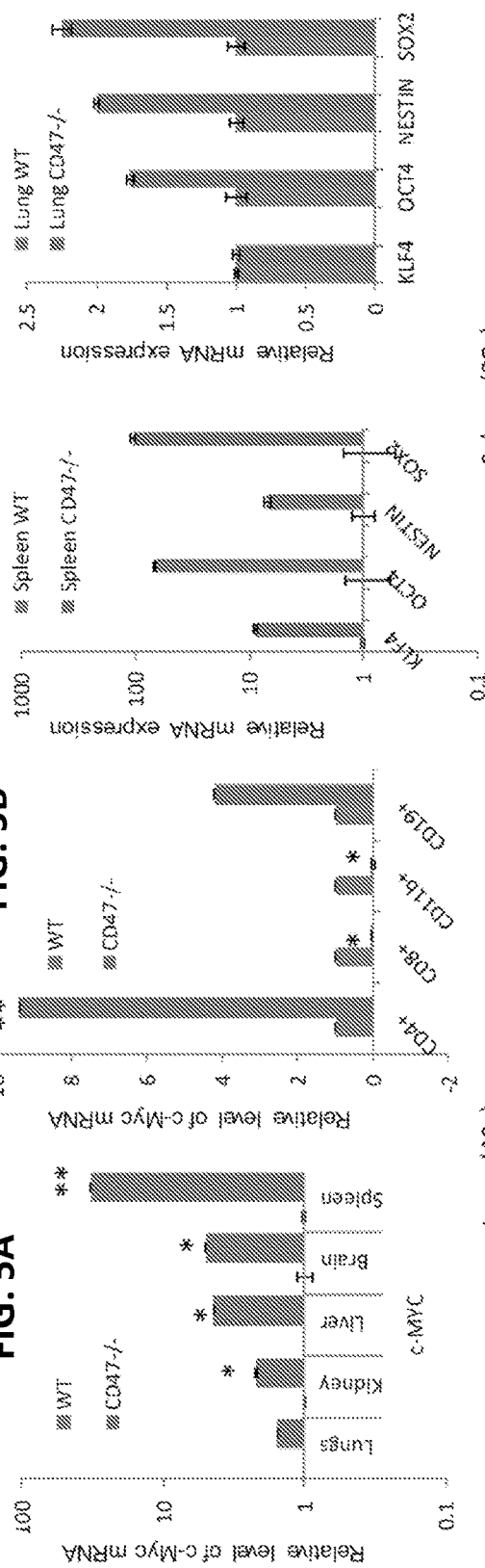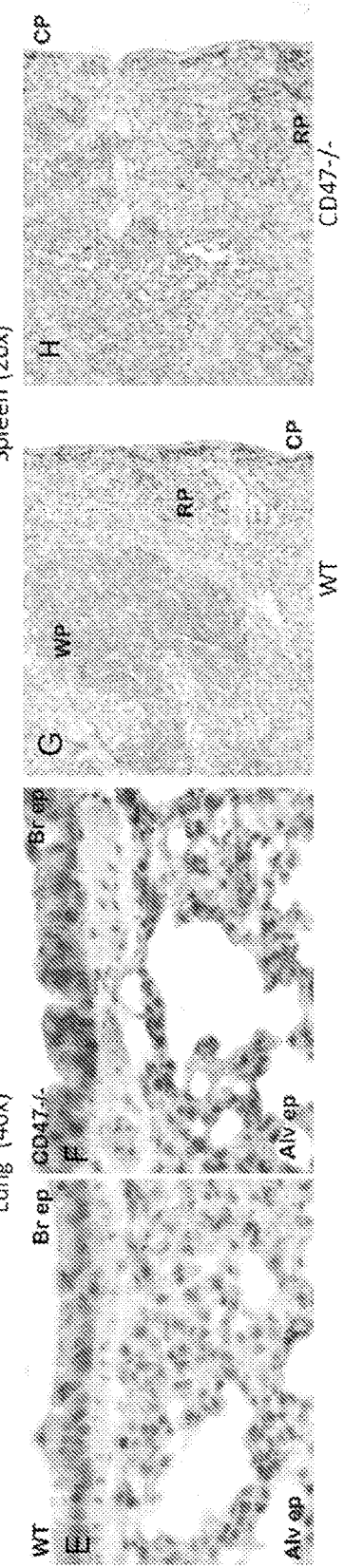

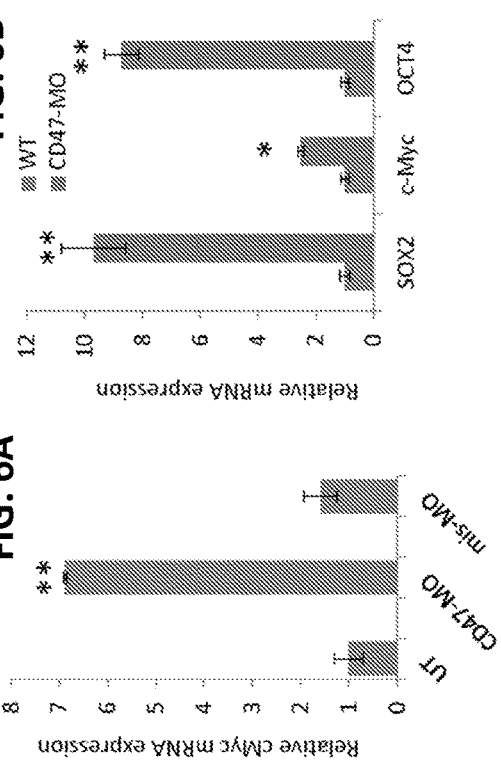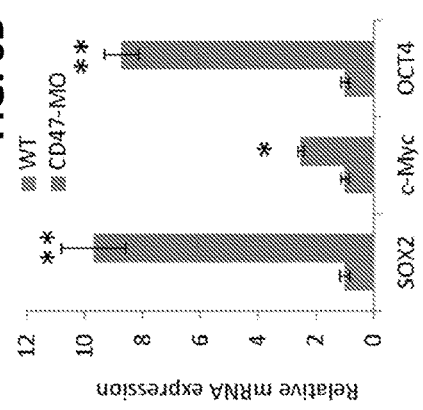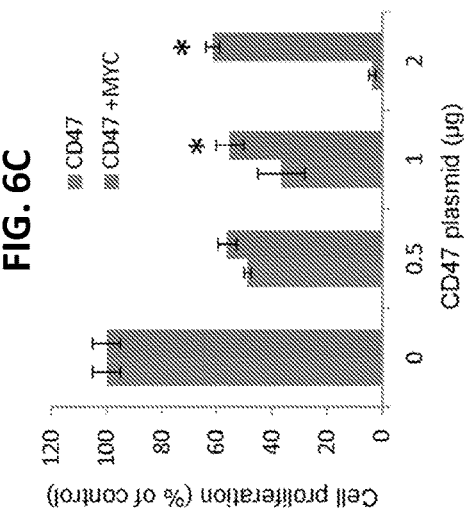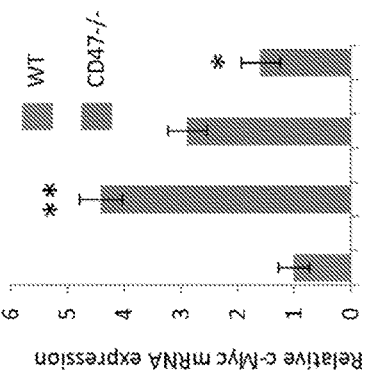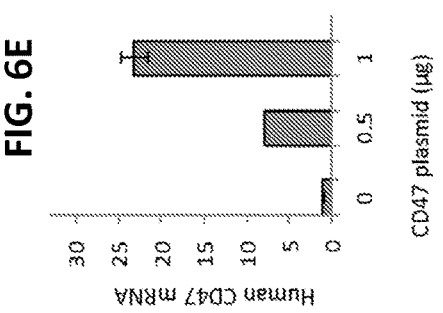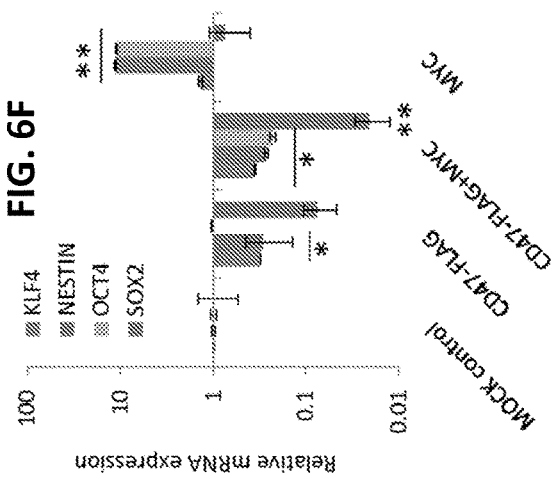

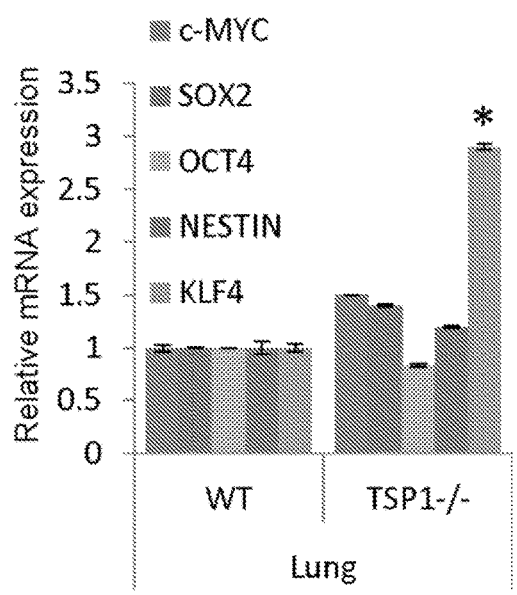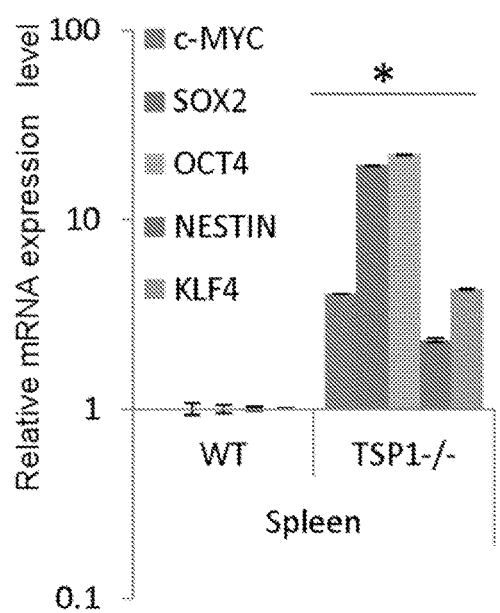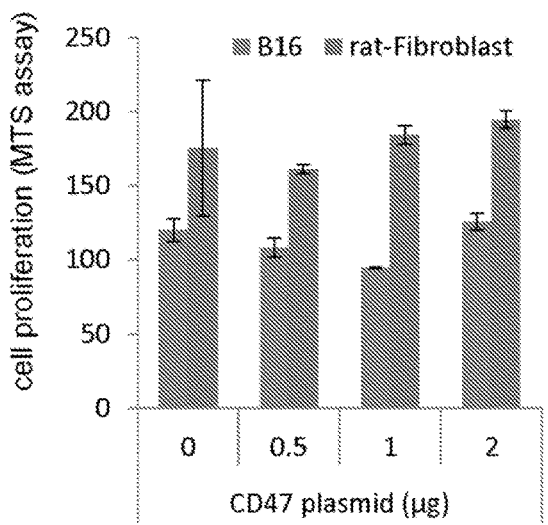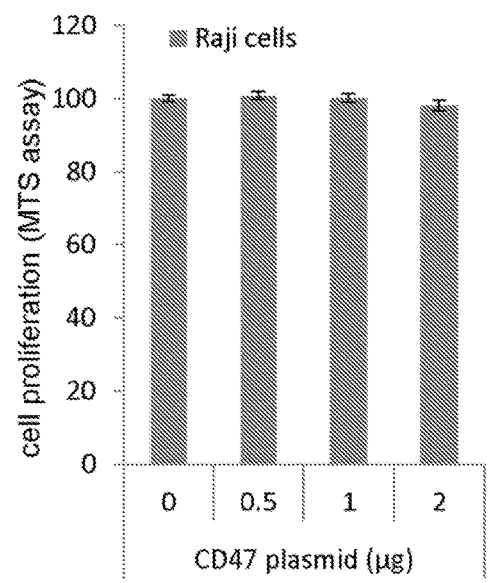

FIG. 9A
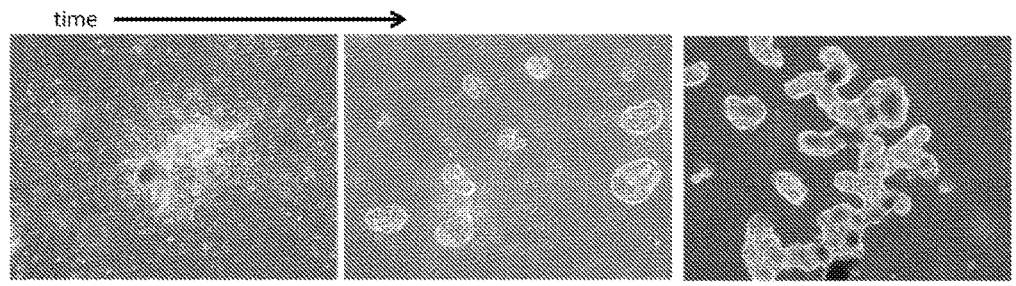
FIG. 9B
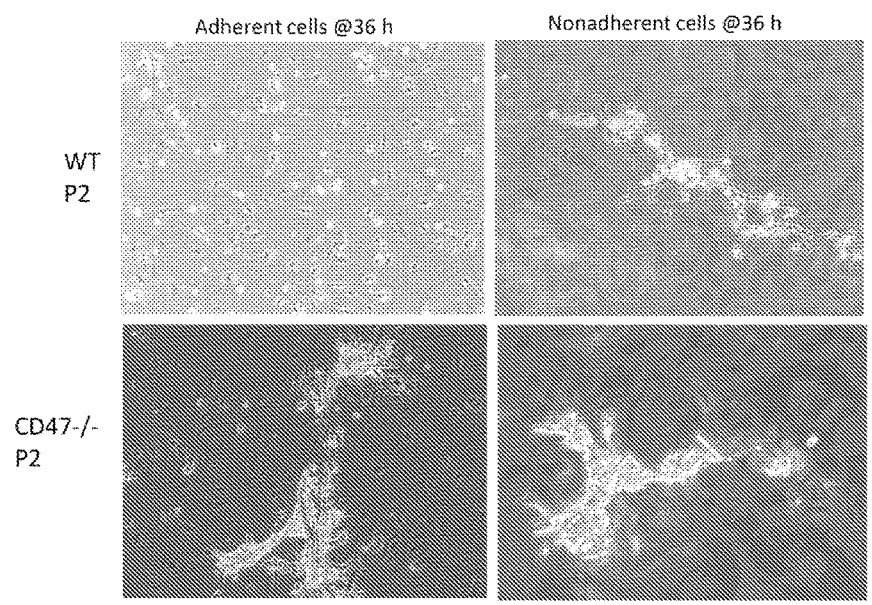
| FIG. 10A | FIG. 10B | FIG. 10C | FIG. 10D |
|---|---|---|---|
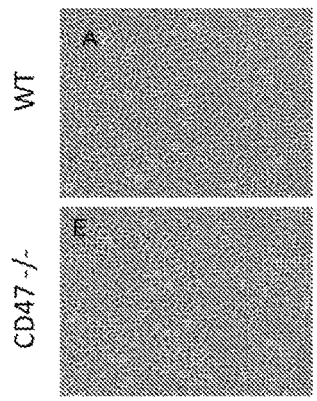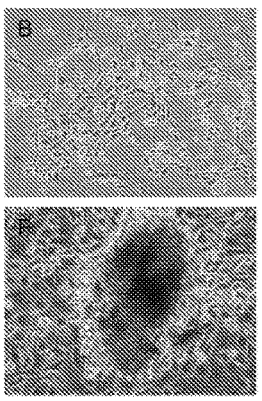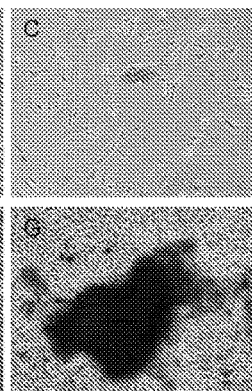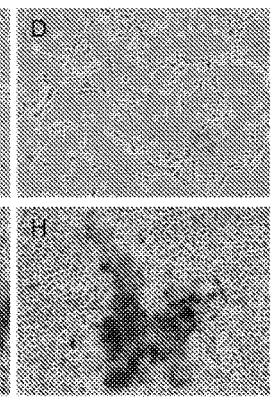
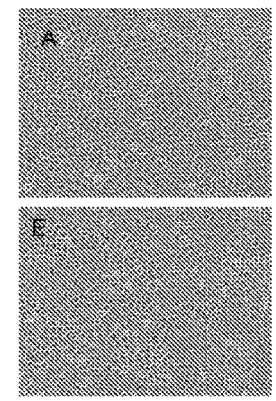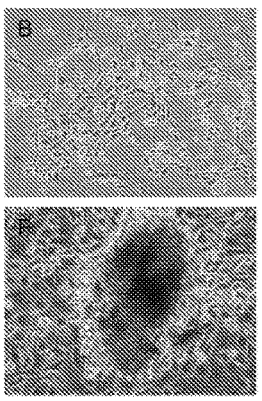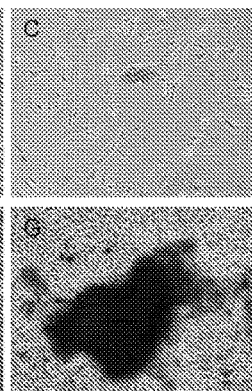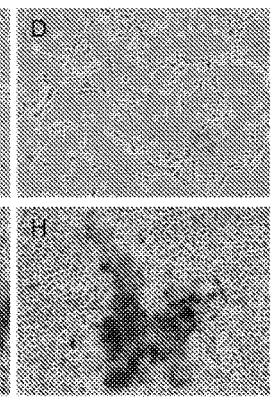
| FIG. 10E | FIG. 10F | FIG. 10G | FIG. 10H |
|---|---|---|---|
Hepatocyte medium without serum

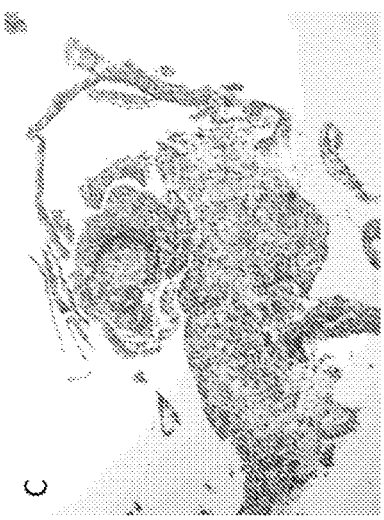
FIG. 11A  FIG. 11B  FIG. 11C
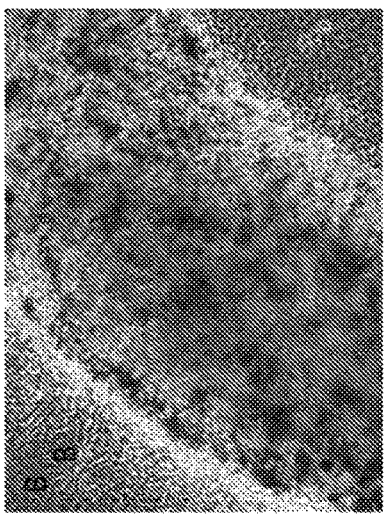
FIG. 11D  FIG. 11E  FIG. 11F
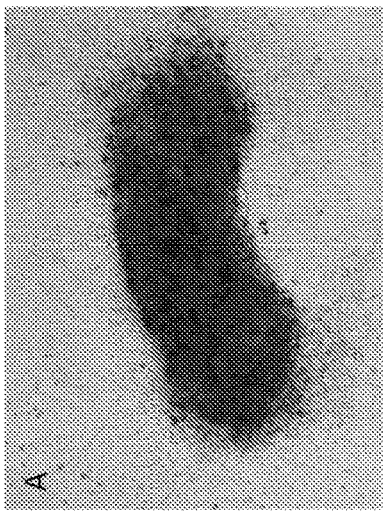
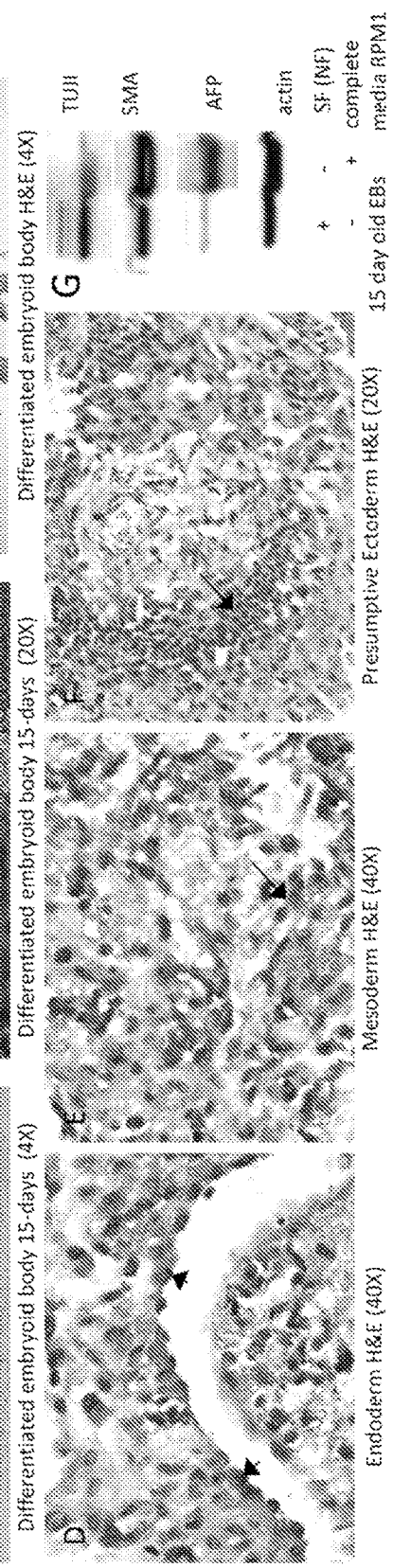
FIG. 11G FIG. 13A
FIG. 13B
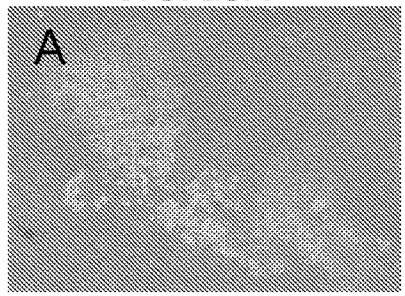
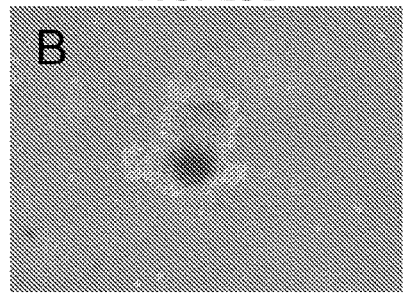
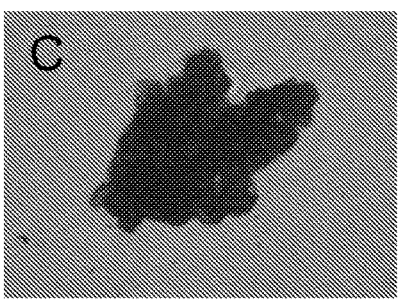
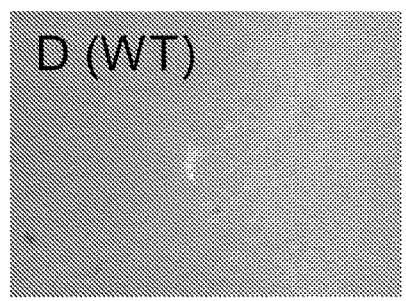
FIG. 13C
FIG. 13D
FIG. 13E
FIG. 13G
FIG. 13J
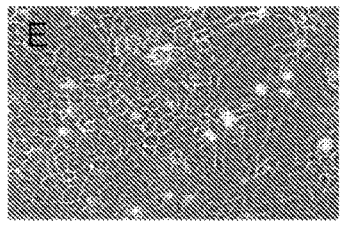
Endothelial Cells + EBM2 Medium
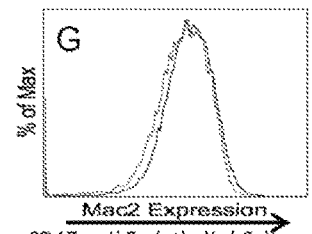
CD47 null Endothelial Cells + EBM2 Medium
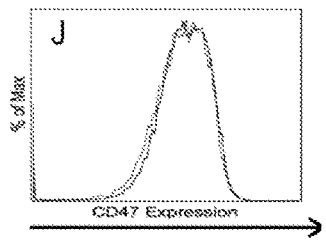
▒▒▒ FITC control
━━━ mAb maip301-FITC
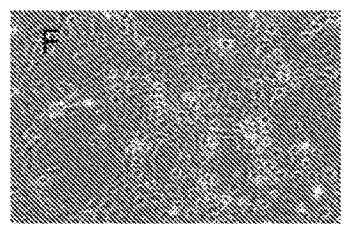
CD47 null Endothelial Cells + L929 Conditioned Medium
FIG. 13F
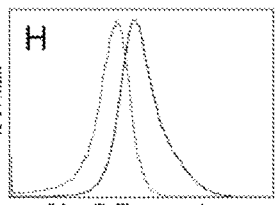
CD47 null Endothelial Cells + L929 Conditioned Medium
FIG. 13H
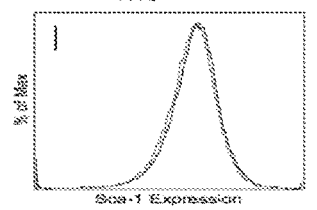
▒▒▒ PE-Cy5 control
━━━ mAb Sca-1-PE-Cy7
FIG. 13I supplementary for Figure 6 panel D-E

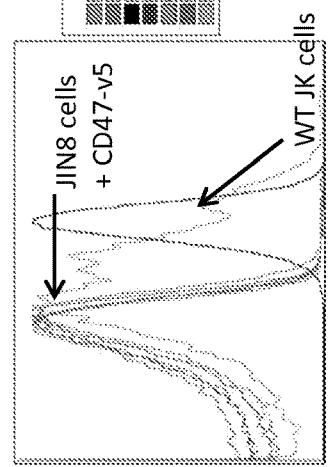
FIG. 14D
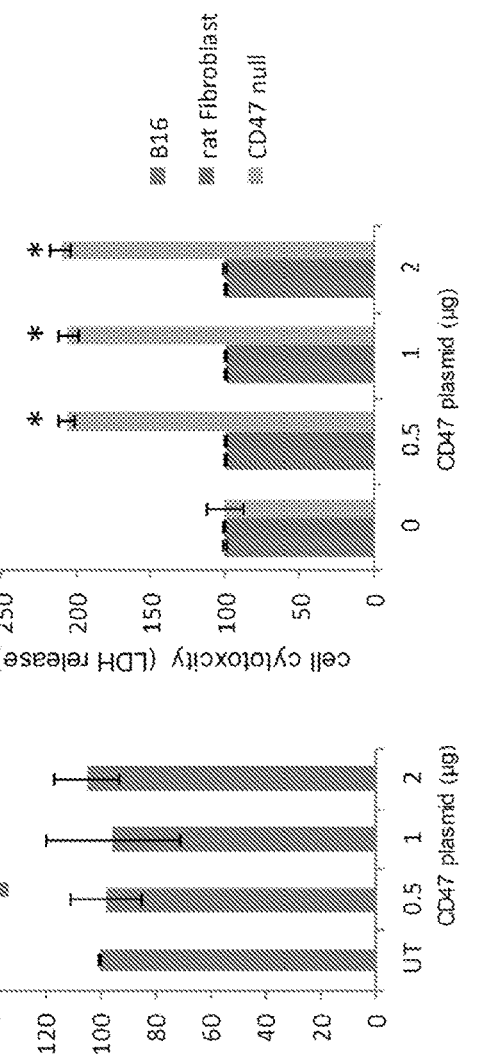
FIG. 14E
FIG. 14F
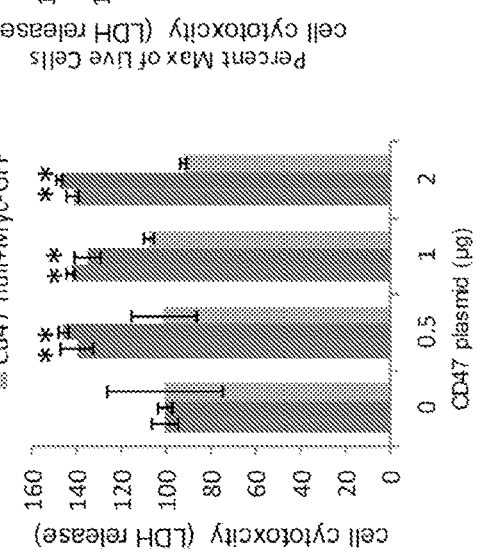
FIG. 14G
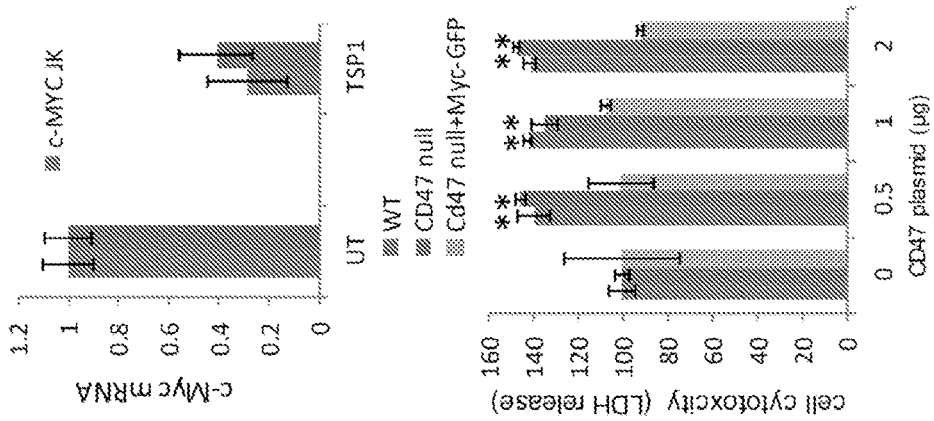
FIG. 14H

METHODS FOR GENERATION OF PLURIPOTENT AND MULTIPOTENT CELLS

CROSS REFERENCE TO RELATED APPLICATIONS

This application is a national stage application under 35 U.S.C. 371 and claims the benefit of PCT Application No. PCT/US2013/035838 having an international filing date of Apr. 9, 2013, which designated the United States, which PCT application claimed the benefit of U.S. Provisional Application No. 61/621,994, filed Apr. 9, 2012, and U.S. Provisional Application No. 61/735,701, filed Dec. 11, 2012, the disclosure of each of which are incorporated herein by reference in their entirety.

FIELD

This disclosure relates to methods of producing induced pluripotent stem (iPS), multipotent, and/or lineage-committed cells from differentiated cells, maintaining iPS, multipotent, and/or lineage-committed cells in culture, and re-differentiating the iPS and/or multipotent cells into any desired lineage-committed cell type.

BACKGROUND

A primary goal of regenerative medicine is replacement of diseased or damaged cells and tissues. Abundant and safe sources of multipotent or pluripotent stem cells are necessary to further this goal. Embryonic stem (ES) cell lines are available for possible regenerative medicine applications, but challenges remain for their use, including possible immune rejection by a receiving patient (reviewed in Yabut et al., *Aging* 3(5):494-508, 2011). In recent years, induced pluripotence in differentiated cells has been explored as an alternative to ES cells (reviewed in Ebben et al., *World Neurosurg.* 76(3-4):270-275, 2011). It was discovered that expression of just four stem cell transcription factor genes (c-Myc, Sox2, Klf4, and Oct4) can de-differentiate and induce pluripotence in cells grown under particular culture conditions (e.g. in the absence of serum) (WO 2012/012708; and Takahashi et al., *Cell.* 126: 663-676, 2006). Among other benefits, such induced pluripotent stem (iPS) cells might be generated from a potential patient's own cells, thereby minimizing adverse immunoreactivity upon introduction of pluripotent or newly-differentiated cells to the patient.

iPS cells are currently produced by transforming cells with viral or other constitutive expression vectors encoding the four stem cell transcription factor genes. Among these, the over-expression of c-Myc is of particular concern because sustained Myc expression can result in malignant transformation. Furthermore, any of these vectors can permanently integrate into the cellular genome at sites that activate oncogenes or disrupt tumor suppressor genes. Current efforts in the stem cell field to produce iPS cells without the risk of malignant transformation involve identification of small molecules to induce individual stem cell genes (c-Myc, Sox2, Klf4, and Oct 4), with the goal of designing a mixture of several small molecules that together can produce iPS cells. But to date, no single agent has been identified that can be used to produce iPS cells. Thus, a continuing need exists to identify agents that can produce iPS cells, without the need for plasmid- or retroviral-mediated expression of individual stem cell-inducing genes.

SUMMARY

Described herein are the surprising observations that blockade of signaling by the cellular receptor CD47 results in significantly increased cellular lifespan and expansion of lineage-committed or differentiated cells in culture, and when such cells are grown in appropriate media (such as serum-free media), production of multipotent or iPS cells. These cellular phenotypes are associated with increased expression of the transcription and cell proliferation factor c-Myc, and increased expression of the hallmark stem cell-inducing transcription factors Sox2, Klf4, and Oct4. In appropriate culture media, the multipotent or iPS cells can then be differentiated into desired cell types, which can be expanded and maintained in culture by transient, intermittent, or continued CD47 blockade.

Based upon these observations, methods are enabled and described herein for generating and/or expanding lineage-committed stem cells, multipotent stem cells, and/or iPS cells from lineage-committed or differentiated cells by CD47 blockade. CD47 signaling blockade can be achieved in any way or with any agent that inhibits CD47 expression on the cell surface, or that blocks CD47 intracellular signaling, such as by blocking the binding of CD47 ligands, including blocking binding of the matricellular protein thrombospondin-1 (TSP1). In particular embodiments of the disclosed methods, CD47 blockade can be achieved by contacting cells with one or more TSP1-derived peptides, anti-CD47 or anti-TSP1 antibodies, anti-CD47 or anti-TSP1 antisense oligonucleotides or morpholinos or other stabilized nucleic acid molecules. These and other methods of blocking CD47 signaling are described in detail in U.S. Patent Publications No. US 2010/0092467 and US 2011/0135641, which are hereby incorporated by reference in their entirety. In other embodiments, CD47 signaling blockade can be achieved by contacting CD47-expressing cells with a chemical agent (such as a small molecule agent) that binds to CD47 or TSP1 and blocks or reduces CD47-signaling.

In particular embodiments, the described methods include obtaining primary cells (such as lineage-committed (differentiated) cells) from an animal or subject and contacting the obtained cells with an agent that can block CD47 signaling. Multipotent or pluripotent stem cells are produced from the CD47-blocked cells when the blocked cells are cultured in appropriate culture media, which in particular embodiments includes serum-free medium.

Also described herein are methods of maintaining stem cells in a de-differentiated state capable of self-renewing proliferation by continued exposure of the cells to an agent that blocks CD47 signaling. The de-differentiated state is maintained as long as the cells are cultured in appropriate media and exposed to a CD47 blocking agent. In some embodiments transient exposure to a CD47 blocking agent is sufficient to induce this de-differentiated state resulting in cells capable of self-renewing proliferation.

Further described herein are methods of producing a desired differentiated cell type from a previously lineage-committed cell type. Desired cell types can be produced by generating multipotent or iPS cells using a CD47 blocking agent as described above, and then removing the CD47 blocking agent from the iPS cells, while also culturing the iPS cells in medium containing appropriate differentiating factors known to those of ordinary skill in the art. In some examples, the newly-differentiated cells can be immortalized for storage by re-exposure to a CD47 blocking agent.

Such cells will maintain their differentiated state in the appropriate media, such as serum-containing media.

Additionally described herein are iPS cells produced by the described methods, and lineage-committed cells differentiated from the produced iPS cells.

Also described herein are methods to employ CD47 blockers to continuously expand lineage-committed stem cells or iPS cells from a small amount of donor tissue or cell aspirate that can later be re-administered to that donor.

One of ordinary skill in the art will appreciate that the ability to generate and maintain a ready supply of multipotent or iPS cells from which lineage-committed cells can be produced using a single defined agent will have significant benefits in the field of regenerative medicine. This approach will also greatly expand the potential applications of autologous stem cell therapy, including applications where genetic defects are corrected ex vivo before re-administering the expanded cells to an individual suffering from an inherited or acquired genetic defect.

The foregoing and other features will become more apparent from the following detailed description, which proceeds with reference to the accompanying figures.

BRIEF DESCRIPTION OF THE DRAWINGS

FIG. 1A is a graph of a 3-(4,5-dimethylthiazol-2-yl)-5-(3-carboxymethoxyphenyl)-2-(4-sulfophenyl)-2H-tetrazolium (MTS) assay for cell survival and growth over 72 hours expressed as % of day 0 values at the indicated plating densities of first passage WT and CD47 null cells. FIG. 1B is a graph of a 5-bromo-2'-deoxyuridine (BrdU) assay for DNA synthesis. FIG. 1C is a graph of percentage of senescence-associated β-galactosidase (β-gal) expression at passage 3 ($*p<0.05$, $**p<0.01$).

FIGS. 2A-2F show CD47 signaling inhibits c-Myc and additional stem cell transcription factor expression in vitro and in vivo. FIG. 2A is a chart showing expression of genes associated with cell immortalization in WT and CD47 null cells. FIG. 2B is a graph of c-Myc mRNA levels in lung endothelial cells of CD47 null and WT mice. FIG. 2C is a digital image of a Western blot showing c-Myc levels in WT and CD47 null mouse lung endothelial cells. CD47 limits c-Myc protein levels. FIG. 2D is a graph showing mRNA expression levels of stem cell transcription factors in WT and CD47 null lung endothelial cells. From left to right, bars indicate Klf4, Sox2, Oct4, and Nestin mRNA levels for WT and CD47 null cells. FIG. 2E is a pair of digital images showing detection of c-Myc expression by immunofluorescence in WT and CD47-null endothelial cells. FIG. 2F is a pair of panels showing flow cytometric analysis of c-Myc expression in WT and CD47-null endothelial cells ($*p<0.05$, $**p<0.01$).

FIGS. 3A-3K show stem cell and differentiation marker expression in CD47-null endothelial cells and embryoid bodies induced by serum-free medium. FIG. 3A is a series of digital images showing CD47-null endothelial cells stained using the indicated antibodies and DAPI. FIG. 3B is a series of digital images showing typical appearance of embryoid body (EB)-like clusters photographed under phase contrast or stained using the indicated antibodies and DAPI. FIG. 3C is a plot showing analysis of CD14 and CD11c in CD47-null endothelial cells using flow cytometry. FIG. 3D is a plot showing Sca-1 expression in CD47-null endothelial cells. FIG. 3E is a series of digital images of Western blots for protein expression of stem cell transcription factors from cultured WT or CD47 null endothelial cells (in EGM2 medium). FIG. 3F is a pair of panels showing protein expression of Oct4 by flow cytometry in cultured WT or CD47-null endothelial cells in EGM2 medium. FIG. 3G is a pair of panels showing asymmetric cell division in second passage WT and CD47-null endothelial cells equilibrium labeled with bromodeoxyuridine (BrdU) and chased for one cell division. Asymmetric division was scored by counting BrdU$^+$/DAPI$^+$ nuclei adjacent to BrdU$^-$/DAPI$^+$ nuclei. FIG. 3H shows flow cytometric analysis of c-Myc expression in CD47-null cells dissociated from EB-like clusters. FIG. 3I shows detection of asymmetric cell division in cells from CD47-null EB-like clusters equilibrium labeled with BrdU, and then chased for two cell divisions without BrdU. Top left, DAPI; middle left, phalloidin; bottom left, BrdU; bottom right combined image. FIG. 3J is a pair of digital images showing morphology of CD47-null EB-like clusters (left) and V6.5 ES cells (right) growing in ES medium with LIF. The V6.5 culture also contains an MEF feeder layer. FIG. 3K is a series of digital images showing CD47-null EB-like clusters (center) and V6.5 ES cells (left) cultured as in FIG. 3J and CD47-null endothelial cells in endothelial growth medium (right) stained using the indicated antibodies and DAPI.

FIGS. 4A-F show differentiation of CD47-null EB-like clusters. FIG. 4A is a series of digital images of EB-like clusters cultured in RPMI complete medium for 6 days and then transferred to lineage-specific media for 36 hours and stained with smooth muscle actin antibody to detect mesodermal cells. FIG. 4B is a series of digital images of differentiated EB-like clusters stained with the ectoderm neural markers glial fibrillary acidic protein (GFAP) and neuron-specific beta III tubulin (TUJI). FIG. 4C is a series of digital images of differentiated EB-like clusters stained with anti-α-fetoprotein (AFP) to detect ectodermal cells. In all panels DAPI was used to visualize nuclei. FIGS. 4D-F show expansion of a single clone isolated from a CD47-null EB-like cluster expanded in serum-free medium and then differentiated in the respective lineage-specific medium for 7 days and stained for SMA (FIG. 4D), TUJI (FIG. 4E), or AFP (FIG. 4F).

FIGS. 5A-H shows that CD47 regulates stem cell transcription factors in vivo. FIG. 5A is a graph showing c-Myc mRNA from lung, kidney, liver, brain and spleen of WT and CD47-null mice. FIG. 5B is a graph showing c-Myc mRNA levels in purified splenic cell populations from WT (left bars) and CD47 null (right bars) mice. FIG. 5C is a graph showing mRNA expression levels of the indicated genes in spleen from WT (left bars) and CD47-null (right bars) mice. FIG. 5D is a graph showing mRNA expression levels of the indicated genes in lung from WT (left bars) and CD47-null (right bars) mice. (For panels A-D, $*p<0.05$, $**p<0.01$). FIGS. 5E-H are a series of digital images showing increased frequency of Sox2 expressing cells in tissues from CD47-null mice. The alveolar (Alv) regions of lung tissues from WT (FIG. 5E) generally lack Sox2-positive cells, whereas CD47-null lung shows more positive cells (FIG. 5F). In contrast, similar uniform Sox2 staining was observed in bronchiolar epithelium (BrEp) from WT and null mice (FIGS. 5E and F), consistent with its previously reported expression in Clara cells (Tompkins et al., *PLoS One* 4:e8248, 2009). Paraffin embedded sections of representative spleen tissues from WT (FIG. 5G) and CD47-/- (FIG. 5H) mice were stained with a specific antibody to Sox2. Sections were examined under light microscopy showing subcapsular (CP), red pulp (RP) and white pulp (WP) staining.

FIGS. 6A-6F show that CD47 expression regulates c-Myc and stem cell transcription factor expression. FIG. 6A is a graph showing morpholino knockdown of CD47 (CD47-MO) in WT lung endothelial cells increases c-Myc mRNA expression, but a control mismatched morpholino (mis-MO) does not. FIG. 6B is a graph showing in vivo morpholino knockdown of CD47 elevates c-Myc, Oct4, and Sox2 mRNA at 48 hours in mouse spleen (left bars, WT; right bars, CD47-MO). FIG. 6C is a graph showing CD47 re-expression in CD47-null murine endothelial cells suppresses cell growth (left bars) unless c-Myc expression is sustained (CD47+MYC, right bars). FIG. 6D is a graph showing CD47 re-expression in CD47 null endothelial cells alters c-Myc expression. FIG. 6E is a graph showing expression levels of transfected human CD47. FIG. 6F is a graph showing re-expression of CD47 with an internal FLAG tag (CD47-FLAG) and c-Myc alters mRNA expression of stem cell transcription factors ($*p<0.05$, $**p<0.01$). For each condition, from left to right, bars indicate Klf4, Nestin, Oct4, and Sox2.

FIGS. 7A-7I show regulation of c-Myc and stem cell transcription factors by CD47 ligation. FIG. 7A is a graph showing c-Myc mRNA in Jurkat (JK) and CD47-deficient JinB8 T cells (JIN). FIG. 7B is a graph showing time-dependence for regulation of c-Myc mRNA expression by the CD47 ligand thrombospondin-1 (TSP1). Jurkat cells were treated with 2.2 nM thrombospondin-1 for the indicated times before isolating RNA and assessing c-Myc mRNA by real time PCR normalized to (32-microglobulin mRNA and expressed as ratio to normalized c-Myc levels in control cells at the corresponding time points. FIG. 7C is a graph showing TSP1 effects on c-Myc mRNA in WT Jurkat (diamonds) and CD47-deficient T lymphoma cells (squares). FIG. 7D is a graph showing CD47 re-expression in JinB8 cells (JIN+CD47−V5) alters expression of c-Myc compared with WT Jurkat cells. FIG. 7E is a graph showing effects of CD47-binding peptide 7N3 and control peptide 604 on c-Myc mRNA in Jurkat T cells. FIGS. 7F and G are graphs showing mRNA levels in TSP1-null vs. WT lung (FIG. 7F) and spleen. (FIG. 7G). For each condition, from left to right, bars indicate c-Myc, Sox2, Oct4, Nestin, and Klf4. FIG. 7H is a graph showing CD47 over-expression in Rat1 fibroblasts (right bars) and B16 melanoma cells (left bars) does not suppress growth. FIG. 7I is a graph showing deregulation of translocated c-Myc in Raji Burkitt's lymphoma cells prevents growth regulation by CD47 over-expression. ($*p<0.05$, $**p<0.01$).

FIG. 8A is a series of digital images of WT (top) or CD47-null (bottom) cultures at 7 days after each passage (P1-P3). FIG. 8B is a series of digital images of WT cells at passage 2 (left), which showed a flattened morphology characteristic of senescent cells, while CD47-null cells (right) maintained a typical endothelial morphology. The growth of both WT and CD47 null lung endothelial cells slowed after passages 3-5. WT cells grew very slowly and became stationary senescent cells. On the other hand, CD47 null cells initially flattened but resumed growth within 2-3 weeks. CD47 null cells restarted growth as colonies of well differentiated endothelial cells that maintained extensive cell-cell contact (cobblestone morphology) and required passage twice a week. Independent isolates of CD47 null endothelial cells reproducibly maintained their growth and morphology for at least 6 months. WT cells never resumed growth. FIG. 8C is a pair of digital images of mouse lung endothelial cells from WT and thrombospondin-1 null mice. Equal numbers of WT and thrombospondin-1 null murine lung endothelial cells were plated at the indicated passage numbers. After growth in EGM medium plus 0.5% FBS, viable cells were quantified by trypsinization, centrifugation, and counting on a hemocytometer in the presence of Trypan blue (FIG. 8D).

FIG. 9A is a series of digital images of formation of embryoid bodies by CD47-null endothelial cells transferred into serum free neural basal medium. Sequential photographs of a representative culture are shown. FIG. 9B is a series of digital images showing selective formation of EB-like clusters by passage 2 CD47-null endothelial cells in serum-free medium. Adherent cells (left) and non-adherent cells (right) were imaged 36 hours after transfer into serum-free medium. Nascent non-adherent EB-like clusters were abundant in the CD47-null culture, but only one loose cluster of cells was observed in the WT control. The latter cells did not survive at later times.

FIGS. 10A-H are a series of digital images of WT (FIGS. 10A-D) and CD47-null (FIGS. 10E-H) mouse lung endothelial cells cultured in EGM2 medium and then transferred to serum-free medium to induce embryoid bodies and stained for pluripotent stem cell markers Alkaline phosphatase activity (dark staining) was observed in embryoid body cells derived from CD47-null endothelial cells (FIGS. 10E-G), whereas no alkaline phosphatase activity was observed in WT cells, which failed to form EBs (FIGS. 10B-D).

FIGS. 11A-G show morphological and biochemical analysis of differentiated embryoid bodies derived from CD47-null cells for 10-15 days. FIGS. 11A-B show differentiated EBs under bright field and phase contrast illumination, respectively. Representative H&E stained section shows morphological evidence for ectodermal, mesodermal, and endodermal differentiation (FIGS. 11C-F). A 5 µm formalin fixed paraffin embedded differentiated embryoid body stained with H&E (4× objective, FIG. 11C) indicates the presence of all three germ cells layers: cuboidal endodermal epithelium with slightly atypical nuclei (H&E 40× objective, FIG. 11D), mesoderm or primitive mesenchyme with oval/fusiforme nuclei embedded in a myxoid matrix (H&E 40× objective, FIG. 11E). Some of the cells (arrows) contain eosinophilic amorphous material. Numerous apoptotic bodies are also seen (H&E 40×, FIG. 11E). FIG. 11F also shows presumptive ectoderm with pluristratified monotonous, basophilic nuclei mimicking primitive neuroectoderm (H&E 20×, FIG. 11F). FIG. 11G is a Western blot showing biochemical analysis of embryoid bodies for presence of three germ layer markers TUJI, AFP and SMA.

FIG. 12A shows ectoderm differentiation marker expression by cells derived from CD47-null EB-like clusters formed in serum-free medium. Phase contrast image of EB-like clusters (a) and differentiation of neural precursor cells from EBs (b and high magnification in c). Neural microtubule-associated protein-2 (MAP2) expression in embryoid body cells (d) and in a differentiated adherent cell (e). Expression of glial fibrillary acidic protein (GFAP, f), neuron-specific beta III tubulin (g), and S100b astrocyte marker (h) on adherent cells grown from embryoid bodies in neural differentiation medium. FIG. 12B shows endoderm differentiation marker expression by cells derived from CD47-null EB-like clusters formed in serum-free medium. Morphology of WT mouse lung endothelial cells in Hepatocyte medium (a), embryoid body formation by CD47-null lung endothelial cells in Hepatocyte medium (b), expression of endodermal marker AFP in CD47-null lung endothelial cells in Hepatocyte medium (c), no expression of AFP in CD47-null endothelial cells grown in EGM2 medium (d), WT mouse lung endothelial cells in mesenchymal medium (e), and CD47 null cells in mesenchymal medium with embryoid body formation (f). Adherent cell outgrowth from differentiating embryoid bodies (g) and differentiated cells stained for adipocyte marker Oil red O staining (h-i). FIG. 12C shows expression of the mesoderm marker smooth muscle actin by CD47 null cells grown from serum-free embryoid bodies transferred into smooth muscle differentiation medium.

FIGS. 13A-L shows hematopoietic differentiation from CD47-null endothelial cells. FIGS. 13A-C show representative morphologies of colonies generated by growth of CD47-null lung endothelial cells in semisolid medium and FIG. 13D shows a typical rare colony in WT cultures. FIGS. 13E and F show morphology of CD47 null mouse lung endothelial cells in EGM2 medium (FIG. 13E) or L929 conditional medium (FIG. 13F). CD47 null endothelial cells in EGM2 medium do not express macrophage marker Mac2 (FIG. 13G), but CD47 null endothelial cells in L929 conditioned medium express Mac2 (FIG. 13H) and show loss of Sca-1 expression (FIG. 13I). The cells were confirmed to lack CD47 expression (FIG. 13J). Immunohistochemical detection of Sox2-expression (brown) in representative spleen sections from WT (FIG. 13K) and CD47 null mice (FIG. 13L).

FIGS. 14A-H show additional data for CD47 re-expression effects. FIG. 14A shows knockdown of CD47 expression in vivo by CD47-morpholino (MO). FIG. 14B shows re-expression of human CD47-V5 in mouse lung endothelial cells. FIG. 14C shows relative expression of c-MYC (right bars) and CD47 (left bars) in transfected cells as compared to that in human umbilical vein endothelial cells (HUVEC). FIG. 14D shows TSP1 reduces c-MYC expression in Jurkat cells (left bars for each condition) and when CD47 is re-expressed in JinB8 cells (right bars for each condition). FIG. 14E shows expression level of CD47 in transfected JinB8 cells relative to WT Jurkat cells. FIG. 14F-H show CD47 induced cell cytotoxicity in mouse lung endothelial cells but not in cells with dysregulated c-Myc: FIG. 14F shows re-expression of CD47-FLAG in the presence and absence of c-Myc-GFP in mouse endothelial cells induced cell cytotoxicity. In each condition, from left to right, bars indicate WT, CD47-null, and CD47-null+Myc-GFP. FIG. 14G shows lack of cytotoxicity induced by re-expression of CD47-FLAG in Raji Burkitt's lymphoma cells. FIG. 14H shows cytotoxicity induced by re-expression of CD47-FLAG in B16 melanoma cells, Rat 1 fibroblasts and CD47 null lung endothelial cells. In each condition, from left to right, bars indicate B16, rat1 fibroblast, and CD47-null cells.

FIG. 16B) or with the function blocking anti-human CD47 antibody B6H12 (1 µg/ml; FIG. 16C) dramatically increased the sustained proliferation of these cells.

FIG. 18C).

SEQUENCE LISTING

Figure 1C:
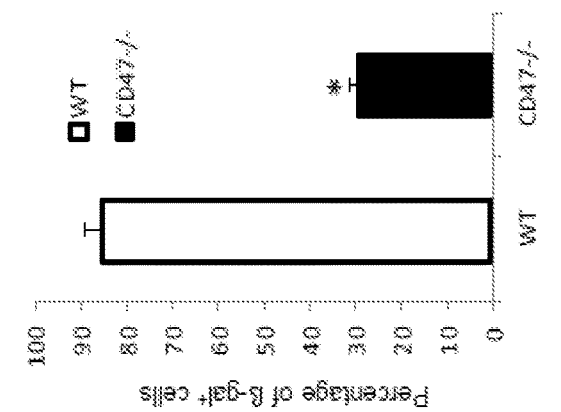
FIGS. 1A-1C show enhanced proliferation and decreased senescence of CD47-null murine endothelial cells.
Figure 1B:
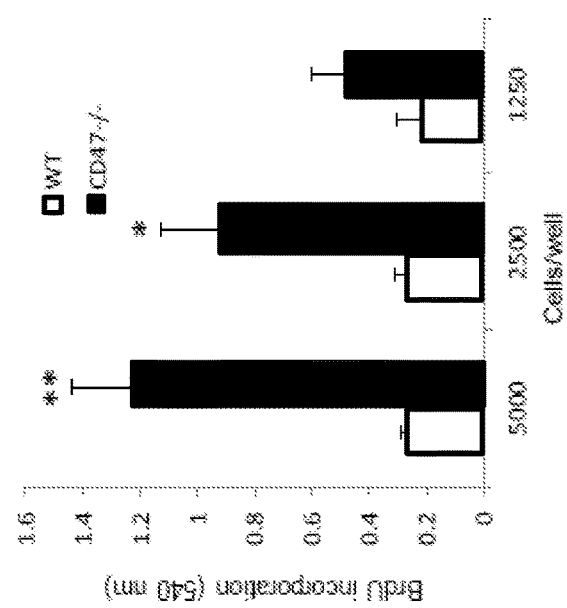

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is the thrombospondin-1-derived CD47-binding peptide 7N3 (1102-1112).

SEQ ID NO: 2 is the inactive control peptide 604.

SEQ ID NOs: 3 and 4 are forward and reverse primers for detection of murine Nestin expression.

SEQ ID NOs: 5 and 6 are forward and reverse primers for detection of murine Klf4 expression.

SEQ ID NOs: 7 and 8 are forward and reverse primers for detection of murine Sox2 expression.

SEQ ID NOs: 9 and 10 are forward and reverse primers for detection of murine Oct4 expression.

SEQ ID NOs: 11 and 12 are forward and reverse primers for detection of murine Myc expression.

SEQ ID NOs: 13 and 14 are forward and reverse primers for detection of murine E2F expression.

SEQ ID NOs: 15 and 16 are forward and reverse primers for detection of murine p16INK4a expression.

SEQ ID NOs: 17 and 18 are forward and reverse primers for detection of murine TPR53 expression.

SEQ ID NOs: 19 and 20 are forward and reverse primers for detection of murine RB expression.

SEQ ID NOs: 21 and 22 are forward and reverse primers for detection of murine HPRT1 expression.

SEQ ID NOs: 23 and 24 are forward and reverse primers for detection of murine B2M expression.

SEQ ID NOs: 25 and 26 are forward and reverse primers for detection of human B2M expression.

SEQ ID NOs: 27 and 28 are forward and reverse primers for detection of human Myc expression.

SEQ ID NOs: 29 and 30 are forward and reverse primers for detection of human FBP expression.

SEQ ID NOs: 31 and 32 are forward and reverse primers for detection of human HPRT1 expression.

SEQ ID NOs: 33 and 34 are forward and reverse primers for detection of murine TAF9 expression.

SEQ ID NO: 35 is an antisense morpholino oligonucleotide complementary to human and murine CD47.

SEQ ID NO: 36 is a 5-base mismatch control morpholino.

SEQ ID NO: 37 is a CD47 binding peptide (also known as peptide 459 or 4N1).

SEQ ID NO: 38 is the inactive control peptide 761.

DETAILED DESCRIPTION

I. Abbreviations

ANOVA analysis of variance
BrdU 5-bromo-2'-deoxyuridine
Ca capsule
cGMP cyclic guanine monophosphate
DMEM Dulbecco's Modified Eagle Medium
EB embryoid body
EGM endothelial growth medium
ES embryonic stem
FBS fetal bovine serum
GFP green fluorescent protein
HUVEC human umbilical vein endothelial cell
iPS induced pluripotent stem
LIF leukemia inhibitory factor
MPSCs multipotent stem cells
MTS 3-(4,5-dimethylthiazol-2-yl)-5-(3-carboxymethoxyphenyl)-2-(4-sulfophenyl)-2H-tetrazolium
NO nitric oxide
PBS phosphate buffered saline
PSCs pluripotent stem cells
RP red pulp
sGC soluble guanylyl cyclase
TSP1 thrombospondin-1
WP white pulp
WT wild type II. Terms Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Animal: Living multi-cellular vertebrate organisms, a category that includes, for example, mammals and birds. The term mammal includes both human and non-human mammals. Similarly, the term subject includes both human and veterinary subjects, for example, humans, non-human primates, rodents, dogs, cats, horses, and cows.

Administration: Administration of an active compound or composition can be by any route known to one of ordinary skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body, for example, via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system. Systemic administration also includes oral administration, in some examples.

Altered expression: Expression of a biological molecule (for example, mRNA or protein) in a subject or biological sample from a subject that deviates from expression if the same biological molecule in a subject or biological sample from a subject having normal or unaltered characteristics for the biological condition associated with the molecule. Normal expression can be found in a control, a standard for a population, etc. Altered expression of a biological molecule may be associated with a disease. The term associated with includes an increased risk of developing the disease as well as the disease itself. Expression may be altered in such a manner as to be increased or decreased. The directed alteration in expression of mRNA or protein may be associated with therapeutic benefits.

Altered protein expression refers to expression of a protein that is in some manner different from expression of the protein in a normal (wild type) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of an decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (for example, organ or tissue specific) expression of the protein (such that the protein is not expressed where it would normally be expressed or is expressed where it normally would not be expressed), each compared to a control or standard.

Controls or standards appropriate for comparison to a sample, for the determination of altered expression, include samples believed to express normally as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in *Remington* (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce F(ab)'$_2$, a dimer of Fab which itself is a light chain joined to $V_H$-$C_H$ 1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods, compositions, and systems of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994). One or more CDRs may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target—usually a polypeptide—such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Antisense, Sense, and Antigene: Double-stranded DNA (dsDNA) has two strands, a 5'->3' strand, referred to as the plus strand, and a 3'->5' strand (the reverse complement), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Cell Culture: Cell culture or culturing cells refers to placing cells in a dish, flask, or other container with an appropriate medium (such as a growth medium or differentiation medium) for the type of cells utilized (such as a medium including glucose, essential amino acids, vitamins, trace elements, salts, a buffer to maintain pH, and/or other components for particular applications).

Differentiation: Refers to the process whereby relatively unspecialized cells (such as embryonic stem cells or other stem cells) acquire specialized structural and/or functional features characteristic of mature cells. Similarly, "differentiate" refers to this process. Typically, during differentiation, cellular structure alters and tissue-specific proteins appear.

Differentiation Medium: A synthetic set of culture conditions with the nutrients necessary to support the growth or survival of microorganisms or culture cells, and which allows the differentiation of undifferentiated cells (such as committed mesenchymal cells) into differentiated cells, such as islet cells. Differentiation media generally include glucose, essential amino acids, vitamins, trace elements, salts, a buffer to maintain pH, and/or other components for particular applications. In one embodiment, a growth medium contains a minimal essential media, supplemented with specific growth factors.

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during an expansion phase, the cells do not differentiate to form mature cells, but divide to form more cells.

Functionally equivalent sequence variant: Sequence alterations that yield the same results as described herein. Such sequence alterations can include, but are not limited to, deletions, base modifications, mutations, labeling, and insertions.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a subject to an agent that inhibits gene expression. Expression of a gene also may be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression may be measured at the RNA level or the protein level and by any method known in the art, including Northern blot, RT-PCR, Western blot, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation includes but is not necessarily limited to overexpression, underexpression, or suppression of expression. In addition, it is understood that modulation of nucleic acid expression may be associated with, and in fact may result in, a modulation in the expression of an encoded protein or even a protein that is not encoded by that nucleic acid.

Interfering with or inhibiting gene expression refers to the ability of an agent to measurably reduce the expression of a target gene. Expression of a target gene may be measured by any method known to those of ordinary skill in the art, including for example measuring mRNA or protein levels. It is understood that interfering with or inhibiting gene expression is relative, and does not require absolute suppression of the gene. Thus, in certain embodiments, interfering with or inhibiting gene expression of a target gene requires that, following application of an agent, the gene is expressed at least 5% less than prior to application, at least 10% less, at least 15% less, at least 20% less, at least 25% less, or even more reduced. Thus, in some particular embodiments, application of an agent reduces expression of the target gene by about 30%, about 40%, about 50%, about 60%, or more. In specific examples, where the agent is particularly effective, expression is reduced by 70%, 80%, 85%, 90%, 95%, or even more. Gene expression is substantially eliminated when expression of the gene is reduced by 90%, 95%, 98%, 99% or even 100%.

Growth factor: A substance that promotes cell growth, survival, and/or differentiation. Growth factors include molecules that function as growth stimulators (mitogens), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are a fibroblast growth factor (such as FGF-2), epidermal growth factor (EGF), cilliary neurotrophic factor (CNTF), nerve growth factor (NGF), activin-A, and insulin.

Growth medium or expansion medium: A synthetic set of culture conditions with the nutrients necessary to support the growth (cell proliferation/expansion) of a specific population of cells. In one embodiment, the cells are stem cells, such as induced pluripotent or multipotent stem cells. In other examples, the cells are primary cells obtained from an animal or subject. Growth media generally include glucose, essential amino acids, vitamins, trace elements, salts, a buffer to maintain pH, and/or other components for particular applications. In one embodiment, ES growth medium contains a minimal essential media, such as DMEM, supplemented with various nutrients to enhance ES cell growth. Additionally, the minimal essential media may be supplemented with additives such as horse, calf or fetal bovine serum.

Immortalized: Capable of undergoing at least 25, 50, 75, 90, or 95% more cell divisions than a naturally-occurring control cell of the same cell type, genus, and species as the immortalized cell or than the donor cell from which the immortalized cell was derived. Preferably, an immortalized cell is capable of undergoing at least 2, 5, 10, or 20-fold more cell divisions than the control cell. In one embodiment, the immortalized cell is capable of undergoing an unlimited number of cell divisions. Examples of immortalized cells include cells that naturally acquire a mutation in vivo or in vitro that alters their normal growth-regulating process. Other immortalized cells include cells that have been genetically modified to express an oncogene, such as ras, myc, abl, bcl2, or neu, or that have been infected with a transforming DNA or RNA virus, such as Epstein Barr virus or SV40 virus (Kumar et al., *Immunol. Lett.* 65:153 159, 1999; Knight et al., *Proc. Nat. Acad. Sci. USA* 85:3130 3134, 1988; Shammah et al., *J. Immunol. Methods* 160 19 25, 1993; Gustafsson and Hinkula, Hum. Antibodies Hybridomas 5:98 104, 1994; Kataoka et al., *Differentiation* 62:201 211, 1997; Chatelut et al., *Scand. J. Immunol.* 48:659 666, 1998). Cells can also be genetically modified to express the telomerase gene (Rogues et al., *Cancer Res.* 61:8405 8507, 2001). In other examples, cells are treated with a substance that makes them capable of undergoing increased numbers of cell divisions than an untreated cell of the same type.

Inhibiting protein activity: To decrease, limit, or block an action, function or expression of a protein. The phrase "inhibit protein activity" is not intended to be an absolute term. Instead, the phrase is intended to convey a wide range of inhibitory effects that various agents may have on the normal (for example, uninhibited or control) protein activity. Inhibition of protein activity may, but need not, result in an increase in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator.

Inhibition of protein activity may also be effected, for example, by inhibiting expression of the gene encoding the protein or by decreasing the half-life of the mRNA encoding the protein.

Isolated: An isolated biological component (such as a nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been isolated thus include nucleic acids and proteins purified by standard purification methods. The term also embraces nucleic acids, peptides and proteins prepared by recombinant expression in a host cell as well as chemically synthesized nucleic acids. The terms isolated and purified do not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation.

Modulator: An agent that increases or decreases (modulates) the activity of a protein or other bio-active compound, as measured by the change in an experimental biological parameter. A modulator can be essentially any compound or mixture (for example, two or more proteins), such as a NO donor, a polypeptide, a hormone, a nucleic acid, a sugar, a lipid and the like.

Morpholino: A morpholino oligo is structurally different from natural nucleic acids, with morpholino rings replacing the ribose or deoxyribose sugar moieties and non-ionic phosphorodiamidate linkages replacing the anionic phosphates of DNA and RNA. Each morpholino ring suitably positions one of the standard bases (A, G, C, T/U), so that a 25-base morpholino oligo strongly and specifically binds to its complementary 25-base target site in a strand of RNA via Watson-Crick pairing. Because the backbone of the morpholino oligo is not recognized by cellular enzymes of signaling proteins, it is stable to nucleases and does not trigger an innate immune response through the toll-like receptors. This avoids loss of oligo, inflammation or interferon induction. Morpholinos can be delivered by a number of techniques, including direct injection to tissues or via infusion pump and intravenous bolus. A morpholino is one example of a stabilized nucleic acid molecule.

Non-immortalized: A cell that cannot divide indefinitely in vitro. In some embodiments, the non-immortalized cell does not have a nucleic acid mutation that alters its normal growth-regulating process. In some embodiments, the non-immortalized cell does not have two copies of the same recessive oncogene. In some embodiments, the non-immortalized cell cannot undergo 4-fold, 3-fold, 2-fold, or 1.5-fold more cell divisions in vitro and retain the same phenotype as the initial cell.

Nucleic acid molecule: A polymeric form of nucleotides, which may include both sense and antisense strands of RNA, cDNA, genomic DNA, and synthetic forms and mixed polymers thereof. A nucleotide refers to a ribonucleotide, deoxynucleotide or a modified form of either type of nucleotide. A nucleic acid molecule as used herein is synonymous with nucleic acid and polynucleotide. A nucleic acid molecule is usually at least 10 bases in length, unless otherwise specified. The term includes single- and double-stranded forms. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of ordinary skill in the art. Such modifications include, for example, labels, methylation, substitution of one or more of the naturally occurring nucleotides with an analog, inter-nucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, the left hand end of a polynucleotide sequence written in the sense orientation is the 5' end and the right hand end of the sequence is the 3' end. In addition, the left hand direction of a polynucleotide sequence written in the sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

An antisense nucleic acid is a nucleic acid (such as, an RNA or DNA oligonucleotide) that has a sequence complementary to a second nucleic acid molecule (for example, an mRNA molecule). An antisense nucleic acid will specifically bind with high affinity to the second nucleic acid sequence. If the second nucleic acid sequence is an mRNA molecule, for example, the specific binding of an antisense nucleic acid to the mRNA molecule can prevent or reduce translation of the mRNA into the encoded protein or decrease the half-life of the mRNA, and thereby inhibit the expression of the encoded protein.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include stabilized oligonucleotides, such as peptide nucleic acid (PNA) molecules and morpholinos.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Pluripotent refers to a cell's potential to differentiate into cells of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent stem cells can give rise to any fetal or adult cell type. Alone they cannot develop into a fetal or adult animal because they lack the potential to contribute to extra-embryonic tissue (e.g., placenta in vivo or trophoblast in vitro).

Pluripotent stem cells (PSCs) are the source of multipotent stem cells (MPSCs) through spontaneous differentiation or as a result of exposure to differentiation induction conditions in vitro. The term multipotent refers to a cell's potential to differentiate and give rise to a limited number of related, different cell types. These cells are characterized by their multi-lineage potential and the ability for self-renewal. In vivo, the pool of multipotent stem cells replenishes the population of mature functionally active cells in the body. Among the exemplary multipotent stem cell types are hematopoietic, mesenchymal, or neuronal stem cells.

Transplantable cells include multipotent stem cells and more specialized cell types such as committed progenitors as well as cells further along the differentiation and/or maturation pathway that are partly or fully matured or differentiated. Exemplary transplantable cells include pancreatic, epithelial, cardiac, endothelial, liver, endocrine, and the like.

Polypeptide: A polymer in which the monomers are amino acid residues that are joined together through amide bonds. When the amino acids are alpha-amino acids, either the L-optical isomer or the D-optical isomer can be used, the L-isomers usually being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some circumstances, variations in the cDNA sequence that result in amino acid changes, whether conservative or not, are minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, or even 95% or 98% identical to the native amino acid sequence. Programs and algorithms for determining percentage identity can be found at the NCBI website.

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates at least one sign or symptom of a disease or pathological condition, or interferes with a pathophysiological process after it has begun to develop. Treatment includes inhibiting or preventing the partial or full development or progression of a disease, for example in a person who is known to have a predisposition to a disease.

Primary cells: Cells directly obtained or isolated from tissue. Primary cells are not transformed and are not immortalized. These cells generally do not proliferate indefinitely when placed in cell culture unless they undergo spontaneous immortalization or malignant transformation. Primary cells obtained from a tissue may include a population of multiple cell types, including multiple types of differentiated cells, lineage-committed cells, and/or stem cells (such as adult stem cells, for example hematopoietic stem cells, mesenchymal stem cells, or neural stem cells). Primary cells obtained from a tissue may also include primarily a single cell type (or a single cell type may be isolated or selected from a population of primary cells), such as human umbilical vein endothelial cells (HUVEC).

Purified: In a more pure form than is found in nature. The term purified does not require absolute purity; rather, it is intended as a relative term. Thus, for example, a purified protein preparation is one in which the protein referred to is more pure than the protein in its natural environment within a cell.

The term substantially purified as used herein refers to a molecule (for example, a nucleic acid, polypeptide, oligonucleotide, etc.) that is substantially free of other proteins, lipids, carbohydrates, or other materials with which it is naturally associated. In one embodiment, a substantially purified molecule is a polypeptide that is at least 50% free of other proteins, lipids, carbohydrates, or other materials with which it is naturally associated. In another embodiment, the polypeptide is at least at least 80% free of other proteins, lipids, carbohydrates, or other materials with which it is naturally associated. In yet other embodiments, the polypeptide is at least 90% or at least 95% free of other proteins, lipids, carbohydrates, or other materials with which it is naturally associated.

RNA interference (RNA silencing; RNAi): A gene-silencing mechanism whereby specific double-stranded RNA (dsRNA) trigger the degradation of homologous mRNA (also called target RNA). Double-stranded RNA is processed into small interfering RNAs (siRNA), which serve as a guide for cleavage of the homologous mRNA in the RNA-induced silencing complex (RISC). The remnants of the target RNA may then also act as siRNA; thus resulting in a cascade effect.

Senescence: The biological process(es) of aging and showing the effects of increased age. In one embodiment, a senescent cell does not divide and/or has a reduced capacity to divide.

Small molecule inhibitor: A molecule, typically with a molecular weight less than 1000, or in some embodiments, less than about 500 Daltons, wherein the molecule is capable of inhibiting, to some measurable extent, an activity of some target molecule.

Stabilized nucleic acid molecules: A variety of synthetic nucleic acid derivatives with increased stability as compared to native (e.g., non-modified) nucleic acids. Stabilized nucleic acid molecules include nucleic acids where the labile phosphodiester bonds in nucleic acids are replaced with more stable phosphoramidates or peptide amide backbones, or oligonucleotides including one or more such nucleic acid derivatives. Also included are nucleic acids having a substitution of the deoxyribosyl moiety with a more stable morpholine derivative (e.g., morpholinos) or oligonucleotides including one or more morpholino nucleic acids. In other examples, stabilized nucleic acid molecules include "locked" nucleic acids where the ribose moiety is modified with a bridge connecting the 2' oxygen and the 4' carbon, or oligonucleotides including one or more locked nucleic acid.

Stem cell: A cell that can generate a fully differentiated functional cell of a more than one given cell type. The role of stem cells in vivo is to replace cells that are destroyed during the normal life of an animal. Generally, stem cells can divide asymmetrically without limit and may be lineage-committed, totipotent, or pluripotent. After division, the stem cell may remain as a stem cell, become a precursor cell, or proceed to terminal differentiation. A nervous system stem cell is, for example, a cell of the central nervous system that can self-renew and can generate astrocytes, neurons and oligodendrocytes.

A "somatic precursor cell" is a cell that can generate a fully differentiated functional cell of at least one given cell type from the body of an animal, such as a human. A neuronal precursor cell can generate of fully differentiated neuronal cell, such as, but not limited to, and adrenergic or a cholinergic neuron. A glial precursor cell can generate fully differentiated glial cells, such as but not limited to astrocytes, microglia and oligodendroglia. Generally, precursor cells can divide and are pluripotent. After division, a precursor cell can remain a precursor cell, or may proceed to terminal differentiation. A neuronal precursor cell can give rise to one or more types of neurons, such as dopaminergic, adrenergic, or serotonergic cells, but is more limited in its ability to differentiate than a stem cell. In one example, a neuronal stem cell gives rise to all of the types of neuronal cells (such as dopaminergic, adrenergic, and serotonergic neurons) but does not give rise to other cells, such as glial cells.

Target sequence: A target sequence is a portion of ssDNA, dsDNA, or RNA that, upon hybridization to a therapeutically effective oligonucleotide or oligonucleotide analog (e.g., a morpholino), results in the inhibition of expression of the target. Either an antisense or a sense molecule can be used to target a portion of dsDNA, as both will interfere with the expression of that portion of the dsDNA. The antisense molecule can bind to the plus strand, and the sense molecule can bind to the minus strand. Thus, target sequences can be ssDNA, dsDNA, and RNA.

Totipotent or totipotency refers to a cell's ability to divide and ultimately produce an organism and its extra-embryonic tissues in vivo. In one aspect, the term "totipotent" refers to the ability of the cell to progress through a series of divisions into a blastocyst in vitro. The blastocyst comprises an inner cellular mass (ICM) and a trophoblast. By ICM is meant the cells surrounded by the trophectoderm. The inner cell mass cells give rise to most of the fetal tissues upon further development. The cells found in the ICM give rise to pluripotent stem cells that possess the ability to proliferate indefinitely, or if properly induced, to differentiate into all cell types contributing to an organism. By "trophectoderm" is meant the outermost layer of cells surrounding the blastocoel during the blastocyst stage of primate embryonic development. Trophectoderm becomes trophoblast and gives rise to most or all of the placental tissue upon further development. Trophoblast cells generate extra-embryonic tissues, including placenta and amnion.

Therapeutic: A generic term that includes both diagnosis and treatment.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, oligonucleotide, or antibody) in blood (in vivo) or a buffer (in vitro) that produces an effect.

Tissue Matrix: A scaffold having a three-dimensional structure of an organ, tissue, or portion thereof, but substantially lacking cellular content. A tissue matrix can be a decellularized organ (for example, liver, kidney, heart, lung, bladder, trachea, or esophagus) or portion thereof or tissue (for example, vessel, valve, skin, bone, joint, airway, urethra, nerve, cornea, retina, inner ear, muscle, or cartilage). The decellularized organ or tissue preserves the composition and structure of the extracellular matrix of the organ but the cells are substantially removed. A tissue matrix also includes a synthetic organ (or portion thereof) or tissue scaffold made of synthetic biocompatible extracellular matrices that can support tissue regeneration.

Under conditions sufficient for: A phrase that is used to describe any environment that permits the desired activity. In one example, includes administering a therapeutically effective amount of a composition that includes a peptide, antibody, or oligonucleotide (e.g., morpholino), sufficient to enable the desired activity.

Unless otherwise explained, all technical and scientific terms used herein have the same meaning as commonly understood by one of ordinary skill in the art to which this invention belongs.

The singular terms "a," "an," and "the" include plural referents unless context clearly indicates otherwise. Similarly, the word or is intended to include and unless the context clearly indicates otherwise. Hence "comprising A or B" means "including A, or including B, or including A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety.

In case of conflict, the present specification, including explanations of terms, will control. In addition, the materials, methods, and examples are illustrative only and not intended to be limiting.

III. Thrombospondin and CD47

Thrombospondin 1 (TSP1; also known as THBS1) is an extracellular secreted protein that is involved in a myriad of cellular processes, including platelet aggregation, neurite outgrowth, cell motility, cell survival, and cellular proliferation. Among TSP1's best-characterized functions is inhibition of angiogenesis. Angiogenesis ameliorates the poor oxygenation of damaged tissue that is a limiting factor for patient recovery in a variety of clinical settings, including surgery, burn wound healing, amputation, stroke, pulmonary arterial hypertension, peripheral vascular disease, and myocardial infarction. Because it is desirable to promote angiogenesis within these contexts, antagonizing TSP1's activity has been a valuable research objective. Additionally, tumors require vascularization for growth. Agents that mimic the ability of TSP1 to inhibit angiogenesis are therefore considered possible therapies for cancer. In vitro studies have shown the ability of such agents to block tumor driven angiogenesis. In vivo results in animals have also been encouraging and have led to clinical trials in people. See Rusk et al., *Clin Cancer Res* 12:7456-7464, 2006; Markovic et al., *Am J Clin Oncol* 30:303-309, 2007.

TSP1 contains three type 1 repeat structural domains and a carboxy-terminal domain that were identified as the loci of the full-length protein's anti-angiogenic functionality (Lawler, *Curr. Opin. Cell Biol.* 12(5): 634-640, 2000). TSP1 sequences are publically available, such as GenBank Accession Nos. NM_003246 and NM_011580 (nucleic acids) and NP_003237 and NP_035710 (protein), all of which are incorporated herein by reference as present in GenBank on Dec. 10, 2012. One of ordinary skill in the art can identify additional TSP1 sequences, including variant sequences.

Overexpression of TSP1 has been observed in ischemic tissue, and is proposed to regulate angiogenesis within ischemic tissue (Favier et al., *J Pathol.* 207(3): 358-366, 2005), since TSP1 preferentially interferes with wound healing-associated angiogenesis (Streit et al., *EMBO J.* 19(13): 3272-3282, 2000) and limits revascularization in a model of hind limb ischemia similar to that employed by the current inventors (Kopp et al., *J. Clin. Invest.* 116(12): 3277-3291, 2006). Peptides derived from the type 1 repeats inhibit angiogenesis (Shafiee et al., *IOVS* 41(8): 2378-2388, 2000; Yee et al., *Am J. Pathol.* 165(2): 541-552, 2004; Tolsma et al., *J. Cell Biol.* 122: 497-511, 1993; Armstrong and Bornstein, *Mat. Biol.* 22(1): 63-71, 2003; Guo et al., *Cancer Res.* 58(14): 3154-3162, 1998; Guo et al., *J. Peptide Res* 50:210-221, 1997). Additional TSP1 peptides (e.g., 4N1 and 7N3 classes) have previously been described; see, e.g., U.S. Pat. Nos. 5,399,667; 5,627,265; 6,469,138; 5,357,041; 5,491,130; 5,770,563; 5,849,701; 6,051,549; 6,384,189; 6,458,767; and 7,129,052.

TSP1 acts through several cellular receptors, including CD36 and integrin-associated protein (IAP)/CD47. It was originally thought that TSP1 exerted its anti-angiogenic effects by acting through CD36 (Quesada et al., *Cell Death and Diff.* 12:649-658, 2005; Jimenez et al., *Nat Med.* 6(1): 41-48, 2000; de Fraipon et al., *Trends Mol. Med.* 7(9):401-407, 2001). However, CD36 is unlikely to be responsible for the anti-angiogenic actions of TSP1. For example, short peptides comprised of the TSP1 type 1 repeat can inhibit FGF- and VEGF-induced migration of human endothelial cells that lack CD36 binding (Vogel et al., *J. Cell. Biochem.* 53:74-84, 1993; Guo et al., *J. Peptide Res* 50:210-221, 1997; Short et al., *J Cell Biol.* 168(4): 643-653, 2005). A sequence in the carboxy-terminal domain of TSP1 that binds to CD47 inhibits nitric oxide-mediated pro-angiogenic signaling (Isenberg et al., *J. Biol. Chem.* 281:26069-26080, 2006) and was shown to have anti-angiogenic activity (Kanda et al., *Exp Cell Res.* 252(2):262-72, 1999). Recombinant C-terminal domain of TSP1 that contains this sequence and binds to CD47 also inhibits NO signaling in endothelial cells and was shown to have anti-angiogenic activity (Kanda et al., *Exp Cell Res.* 252(2):262-72, 1999) in CD36-null, but not CD47-null cells. In contrast with the results from TSP1-derived peptides, the use of oligonucleotides to inhibit production of TSP1 suggested a contributory role of TSP1 in excisional dermal wound healing (DiPietro et al., *Am J. Pathol.* 148(6): 1851-1860, 1996). This activity is mediated by regulation of the chemokine MIP1. In contrast, ischemic wounds heal better in mice lacking either TSP1 or CD47 and display more vigorous angiogenic responses (Isenberg et al., *Ann. Surg.* 247:860-868, 2008). CD36 null mice showed no advantage for healing ischemic wounds, revealing that the anti-angiogenic activity of TSP1 in an ischemic environment is mediated by CD47 rather than CD36. Likewise, in skin graft healing enhanced graft take is obtained in CD47 null wounds compared to either WT or CD36 null wounds.

CD47 is an atypical member of the immunoglobulin and the G protein-coupled receptor superfamilies. It consists of an N-terminal extracellular IgV set domain, 5 transmembrane segments and an alternatively spliced cytoplasmic tail (Brown and Frazier, *Trends Cell Biol.* 11(3): 130-135, 2001). CD47 sequences are publically available, such as GenBank Accession Nos. NM_198793, NM_001777, and NM_010581 (nucleic acids) and NP_942088, NP_001768, and NP_034711 (protein), all of which are incorporated herein by reference as present in GenBank on Dec. 10, 2012. One of ordinary skill in the art can identify additional CD47 sequences, including variant sequences.

Although identified earlier as "integrin associated protein" (IAP), CD47 was discovered to be a high affinity receptor for the C-terminal domain of TSP1 in 1996 (Gao et al., *J. Biol. Chem.* 271: 21-24, 1996; Isenberg et al., *J. Biol. Chem.* 284: 1116-1125, 2009). Two members of the signal inhibitory receptor protein family, SIRPα (also known as BIT, SHPS-1 and p84) and SIRPγ are cell-bound counter receptors for CD47 (van Beek et al., *J. Immunol.* 175:7781-87, 2005). CD47 is expressed on many if not all normal cells, and signals in part through coupling to heterotrimeric G proteins of the G, class (Frazier et al., *J. Biol Chem.* 274:8554-8560, 1999).

TSP1, via binding to CD47, potently limits physiologic NO signaling in all vascular cell types including endothelial cells, vascular smooth muscle cells, and platelets and inflammatory cells. TSP1-CD47 signaling also directly and acutely regulates tissue blood flow and arterial tone by inhibiting NO-driven vasorelaxation, and exerts anti-vasorelaxive effects on smooth muscle by antagonizing the ability of NO to stimulate cGMP synthesis (Isenberg et al., *Proc Natl Acad Sci USA.* 102(37): 13141-13146, 2005; Isenberg et al., *Cardiovasc Res.,* 71(4):785-793, 2006;); Isenberg et al., *J Biol Chem* 281:26069-26080, 2006, Isenberg et al., *Blood,* 109(5):1945-1952, 2007) and through its ability to rapidly upregulate NADPH-oxidase (Nox) to increase production of superoxide, a potent NO scavenger (Csanyi et al., *Artherioscl. Thromb. Vasc. Biol.* 32:2966-73, 2012). Though inhibition of NO signaling may be induced by TSP1 interacting with CD36, this effect occurs at doses 100- to 1000-fold greater than the doses of TSP1 that drive inhibition through CD47. Also, TSP1 inhibition of NO signaling through CD36 cannot occur in the absence of CD47 at any dose; thus, the physiologically relevant pathway is via CD47 (Isenberg et al., *J Biol Chem.* 281(36):26069-26080, 2006). See also International Patent Publication No. WO 2008/060785, which is incorporated herein by reference in its entirety.

The structure and function of CD47 has been explored using anti-CD47 antibodies and peptide ligands of the receptor. Certain anti-CD47 and TSP1-derived CD47 ligands initiate cell death in breast cancer cell lines (Manna and Frazier, *Cancer Res.* 64:1026-1036, 2004) and Jurkat T cells (Manna and Frazier, *J Immunol.* 170(7):3544-3553, 2003). These, and similar experiments, led to the hypothesis that CD47 is necessary for FAS-mediated apoptosis of Jurkat T cells (Manna et al., *J. Biol. Chem.* 280(33):29637-29644, 2005). Synthetic peptides derived from the full-length sequence of CD47 have been used to probe its structure (Rebres et al., *J. Biol. Chem.* 276(37):34607-34616, 2001). Ligation of CD47 induces actin polymerization (Rebres et al., *J. Biol. Chem.* 276(10):7672-7680, 2001), and its ligation by peptides derived from the carboxy-terminus of TSP1 stimulates the integrin-mediated adhesion of melanoma cells to specific substrates (Barazi et al., *J. Biol. Chem.* 277(45):42859-42866, 2002; Gao et al., *J. Cell Biol.* 135(2):533-544, 1996).

Different antibodies engaging CD47 can exert opposing stimulatory and inhibitory effects on cells (Li et al., *J Immunol* 166:2427-2436, 2001; Waclavicek et al., *J Immunol* 159:5345-5354, 1997; Pettersen et al., *J Immunol* 162: 7031-7040, 1999; Ticchioni et al., *J Immunol* 158:677-684, 1997). Likewise, a specific CD47 ligand can act as an agonist or an antagonist in different contexts. For instance, CD47 ligation by a particular ligand may have different effects in isolated cells than in vivo. Therefore, some effects of CD47 antibodies that have been defined using isolated cells do not extrapolate to in vivo activities, and the function of a specific CD47 ligand in vivo cannot be predicted solely on the basis of in vitro testing. However, agents that block CD47 function in vitro consistently show protective activities in mouse, rat, and pig models of stress. These include fixed ischemia, ischemia-reperfusion, and radiation injury (Maxhimer et al., *Plast. Reconstr. Surg.* 124:1880-1889, 2009; Maxhimer et al., *Sci. Transl. Med.* 1:3ra7, 2009). Some of this tissue protection is mediated by increased NO/cGMP signaling, but additional cytoprotective pathways are also involved, including mitigation of pathologic reactive oxygen species (Bauer et al., *Cardiovasc. Res.* 88: 471-481, 2010; Csanyi et al., *Artherioscl. Thromb. Vasc. Biol.* 32:2966-73, 2012). For example, radioprotection caused by CD47 blockade involves activation of a protective autophagy pathway (Soto-Pantoja et al., *Autophagy* 8:1628-1642, 2012). This protective autophagy response is evident in isolated cells and in tissues of an irradiated mouse. Furthermore, the proliferative and survival advantage of cells lacking CD47 or TSP1 described herein reveal another important pro-survival activity of CD47 blockade that is conserved in isolated cells and living tissues of mammals. Without being limited by theory, this activity appears to be mediated by overcoming TSP1/CD47 signaling that limits the self-renewal and reprogramming capacities of cells via inhibiting the expression of c-Myc and other transcription factors that are critical for stem cell maintenance.

IV. Generation of Pluripotent and Multipotent Cells and Differentiated Cells Disclosed herein are methods for generating or inducing pluripotent or multipotent stem cells, methods for generating lineage-committed or differentiated cells, and methods for maintaining and/or expanding stem cells or differentiated cells in culture. It is shown herein that blockade of CD47/TSP1 signaling dramatically increases the proliferative capacity of primary cells and also induces expression of stem cell marker genes (such as c-Myc, Sox2, Klf4, and Oct4). These cells are capable of forming embryoid bodies (EBs) or EB-like clusters and differentiation into many different cell types upon exposure to suitable culture conditions (such as culture with a differentiation medium). Thus, the disclosed methods include contacting cells (such as primary cells, stem cells, or differentiated cells) with one or more agents that block CD47 signaling. Without being bound by theory, it is believed that in at least some cases, primary cells isolated from an animal contain lineage-committed stem cells that can become multi- or pluripotent when CD47 signaling is blocked.

A. Inducing Pluripotent or Multipotent Stem Cells

In particular embodiments, the described methods include obtaining primary cells (such as lineage-committed (differentiated) cells) from an animal or subject, culturing the primary cells, and contacting the obtained cells with an agent that can block CD47 signaling. Multipotent or induced pluripotent stem cells are produced from the CD47-blocked cells when the blocked cells are cultured in appropriate culture media, which in particular embodiments is a serum-free medium.

In some examples, the methods include obtaining primary cells from an animal (such as a human or a non-human mammal). Primary cells can be obtained from any tissue of interest, including without limitation, liver (e.g., hepatocytes), lung (e.g., lung endothelial cells), bone marrow (such as myeloid cells or lymphoid cells), spleen, skin (e.g., fibroblasts, melanocytes, or keratinocytes), adipose tissue (e.g., adipocytes or mesenchymal cells), heart (e.g., cardiomyocytes or cardiac valve endothelial cells), smooth muscle, blood vessels (e.g., vascular smooth muscle or vascular endothelial cells, such as umbilical vein endothelial cells), lymph vessels (e.g., lymphatic endothelial cells), skeletal muscle (e.g., myoblasts), tendons (e.g., tenocytes), neural tissue (e.g., neurons, astrocytes, or glial cells), bone (e.g., osteocytes), pancreas (e.g., islet cells), oral or nasal mucosal biopsies, dental pulp, or hair follicles. In particular examples, primary cells can be obtained from adipose tissue (such as adipocytes), dermal biopsy (such as mesenchymal fibroblasts), or bone marrow aspirates (such as hematopoietic precursors, also referred to as hemangioblasts or hematopoietic stem cells). In additional examples, primary cells can be obtained from umbilical cord or umbilical cord blood or foreskins from newborns (such as fibroblasts, keratinocytes, and/or microvascular endothelial cells).

Primary cells obtained from a tissue may include a population of multiple cell types, including multiple types of differentiated cells, lineage-committed cells, and/or stem cells (such as adult stem cells, for example hematopoietic stem cells, mesenchymal stem cells, or neural stem cells). Primary cells obtained from a tissue may also include primarily a single cell type or a single cell type may be isolated or selected from a population of primary cells.

Methods for obtaining primary cells are known to one of ordinary skill in the art. For example, a tissue or a portion thereof is collected from an animal, incubated with an enzyme to release cells (such as collagenase, trypsin, or pronase) in a growth medium for a period of time sufficient to dissociate the cells (such as about 5 minutes to 2 hours), and plated in a cell culture dish with growth medium. Cells are incubated at a temperature of about 37° C. (such as about 34° C. to about 39° C.) in an atmosphere containing about 5% $CO_2$ (such as about 4-6% $CO_2$). Primary cells are also commercially available, for example from Lonza (Basel, Switzerland), Life Technologies (Carlsbad, Calif.), PromoCell (Heidelberg, Germany), and ScienCell (Carlsbad, Calif.), and also from the American Type Culture Collection (Manassas, Va.) or other cell repositories.

In some examples, primary cells (such as primary cells obtained from a subject) are placed in a cell culture dish with an appropriate cell culture medium for the type of primary cells utilized (such as a medium including glucose, essential amino acids, vitamins, trace elements, salts, a buffer to maintain pH, and/or other components for particular applications). For example, if the primary cells are endothelial cells (such as lung endothelial cells or HUVECs), the cell culture medium is an endothelial cell growth medium. In one particular example, the endothelial cell growth medium is EGM2 (Lonza, Basel, Switzerland), which includes hydrocortisone, hEGF, VEGF, hFGFb, R3-IGF-1, fetal bovine serum, ascorbic acid, heparin, and gentamicin/amphotericin B. In other examples, if the primary cells are epithelial cells (such as hepatocytes), the cell culture medium is a hepatocyte cell culture medium and if the primary cells are fibroblasts, the cell culture medium is a fibroblast cell culture medium. One of ordinary skill in the art can select an appropriate cell culture medium for a particular type of primary cell. Primary cell culture media are also commercially available, for example from Lonza, Life Technologies (Carlsbad, Calif.), BD Biosciences (San Jose, Calif.), and Sigma-Aldrich (St. Louis, Mo.). In some examples, the primary cells may be cultured for at least 1 day (such as at least 1, 2, 3, 4, 5, 6, 7, 8, 9, 10, 11, 12, 13, 14, or more days) prior to contacting the cells with an inhibitor of CD47 signaling. In other examples, the primary cells are cultured for at least 1 passage (such as at least 1, 2, 3, 4, 5, 6, 7, 8, 9, or 10 passages) prior to contacting the cells with an inhibitor of CD47 signaling.

The primary cells (such as cultured primary cells) are contacted with an effective amount of an inhibitor of CD47 signaling. Inhibitors of CD47 signaling are discussed in detail in Section V, below. In some examples, the inhibitor is included in the culture medium (for example, if the inhibitor is a peptide, antibody, or small molecule). In other examples, the cells are transformed or transfected with the inhibitor (for example, if the inhibitor is an antisense or stabilized oligonucleotide, such as a morpholino oligonucleotide, or a plasmid encoding a siRNA or dsRNA). One of ordinary skill in the art can select an appropriate mode for contacting the cells with the inhibitor.

The cells are contacted with the inhibitor of CD47 signaling for a period of time sufficient to achieve the desired effect, such as generation or expansion of iPS or multipotent stem cells. In some examples, presence of iPS or multipotent stem cells in the culture is identified by increased expression of c-Myc, SSEA1, c-Kit, Sca-1, nestin, Nanog, or other stem cell markers or increased ability of the cells to proliferate in culture (for example as compared to an untreated cell of the same type). In some examples, the expression of stem cell markers (such as c-Myc, Sox2, Klf4, nestin, Nanog, or Oct4) in cells treated with a CD47 signaling inhibitor is increased by at least 10%, 20%, 30%, 40%, 50%, 60%, 70%, 80%, 90%, 2-fold, 3-fold, 4-fold, 5-fold, 6-fold, 7-fold, 8-fold, 9-fold, 10-fold, 15-fold, 20-fold or more as compared to a control. In other examples, the cells treated with a CD47 signaling inhibitor proliferate in culture for at least one more passage (such as 2, 3, 4, 5, 6, 7, 8, 9, 10, 15, 20, or more passages) or at least one more day (such as 2, 3, 4, 5, 6, 7, 10 days, 2, 3, 4, 5, 6, 7 weeks, or 2, 3, 4, 5, 6 months or more) as compared to a control.

The cells are contacted with an amount of the CD47 signaling inhibitor that is sufficient to achieve the desired effect, such as generation or expansion of iPS or multipotent stem cells, as discussed above. In some embodiments, the cells are contacted with a peptide, antibody, or small molecule inhibitor, which can be included in the cell culture medium. In some examples, the inhibitor is a peptide (such as a CD47 binding peptide, for example SEQ ID NO: 1 or SEQ ID NO: 37, disclosed herein). The cells are contacted with about 1 nM to 100 mM peptide (such as about 10 nM to 10 mM, 100 nM to 1 mM, 100 nM to 10 µM, or 1 µM to 100 µM). In some examples, the cells are contacted with about 1 µM peptide (for example, about 1 µM 7N3 peptide). The cells are contacted with the peptide for at least 1 day and can be contacted with the peptide continuously, for any desired period of time for the maintenance and/or expansion of the cells. In some examples, the cells are contacted with the peptide for about 1, 2, 3, 4, 5, 6, 7, 10 days, about 2, 3, 4, 5, 6, 7 weeks, or about 2, 3, 4, 5, 6 months or more. In additional examples, the cells are contacted with the peptide transiently, for about 1 day to 4 weeks or more (such as about 1, 2, 3, 4, 5, 6, 7 days, 2, 3, 4, weeks, or more) and then are subsequently maintained in culture without the peptide for about 1 week or more. In some embodiments, the cells are contacted with a peptide which is in solution in the tissue culture medium. In other embodiments, the cells are contacted with a peptide which is immobilized on a tissue culture substrate, a natural tissue matrix, or a synthetic matrix by adsorption or covalent attachment.

In other examples, the cells are contacted with an anti-CD47 antibody, including, but not limited to B6H12 (e.g., Gresham et al., *J. Cell Biol.* 108:1935-1943, 1989, and Brown et al., *J. Cell Biol.* 111:2785-2794, 1990; for example, commercially available from Santa Cruz Biotechnology, as catalog number sc-12730), MIAP301 (e.g., Chang et al., *Neuroscience* 102(2):289-296, 2001; commercially available for instance from RDI Division of Fitzgerald Industries Intl., as catalog number RDI-MCD47-301), or OX101 (for example, commercially available from Santa Cruz Biotechnology, as catalog number sc-53050). In additional examples, the cells are contacted with an anti-TSP1 antibody, such as A6.1 or C6.7 (see, e.g., Annis et al., *J. Thromb. Haemost.* 4:459-468, 2006; Abcam catalog numbers ab1823 and ab140257, respectively). The cells are contacted with about 10 ng/ml to 1 mg/ml antibody (such as about 100 ng/ml to 500 µg/ml, 500 ng/ml to 100 µg/ml, or 100 ng/ml to 10 µg/ml, 1 µg/ml to 50 µg/ml, or 1 µg/ml to 10 µg/ml). In some examples, the cells are contacted with about 1 µg/ml of the antibody. The cells are contacted with the antibody for at least 1 day and can be contacted with the antibody continuously, for any desired period of time for the maintenance and/or expansion of the cells. In some examples, the cells are continuously contacted with the antibody for about 1, 2, 3, 4, 5, 6, 7, 10 days, about 2, 3, 4, 5, 6, 7 weeks, or about 2, 3, 4, 5, 6 months or more. In additional examples, the cells are transiently contacted with the antibody for example, for about 1 day to 4 weeks or more (such as about 1, 2, 3, 4, 5, 6, 7 days, 2, 3, 4, weeks, or more) and then are subsequently maintained in culture without the antibody for about 1 week or more. In some embodiments, the cells are contacted with an antibody which is in solution in the tissue culture medium. In other embodiments, the cells are contacted with an antibody which is immobilized on a tissue culture substrate, a natural tissue matrix, or a synthetic matrix by adsorption or covalent attachment.

In additional examples, the inhibitor is a small molecule inhibitor of CD47 signaling. The cells are contacted with about 0.1 nM to 1 M of the small molecule inhibitor (such as about 1 nM to 100 mM, 10 nM to 10 mM, 100 nM to 1 mM, 100 nM to 10 µM, or 1 µM to 100 µM). The cells are contacted with the small molecule for at least 1 day and can be contacted with the small molecule continuously, for any desired period of time for the maintenance and/or expansion of the cells. In some examples, the cells are continuously contacted with the small molecule for about 1, 2, 3, 4, 5, 6, 7, 10 days, about 2, 3, 4, 5, 6, 7 weeks, or about 2, 3, 4, 5, 6 months or more. In additional examples, the cells are transiently contacted with the small molecule, for example for about 1 day to 4 weeks or more (such as about 1, 2, 3, 4, 5, 6, 7 days, 2, 3, 4, weeks, or more) and then are subsequently maintained in culture without the small molecule for about 1 week or more. In some embodiments, the cells are contacted with a small molecule which is in solution in the tissue culture medium.

In other embodiments, the cells are contacted with an oligonucleotide inhibitor of CD47 signaling (such as an antisense or stabilized oligonucleotide complementary to a CD47 or TSP1), which can be introduced to the cells by transfection or transformation. The oligonucleotide inhibitor can include without limitation antisense, inhibitory RNA (RNAi), small inhibitory RNA (siRNA), short hairpin RNA (shRNA), microRNA (miRNA), lncRNA, and circRNA oligonucleotides. Methods for introducing nucleic acids to cells are known to one of ordinary skill in the art, and include but are not limited to, liposomal-mediated transfection, electroporation, and conjugation of the oligonucleotide compound to a cell-penetrating peptide. Transfection of oligonucleotides generally involves the use of liposomal-mediated transfection reagents (such as LIPOFECTAMINE™), a number of which are commercially available. Methods for transfection and electroporation of nucleic acids, including antisense compounds, are well known in the art (see, for example, U.S. Pat. Nos. 7,307,069 and 7,288,530; Pretchtel et al., *J. Immunol. Methods* 311(1-2):139-52, 2006; Ghartey-Tagoe et al., *Int. J. Pharm.* 315 (1-2):122-133, 2006, each of which are herein incorporated by reference). In additional examples, the oligonucleotides can be delivered with a vector, such as a viral vector (for example, an adenovirus, lentivirus, or adeno-associated virus vector). In still further examples, the oligonucleotide can be delivered to the cells by an endocytosis-mediated process (e.g., ENDO-PORTER, Gene Tools, Inc., Corvallis, Oreg.; U.S. Pat. No. 7,084,248). About 1 nM to 100 mM oligonucleotide (such as about 10 nM to 10 mM, 100 nM to 1 mM, 0.1 µM to 10 µM, 1 µM to 100 µM, 1 µM to 10 µM or 2.5 µM) is transfected or otherwise introduced to the cells. Introduction of the oligonucleotide to the cells can be repeated one or more times if desired. For example, the cells can be transfected (or otherwise treated) at intervals of 1 day or more (such as 1, 2, 3, 4, 5, 6, 7, 8, 9, 10, 11, 12, 13, 14 days, or more). In other examples, a single exposure of cells to the oligonucleotide (even in the absence of transfection techniques or agents) or single dose to a subject is used. In particular examples, the inhibitor is an antisense morpholino oligonucleotide complementary to CD47 (such as SEQ ID NO: 35).

In additional embodiments, the methods include generating embryoid bodies or EB-like clusters from the iPS or multipotent stem cells generated as described above. In some examples, cells which have been contacted with an agent that inhibits CD47 signaling are transferred to serum-free medium and cultured for at least one day (such as 1, 2, 3, 4, 5, 6, 7 days or more). In some examples, embryoid bodies or EB-like clusters are maintained in culture for at least 1 day or more (such as at least about 1, 2, 3, 4, 5, 6 days; about 1, 2, 3, 4, 5, 6 weeks; or about 1, 2, 3 or more months). One of ordinary skill in the art can identify formation of EBs, such as by morphology (for example, formation of cell aggregates) or expression of pluripotent stem cell markers (for example, alkaline phosphatase, SSEA-1, c-Kit, nestin, Nanog, Oct4, Sox2, and/or Klf4).

B. Generating Differentiated Cells

In some embodiments, the disclosed methods include producing a desired differentiated cell type from a previously lineage-committed cell type. Desired cell types can be produced by generating multipotent or iPS cells using a CD47 blocking agent as described above, and then culturing the iPS cells in media containing appropriate differentiating factors. The newly-differentiated cells can also be immortalized for storage. Such cells will maintain their differentiated state in the appropriate media, which can be selected by one of ordinary skill in the art.

Induced pluripotent or multipotent stem cells or EBs are produced as described above. Cells are then transferred to a differentiation medium containing factors appropriate for obtaining the desired cell type(s). In some examples, the differentiation medium includes one or more agents that inhibit CD47 signaling. In other examples, the differentiation medium does not include an agent that inhibits CD47 signaling. One of ordinary skill in the art can select appropriate differentiation media, including, but not limited to those described below. In some embodiments, the methods include obtaining primary cells from a subject, culturing the primary cells, contacting the primary cells with an agent that blocks CD47 signaling, and isolating cells that express at least one stem cell marker (such as at least 1, 2, 3, 4, 5, or more stem cell markers) from the cells contacted with the CD47 inhibitor. In some example, the stem cell markers include one or more of c-Myc, Oct4, Sox2, Klf4, Nanog, SSEA1, c-Kit, or Sca-1. The cells that express the one or more stem cell markers are then cultured in serum-free medium to produce iPS or multipotent stem cells and culturing the iPS or multipotent stem cells in a cell differentiation medium to produce differentiated cells.

In some examples, the iPS or multipotent stem cells or EBs are cultured in a differentiation medium that results in generation of cells having characteristics of ectoderm-derived lineages (such as neural cells, for example, neurons, astrocytes, glia, cranial or sensory neurons and/or ganglia; pigment cells; head connective tissues, epidermis, mammary gland, or hair). In a particular example, iPS cells are transferred into a neural differentiation medium, such as serum-free EBM basal medium (for example, commercially available from Lonza, Basel, Switzerland) supplemented with FGF2 and EGF (about 5-20 ng/ml), heparin, and gentamycin sulfate. In some examples, cells form neurospheres (EBs) in 1-2 days, which are then plated onto non-tissue culture dishes in the same medium, but lacking heparin. In other examples, the neurospheres are dispersed and cultured with EBM basal medium supplemented with FGF2 and EGF (about 5-20 ng/ml), gentamycin sulfate, and StemPro Neural supplement (Life Technologies, Carlsbad, Calif.). In some examples, the medium includes one or more agents that inhibit CD47 signaling. In other examples, the medium does not include an agent that inhibits CD47 signaling. Formation of neural precursor cells or neural cells (for example after about 1, 2, 3, 4, 5, 6, 7 days or more) can be determined by morphology (such as neurite formation) or by expression of neuron markers (such as MAP2, glial fibrillary acidic protein (GFAP), βIII-tubulin) or astrocyte markers (such as S100b). These cells can be maintained in culture and passaged multiple times, or can be stored at −80° C. for later use.

In other examples, the iPS or multipotent stem cells or EBs are cultured in a differentiation medium that results in generation of cells having characteristics of mesoderm-derived lineages (such as smooth muscle, endothelial, cartilage, chondrocyte, dermis of skin, connective tissue, urogenital system tissue, heart tissue, hematopoietic, and/or myeloid cells). In one example, iPS cells are transferred into a smooth muscle cell differentiation medium, such as Smooth Muscle Basal Medium (for example, commercially available from Lonza, Basel, Switzerland) supplemented with PDGF (10 ng/ml) and TGFβ1 (5 ng/ml). In some examples, the medium includes one or more agents that inhibit CD47 signaling. In other examples, the medium does not include an agent that inhibits CD47 signaling. In some examples, cells form EBs in 1-2 days, which are then plated onto gelatin-coated tissue culture dishes in the same medium. Formation of smooth muscle cells can be determined by morphology (such as presence of typical vascular smooth muscle morphology) or by expression of smooth muscle cell markers (such as smooth muscle actin). These cells can be maintained in culture and passaged multiple times, or can be stored at −80° C. for later use.

In another example, iPS cells or multipotent stem cells or EBs are transferred into a differentiation medium including hematopoietic growth factors (e.g., as described in Maxhimer et al., *Sci. Transl. Med.* 1:3ra7, 2009). In some examples, the cells are cultured on a semi-solid medium. Formation of hematopoietic cells can be determined by cell morphology (such as formation of colonies with phenotypic characteristics of myeloid or erythroid cells) or by expression of hematopoietic cell markers (for example, CD34, CD11a, CD11b, CD117, AML1, CD2, CD3, CD4, CD8, Gr1, Mac1, and/or B220). In a further example, myeloid cells generated as described above can be cultured with a macrophage differentiation medium (such as medium supplemented with macrophage colony stimulating factor). Macrophages can be identified by cell morphology and expression of macrophage markers (such as Mac-2). In some examples, the medium includes one or more agents that inhibit CD47 signaling. In other examples, the medium does not include an agent that inhibits CD47 signaling. These cells can be maintained in culture and passaged multiple times, or can be stored at −80° C. for later use.

In further examples, the iPS or multipotent stem cells or EBs are cultured in a differentiation medium that results in generation of cells having characteristics of endoderm-derived lineages (such as hepatocytes, adipocytes, pancreatic beta-cells, gastrointestinal and respiratory epithelial cells, endocrine secretory cells, bladder and/or urethral epithelial cells). In one example, iPS cells are transferred into a hepatocyte differentiation medium, such as DMEM with L-glutamine, penicillin/streptomycin and 1% ITS (e.g., commercially available from multiple suppliers, including Life Technologies, Carlsbad, Calif.) supplemented with HGF (e.g. 20 ng/ml), Oncostatin M (e.g., 10 ng/ml), and dexamethasone (e.g., 10 nM). In some examples, the medium includes one or more agents that inhibit CD47 signaling. In other examples, the medium does not include an agent that inhibits CD47 signaling. In some examples, cells form EBs in 1-2 days, which then form hepatocytes. Formation of hepatocytes can be determined by morphology or by expression of hepatocyte markers (such as α-fetoprotein). These cells can be maintained in culture and passaged multiple times, or can be stored at −80° C. for later use.

In another example, iPS or multipotent stem cells or EBs are transferred into a mesenchymal cell differentiation medium, such as such as a basal medium supplemented with adipogenic factors (e.g., commercially available from BD Biosciences, ScienCell, or Life Technologies). In some examples, the medium includes one or more agents that inhibit CD47 signaling. In other examples, the medium does not include an agent that inhibits CD47 signaling. In some examples, cells form EBs in 1-2 days, which then form adipocytes. Formation of adipocytes can be determined by presence of lipid vacuoles (for example, positive for Oil Red O) or by expression of adipocyte markers (such as RABP4, adiponectin, adipocytokines, and/or leptin). These cells can be maintained in culture and passaged multiple times, or can be stored at −80° C. for later use.

One of ordinary skill in the art can identify additional differentiation media and cell culture conditions appropriate to differentiate the disclosed iPS or multipotent stem cells or EBs to other cell types. The differentiation conditions provided herein are exemplary, and should not be considered to be limiting.

C. Expanding Stem Cells or Differentiated Cells

The disclosed methods include maintaining and/or expanding stem cells in a de-differentiated state capable of self-renewing proliferation by continued exposure of the cells to an agent that blocks CD47 signaling. The de-differentiated state is maintained as long as the cells are cultured in appropriate media and exposed to a CD47 blocking agent. In some embodiments transient exposure to a CD47 blocking agent is sufficient to induce this de-differentiated state resulting in cells capable of self-renewing proliferation. The cells (such as stem cells, for example, induced pluripotent or multipotent stem cells) are contacted with an agent that blocks CD47 signaling as described above and are maintained and passaged in culture utilizing standard techniques.

In additional embodiments, the disclosed methods include maintaining and/or expanding differentiated cells (such as primary lineage-committed cells or cells differentiated from induced pluripotent stem cells) by continued exposure of the cells to an agent that blocks CD47 signaling. The cells are cultured in appropriate media and exposed to a CD47 signaling blocking agent, as described above. In some examples, the differentiated cells are maintained or expanded in medium includes one or more agents that inhibit CD47 signaling. In other examples, the differentiated cells are maintained or expanded in medium does not include an agent that inhibits CD47 signaling.

V. Compositions and Methods for CD47/TSP1 Blockade

The disclosed methods include inhibiting or blocking CD47 signaling (such as CD47/TSP1 signaling), for example to induce formation of pluripotent stem cells or to generate lineage-committed stem cells. In various embodiments, inhibiting CD47 signaling includes one or more of inhibiting the expression of CD47, inhibiting the expression of TSP1, removing endogenous TSP1 or CD47, or blockading or inhibiting the interaction between endogenous TSP1 and CD47.

Agents that block or inhibit CD47 signaling include but are not limited to peptides, antibodies, antisense oligonucleotides, morpholinos, or small molecule inhibitors. The agent that inhibits CD47 signaling includes, in various embodiments, a synthetic peptide having specific binding affinity for CD47; a synthetic peptide having specific binding affinity for TSP1; an oligonucleotide comprising at least about 15 contiguous bases and that hybridizes to the mature or unprocessed nuclear mRNA of CD47 under high stringency conditions; an oligonucleotide comprising at least about 15 contiguous bases and that hybridizes to the mRNA of TSP1 under high stringency conditions; an isolated or recombinant TSP1 or CD47 molecule or soluble fragment thereof, or molecule that binds thereto; an agent that decreases the expression of CD47; an agent that decreases the expression of TSP1; an agent that enhances the proteolysis of CD47; an agent that enhances the proteolysis of TSP1; an agent that enhances removal of CD47 from the cell surface; a CD47 antagonist; an antibody that specifically binds TSP1; an antibody that specifically binds CD47; or a mixture of two or more thereof. Exemplary inhibitors of CD47 signaling include those described in U.S. Pat. No. 8,236,313 and International Pat. Publ. No. WO 2010/017332, both of which are incorporated herein by reference in their entirety.

A. Suppression of Protein Expression

In some embodiments, inhibition or blockade of CD47 signaling is achieved by reducing or suppressing TSP1 or CD47 protein expression, for example in methods of inducing pluripotent or multipotent stem cells or methods of generating lineage-committed stem cells or differentiated cells, such as exemplified herein.

Although the mechanism by which antisense RNA molecules interfere with gene expression has not been fully elucidated, it is believed that antisense RNA molecules (or fragments thereof) bind to the endogenous mRNA molecules and thereby inhibit translation of the endogenous mRNA, splicing of the nuclear mRNA precursor, or result in its degradation. A reduction of protein expression in a cell may be obtained by introducing into cells an antisense construct based on TSP1 or CD47 encoding sequences, including the human (or other mammalian) TSP1 cDNA or CD47 cDNA or gene sequence or flanking regions thereof. For antisense suppression, a nucleotide sequence from a TSP1- or CD47- encoding sequence, for example all or a portion of a TSP1 cDNA or gene or all or a portion of a CD47 cDNA or gene, is arranged in reverse orientation relative to the promoter sequence in the transformation vector. One of ordinary skill in the art will understand how other aspects of the vector may be chosen.

The introduced sequence need not be the full length of the cDNA or gene, or reverse complement thereof, and need not be exactly homologous to the equivalent sequence found in the cell type to be transformed. Generally, however, where the introduced sequence is of shorter length, a higher degree of homology to the native target sequence will be needed for effective antisense suppression. The introduced antisense sequence in the vector may be at least 15 nucleotides in length, and improved antisense suppression will typically be observed as the length of the antisense sequence increases. The length of the antisense sequence in the vector advantageously may be greater than about 20 nucleotides, greater than about 30 nucleotides, or greater than about 100 nucleotides. For suppression of the TSP1 gene itself, transcription of an antisense construct results in the production of RNA molecules that are the reverse complement of mRNA molecules transcribed from the endogenous TSP1 gene in the cell. For suppression of the CD47 gene itself, transcription of an antisense construct results in the production of RNA molecules that are the reverse complement of mRNA molecules transcribed from the endogenous CD47 gene in the cell.

Suppression of endogenous TSP1 or CD47 expression can also be achieved using ribozymes. Ribozymes are synthetic molecules that possess highly specific endoribonuclease activity. The production and use of ribozymes are disclosed in U.S. Pat. Nos. 4,987,071 and 5,543,508. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Suppression can also be achieved using RNA interference, using known and previously disclosed methods. Several models have been put forward to explain RNAi, in particular the mechanisms by which the cleavage derived small dsRNAs or siRNAs interact with the target mRNA and thus facilitate its degradation (Hamilton et al., *Science* 286:950, 1999; Zamore et al., *Cell* 101:25, 2000; Hammond et al., *Nature* 404:293, 2000; Yang et al., *Curr. Biol.* 10:1191, 2000; Elbashir et al., *Genes Dev.* 15:188, 2001; Bass *Cell* 101:235, 2000). It has been proposed that the cleavage derived small dsRNAs or siRNAs act as a guide for the enzymatic complex required for the sequence specific cleavage of the target mRNA. Evidence for this includes cleavage of the target mRNA at regular intervals of about 21-23 nucleotides in the region corresponding to the input dsRNA (Zamore et al., *Cell* 101, 25, 2000), with the exact cleavage sites corresponding to the middle of sequences covered by individual 21 or 22 nucleotide small dsRNAs or siRNAs (Elbashir et al., *Genes Dev.* 15:188, 2001). Although mammals and lower organisms appear to share dsRNA-triggered responses that involve a related intermediate (small dsRNAs), it is likely that there will be differences as well as similarities in the underlying mechanism. dsRNAs can be formed from RNA oligomers produced synthetically (for technical details see material from the companies Xeragon and Dharmacon, both available on the internet). Small dsRNAs and siRNAs can also be manufactured using standard methods of in vitro RNA production. In addition, the Silencer™ siRNA Construction kit (and components thereof) available from Ambion (Catalog #1620; Austin, Tex.), which employs a T7 promoter and other well-known genetic engineering techniques to produce dsRNAs. Double stranded RNA triggers could also be expressed from DNA based vector systems.

Inhibition also can be accomplished using morpholino oligonucleotides, for instance as described herein. The morpholino can be delivered directly to cells (for example, in vitro) or can be administered to a subject as herein described. In particular embodiments, the morpholino is an antisense morpholino oligonucleotide complementary to CD47 (such as human and/or murine CD47) or TSP1 (such as human and/or murine TSP1). In one non-limiting example is a CD47 morpholino with the nucleic acid sequence CGTCACAGGCAGGACCCACTGCCCA (SEQ ID NO: 35).

The nucleic acids and nucleic acid analogs that are used to suppress endogenous TSP1 or CD47 expression may be modified chemically or biochemically or may contain one or more non-natural or derivatized nucleotide bases, as will be readily appreciated by those of ordinary skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and/or modified linkages (for example, alpha anomeric nucleic acids, etc.). The term nucleic acid molecule also includes any topological conformation, including single-stranded, double-stranded, partially duplexed, triplexed, hair-pinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Additionally, although particular exemplary sequences are disclosed herein, one of ordinary skill in the art will appreciate that the present methods also encompass sequence alterations of the disclosed agents that yield the same results as described herein. Such sequence alterations can include, but are not limited to, deletions, base modifications, mutations, labeling, and insertions.

Suppression of protein expression may also be achieved through agents that enhance proteolysis of CD47 or TSP1 (Allen et al., *Endocrinology* 150:1321-1329, 2009). In other particular examples, the suppression of CD47 expression involves an agent that enhances the removal of CD47 from the cell surface or decreases the transcription, mRNA processing, or translation of CD47. Similar embodiments are envisioned, regarding suppression of TSP1.

B. Suppression of Protein Activity

In some embodiments, inhibition or blockade of CD47 signaling is achieved by reducing or suppressing TSP1 or CD47 protein activity, for example in methods of inducing pluripotent or multipotent stem cells or methods of generating lineage-committed stem cells or differentiated cells, such as exemplified herein.

In some examples, an inhibitor of CD47 signaling includes an agent that decreases or blocks binding of a ligand (such as TSP1) to CD47. The determination that an agent (such as an antibody or a peptide) inhibits the association between TSP1 and CD47 may be made, for example, using assays known to one of ordinary skill in the art. For instance, the determination that an agent inhibits TSP1 binding to purified or recombinant CD47 can be made by comparing the binding activity alone with the binding activity in the presence of the agent using a solid phase ligand binding assay. An agent that inhibits the activity of TSP1 to signal through CD47 on cells will reduce the activity of a cGMP-dependent reporter in a suitable transfected cell assay by a certain amount, for example, by 20%, 30%, 40%, 50%, 60%, 70%, 80%, 90%, or even by 100%. In addition, an agent that inhibits the activity or CD47 or TSP1 can be identified using any one of the assays described herein, including, but not limited to, determining c-Myc expression in a cell. An agent that inhibits CD47 signaling will increase c-Myc expression (such as an increase in c-Myc mRNA or c-Myc protein) in a cell or population of cells by a certain amount, for example by 20%, 30%, 40%, 50%, 60%, 70%, 80%, 90%, 100%, 150%, 200%, 250%, or more as compared to a suitable control.

Thus, in various embodiments an inhibitor of CD47 signaling includes antibodies (such as monoclonal antibodies or humanized antibodies) that specifically bind to CD47 or TSP1. In some examples, an antibody that specifically binds CD47 is of use in the methods disclosed herein. In other examples, an antibody that specifically binds TSP1 is of use in the methods disclosed herein. Antibodies that specifically bind to CD47 or TSP1 include polyclonal antibodies, monoclonal antibodies, or humanized monoclonal antibodies, or fragments thereof. Methods of constructing such antibodies are known in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992; Kohler & Milstein, *Nature* 256:495, 1975; Coligan et al., sections 2.5.1-2.6.7; and Harlow et al. in: Antibodies: a Laboratory Manual, page 726, Cold Spring Harbor Pub., 1988). In addition, such antibodies may be commercially available. In some examples, an inhibitor of CD47 signaling includes an anti-CD47 antibody, such as anti-CD47 antibodies B6H12, BRIC 126, 6H9, Clkm1, OVTL16, OX101, mIAP410, or mIAP301 (also referred to as ab301), a binding fragment of any one of these, or a humanized version of any one of these, or an antibody or fragment thereof that competes with B6H12, BRIC 126, 6H9, Clkm1, OVTL16, OX101, mIAP410, or mIAP301 for binding. In other examples, an inhibitor of CD47 signaling includes an anti-TSP1 antibody, such as C6.7, HB8432, D4.6, A65M, A4.1, A6.1, or SPM321, a binding fragment of any one of these, or a humanized version of any one of these, or an antibody or fragment thereof that competes with C6.7, HB8432, D4.6, A65M, A4.1, A6.1, or SPM321 for binding. It is to be understood that CD47 signaling inhibitors for use in the present disclosure also include novel CD47 or TSP1 antibodies developed in the future.

In other embodiments, an inhibitor of CD47 signaling includes a peptide that specifically binds to CD47 or TSP1. In some examples an inhibitor of CD47 signaling is a CD47-binding peptide, such as a TSP1-derived CD47-binding peptide. Exemplary CD47-binding peptides include 7N3 (FIRVVMYEGKK; SEQ ID NO: 1) and 4N1 (also known as 459; RFYVVMWK; SEQ ID NO: 37). Additional CD47-binding peptides include those described in U.S. Pat. No. 8,236,313, incorporated herein by reference in its entirety. It is to be understood that CD47 signaling inhibitors for use in the present disclosure also include novel CD47 or TSP1 binding peptides developed in the future.

In additional embodiments, an inhibitor of CD47 signaling includes a small molecule (such as a small organic molecule). Some small molecule inhibitors may inhibit CD47 or TSP1 expression or activity. It is to be understood that CD47 signaling inhibitors for use in the present disclosure also include novel CD47 or TSP1 small molecule inhibitors developed in the future.

VI. Therapeutic Uses

The methods disclosed herein can be used for the ex vivo generation and/or expansion of induced pluripotent or multipotent stem cells or lineage-committed (differentiated cells) for cell-based therapies and tissue engineering. The disclosed methods have several advantages over current methods of generating immortalized cells. The disclosed methods do not increase risk of malignant transformation of the cells, for example, because they do not use transformation of the cells (such as with T antigen) or telomerase. In addition, in at least some embodiments, the disclosed methods do not require use of bacterial or viral vectors for creating continuously proliferating cells. The disclosed methods also are more suitable for clinical uses because they utilize defined molecular entities. In other embodiments, the methods include administering an inhibitor of CD47 signaling to a subject.

Administration to cells of inhibitors of CD47 signaling can be local or systemic. Examples of local administration include, but are not limited to, topical administration, subcutaneous administration, transdermal administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration intended to distribute an active compound or composition widely throughout the body, for example, via the circulatory system. Thus, systemic administration includes, but is not limited to intra-arterial and intravenous administration. Systemic administration also includes, but is not limited to, topical administration, subcutaneous administration, transdermal administration, intramuscular administration, or administration by inhalation, when such administration is directed at absorption and distribution throughout the body by the circulatory system. Systemic administration also includes oral administration, in some examples.

In some embodiments, induced pluripotent or multipotent stem cells are generated by contacting primary cells with an agent that blocks CD47 signaling as described above, and increased numbers of these stem cells can be obtained by continuous culture of the cells with an agent that blocks CD47 signaling to obtain the desired number of cells. Similarly, a population of differentiated cells of a desired cell type can be generated by contacting primary cells with an agent that inhibits CD47 signaling, followed by culture in an appropriate differentiation medium, as described above, and increased numbers of these differentiated cells can be obtained by continuous culture of the cells with an agent that blocks CD47 signaling to obtain the desired number of cells.

In some embodiments, the resulting cells can be utilized for ex vivo tissue engineering applications. For example, the disclosed methods include increasing cell population of a tissue matrix by contacting the tissue matrix with cells and an inhibitor of CD47 signaling ex vivo. In some examples, the cells could be used to populate or repopulate a tissue matrix, for example a decellularized organ or natural tissue matrix or to populate a synthetic organ or synthetic tissue scaffold. Methods of preparing a decellularized tissue matrix are known to one of ordinary skill in the art (see, e.g., Gilbert, *J. Cell. Biochem.* 113:2217-2222, 2012, incorporated herein by reference). For example the iPS cells could be perfused into a decellularized organ or tissue matrix or a synthetic organ or tissue scaffold under conditions sufficient to permit seeding of the matrix or scaffold with the iPS cells and then to proliferate and differentiate to form a bioengineered organ. In some examples, cells (such as iPS cells) would be perfused into the matrix or scaffold in the presence of the CD47 signaling inhibitor, for example to seed the matrix, and then the matrix or scaffold would be perfused with an appropriate differentiation medium (which optionally may also include a CD47 signaling inhibitor), for example to permit differentiation of the cells. These methods could be used to bioengineer entire organs (such as a liver, kidney, heart, lung, bladder, trachea, or esophagus), which could then be transplanted into a subject in need of an organ transplant. These methods can also be used to bioengineer tissues or portions of organs, such as vessels for vascular graft, lymphatics, replacement heart valves, skin grafts, bone grafts, joint components (such as the femoral head), airways, urethra, pancreatic islets, nerves, cornea, retina, inner ear, cardiac muscle, or to replace cartilaginous tissue (such as in the trachea), which could then be transplanted into a subject in need of the organ or tissue. In some instances any decellularized matrix, natural or synthetic, can be combined with a CD47 signaling inhibitor agent, removing the barrier to cell invasion of, migration through, and restoration of the complex 3D structure. In particular examples, the methods increase cell population of a tissue matrix by at least about 10% (such as at least about 10%, 20%, 30%, 40%, 50%, 60%, 70%, 80%, 90%, 100%, or more) as compared to a tissue matrix contacted with cells but not contacted with an inhibitor of CD47 signaling.

In additional embodiments, the methods disclosed herein can be used to generate and/or expand populations of cells for administration to a subject. In one example, the disclosed methods could be used to expand pancreatic cells (such as islet cells), which could then be transplanted into a subject in need of pancreatic cells (for example, a subject with diabetes). In other examples, the disclosed methods could be used to generate and expand populations of hematopoietic cells (such as hematopoietic stem cells or myeloid- or lymphoid-committed cells) for a subject in need of such cells. In some examples, hematopoietic stem cells can be generated and/or expanded for bone marrow transplantation to a subject with cancer or a subject with an immune-deficiency or for treating a subject with radiation toxicity. Without being limited by theory, it is believed that by enhancing the potential of a marrow transplant by the disclosed methods may allow for decreased amount of marrow harvested and may increase the success rate of transplant. In yet other examples, the disclosed methods could be used to expand cytotoxic T cells for adoptive immunotherapy in subjects with cancer. One of ordinary skill in the art can select appropriate cell types and cell numbers to be administered to a subject to treat or inhibit a condition. In some examples, the methods include administering the cells to a subject by local administration (such as transplantation or injection into a tissue or organ) or systemic administration (such as intravenous administration). In other examples, the cells are administered to a subject by subcutaneous or transdermal administration, for example by injection into or under the skin. See, e.g., U.S. patent publications 2011/0110898, 2011/0274665, 2009/0130066, 2008/0311089, 2007/0207131, 2007/0154462, 2007/0154461, 2006/0039896, 2005/0271633, 2005/0186149, 2003/0228286, and 2002/0197241; as well as U.S. Pat. Nos. 5,591,444, 5,660,850, 5,665,372, and 5,858,390.

In other embodiments, the methods include administering an inhibitor of CD47 signaling to a subject, for example, to increase or generate induced pluripotent stem cells in vivo. The resulting iPS cells could for example repopulate damaged tissue (such as a wound or burn or a fractured bone) or enhance the effectiveness of a bone marrow cell transplant in a subject. Compositions including inhibitors of CD47 and their administration are described in U.S. Pat. No. 8,236,313 and U.S. Pat. Publ. Nos. 2011/013564; incorporated herein by reference.

In some embodiments, a CD47 signaling inhibitor (such as a peptide, antibody or antibody fragment, nucleic acid, or inhibitory oligonucleotide (e.g., morpholino)) is administered locally to an affected area, for example by direct administration to a wound or other site in which recruitment or generation of iPS is desired (e.g. pancreas or bone marrow), or is incorporated into an implant device and placed directly at an affected area, such as a wound or other tissue injury. In some embodiments, administration is, for example, by direct topical administration to a wound, or by intra-arterial, intravenous, subcutaneous, or intramuscular injection into the affected area. Efficacy of the treatment is shown, for example, by a regression of symptoms, for example wound healing or generation of new tissue or by increased skin temperature or a color change in the skin of the limbs. For subjects with a wound such as a burn or a graft, administration is, for example, by subcutaneous or intravenous injection, by direct injection of the wound or burn or graft bed, or by topical application. Efficacy of the treatment is determined, for example, by an improvement in wound healing.

In additional examples, administration of an inhibitor of CD47 signaling can be administered to enhance healing in conditions of delayed healing, such as non-union bone fractures, chronic wounds, or non-healing tendon injuries, for example by direct topical administration near or to a wound, or by intra-arterial, intravenous, subcutaneous, or intramuscular injection into the affected area.

In further examples, an effective amount of an inhibitor of CD47 signaling may be utilized to treat or prevent hair loss. The inhibitor of CD47 signaling is administered topically to an affected area (such as the scalp) or is administered transdermally or subcutaneously to an affected area, or optionally systemically.

In additional examples, iPS or multipotent stem cells or differentiated cells prepared according to the methods described herein or CD47 inhibitors may be administered to the eye (for example administered or implanted intravitreally) to treat a subject with vision loss. In some examples, the subject has a progressive vision disorder, such as retinal degeneration (for example, retinitis pigmentosa), macular degeneration, or glaucoma. Cells or CD47 inhibitors can be administered to the eye topically, for example topical preparations can include eye drops, ointments, sprays, patches and the like. Cells or compositions can also be included in an inert matrix for either topical application or injection into the eye, such as for intravitreal administration. Liposomes, including cationic and anionic liposomes, can be made using standard procedures as known to one skilled in the art. Liposomes can be applied topically, either in the form of drops or as an aqueous based cream, or can be injected intraocularly. The cells or CD47 inhibitors can also be included in a delivery system that can be implanted at various sites in the eye, depending on the size, shape and formulation of the implant, and the type of transplant procedure. The delivery system is then introduced into the eye. Suitable sites include but are not limited to the anterior chamber, anterior segment, posterior chamber, posterior segment, vitreous cavity, suprachoroidal space, subconjunctiva, episcleral, intracorneal, epicorneal and sclera.

An effective amount of a therapeutic CD47 inhibitor (such as a peptide, antibody, inhibitor peptide-encoding DNA, or oligonucleotide (e.g., morpholino)) can be administered in a single dose, or in multiple doses, for example daily, weekly, every two weeks, or monthly during a course of treatment. Additionally, the therapeutic agents may be incorporated into or on implantable constructs or devices, such as vascular stents, for sustained regional or local release.

In some examples, the methods include identifying or selecting a subject for administration of a CD47 signaling inhibitor or iPS or multipotent stem cells or differentiated cells prepared according to the methods described herein. For example, the methods include selecting a subject with damaged tissue (such as a burn, broken bone, wound, or other tissue damage), a subject in need of a bone marrow cell transplant (such as a subject with a hematological cancer or immune-deficiency or radiation toxicity), or a subject with diabetes and administering an inhibitor of CD47 signaling or iPS or multipotent stem cells or differentiated cells prepared according to the methods described herein to the selected subject. In other examples, the methods include selecting a subject with hair loss (such as alopecia, or radiation-induced alopecia) and administering an inhibitor of CD47 signaling or iPS or multipotent stem cells or differentiated cells prepared according to the methods described herein to the selected subject. In still further examples, the methods include selecting a subject with vision loss (such as retinal degeneration, macular degeneration, or glaucoma) and administering an inhibitor of CD47 signaling or iPS or multipotent stem cells or differentiated cells prepared according to the methods described herein to the selected subject.

VII. Kits

Also disclosed herein are kits that can be used to induce lineage-committed, pluripotent, or multipotent stem cells from primary cells, generate differentiated cells from primary cells, and/or expand stem cells or lineage-committed differentiated cells in culture. In some embodiments, the kit includes one or more agent that blocks CD47 signaling, such as one or more of an anti-CD47 antibody or fragment thereof, a CD47-binding peptide, a CD47 antisense oligonucleotide, a CD47 morpholino, an anti-TSP1 antibody or fragment thereof, a TSP1-binding peptide, a TSP1 antisense oligonucleotide, or a TSP1 morpholino. In other embodiments, the kit includes a small molecule capable of binding to CD47 or a small molecule capable of binding to TSP1.

In one example, the kit includes a CD47 morpholino, such as a morpholino including the sequence of SEQ ID NO: 35. In another example, the kit includes an anti-CD47 antibody or fragment thereof, such as monoclonal antibody MIAP301, monoclonal antibody OX101, or monoclonal antibody B6H12. In a further example, the kit includes a CD47 binding peptide, such as a peptide including the amino acid sequence of SEQ ID NO: 1 or SEQ ID NO: 37. In another example, the kit includes an anti-TSP1 antibody or fragment thereof, such as monoclonal antibody A6.1 or monoclonal antibody C6.7.

The kits may further include additional components such as instructional materials and additional reagents, for example cell culture medium (such as growth medium or differentiation medium) for one or more cell types. In some examples, the kits may include one or more primary cell types (for example, HUVEC). The kits may also include additional components to facilitate the particular application for which the kit is designed (for example tissue culture plates). The instructional materials may be written, in an electronic form (such as a computer diskette or compact disk), or may be visual (such as video files).

The following examples are provided to illustrate certain particular features and/or embodiments. These examples should not be construed to limit the disclosure to the particular features or embodiments described.

EXAMPLES

Example 1

CD47 Inhibits Self-Renewal and Reprogramming by Regulating c-Myc and Other Stem Cell Transcription Factors This example shows that primary cells obtained from CD47- or thrombospondin-1-null mice lack the rapid senescence in culture typically observed for wild type (WT) primary mouse cells, and that the resilience of these null cell primary cultures derives at least in part from enhanced self-renewal and an ability to undergo stem cell reprogramming.

Introduction

CD47 is a signaling receptor for the secreted matricellular protein thrombospondin-1 and the counter-receptor for signal-regulatory protein-α (SIRPα), which on phagocytic cells recognizes CD47 engagement as a marker of self (Matozaki et al., *Trends Cell Biol* 19, 72-80, 2009; Roberts et al., *Matrix Biol.*, 31(3):162-169, 2012; Frazier et al., in *Nature Signaling Gateway*, doi:10.1038/mp.a002870.01, 2010). Mice lacking CD47 or thrombospondin-1 are profoundly resistant to several types of tissue stress including ischemia, ischemia/reperfusion, and high dose irradiation (Roberts et al., *Matrix Biol.*, 31(3):162-169, 2012; Isenberg et al., *Blood* 109, 1945-1952, 2007; Thakar et al., *J Clin Invest* 115, 3451-3459, 2005; Isenberg et al., *Surgery* 144, 752-761, 2008; Isenberg et al., *Am. J. Pathol.* 173, 1100-1112, 2008). The survival advantage of ischemic CD47-null tissues is mediated in part by increased nitric oxide/cGMP signaling 2, but this pathway is not sufficient to account for the resistance to ionizing radiation caused by CD47 blockade (Maxhimer et al., *Sci. Transl. Med.* 1:3ra7, 2009). Radioresistance associated with CD47 blockade is cell autonomous (Id.), indicating that additional pro-survival signaling pathways are controlled by CD47.

Engaging CD47 in some cell types triggers apoptosis or type III programmed cell death (Frazier et al., in *Nature Signaling Gateway*, doi:10.1038/mp.a002870.01, 2010; Bras et al., *Mol Cell Biol* 27, 7073-7088, 2007). BCL2/adenovirus E1B19 kDa protein-interacting protein 3 (BNIP3) is a pro-apoptotic BH3 domain protein that was identified as an interacting partner with the cytoplasmic tail of CD47 and implicated in CD47-dependent cell death (Lamy et al., *J Immunol* 178, 5930-5939, 2007). Furthermore, localization of the dynamin-related protein Drpl is regulated by CD47 ligation and was implicated in the control of mitochondria-dependent death pathways by CD47 (Bras et al., *Mol Cell Biol* 27, 7073-7088, 2007). Drpl mediates mitochondrial fission (Kageyama et al., *Curr Opin Cell Biol* 23, 427-434, 2011). Correspondingly, some tissues in CD47-null and thrombospondin-1-null mice show increased mitochondrial numbers and function (Frazier et al., *Matrix Biol* 30, 154-161, 2011). Although these studies provide some insights into how CD47 ligation can trigger cell death, regulation of mitochondrial function is unlikely to account for the profound resistance to stress conferred by the absence or blockade of CD47 signaling.

In contrast to the above noted survival advantages of cells lacking or expressing decreased levels of CD47, elevated expression of CD47 can confer an indirect survival advantage in vivo. CD47 engages SIRPα on macrophages and prevents phagocytic clearance by conveying a "don't eat me" signal (Matozaki et al., *Trends Cell Biol* 19, 72-80, 2009). Tyrosine residues in the cytoplasmic domain of SIRPα become phosphorylated in response to engaging CD47 and modulate the recruitment and/or activity of several signaling molecules including SHPT, SHP2, SKAP55hom/R, FYB/SLAP-130, and PYK2 (Id.). Thus, erythrocytes lacking CD47 expression are rapidly cleared in vivo (Oldenborg et al., *Science*, 288(5473):2051-2054, 2000). Similarly, elevated expression of CD47 on several types of cancer cells has been shown to inhibit their killing by macrophages or NK cells (Chan et al., *Proc Natl Acad Sci USA*, 106(33):14015-10421, 2009; Kim et al., 2008; Majeti et al., *Cell* 138(2):286-299, 2009). Conversely, CD47 antibodies that block SIRPα binding enhance macrophage-dependent clearance of tumors in several mouse models (Chao et al., *Cancer Res.* 71(4):1374-1384, 2011; Chao et al., *Cell* 142(5):699-713, 2010; Majeti et al., *Cell* 138(2): 286-299, 2009; Willingham et al., *Proc Natl Acad Sci USA*, 109(17):6662-6667, 2012), although others have shown that such clearance can occur independent of inhibitory SIRPα signaling (Zhao et al., *EMBO Rep.* 12(6):534-541, 2011).

Taken together, these studies indicate two opposing roles for CD47 in cell survival. The cell autonomous advantages of decreased CD47 expression, leading to less inhibitory CD47 signaling, must be balanced against the need to maintain sufficient CD47 levels to prevent phagocytic clearance in vivo. Hematopoietic stem cells also exhibit elevated CD47 expression, and high CD47 expression in the stem cell niche was proposed to be important to protect stem cells from innate immune surveillance (Jaiswal et al., *Cell* 138 (2):271-285, 2009).

Methods

Cell Culture and Reagents:

Thrombospondin-1 null (Lawler et al., *J Clin Invest* 101, 982-992, 1998) CD47 null mice (Lindberg et al., *Science* 274, 795-798, 1996) extensively back-crossed onto a C57Bl/6J background and WT mice were maintained in a pathogen-free environment according to protocols approved by the NCI Animal Care and Use Committee. Mouse lung endothelial cells were isolated and their purity verified as described previously (Zhou et al., *Oncogene* 25, 536-545, 2006). These conditions were previously documented to reproducibly yield>95% pure endothelial cells at passage two (CD31+, smooth muscle actin-). Mouse lung endothelial cells were cultured at 37° C. with 5% $CO_2$ using Endothelial Growth Medium-2 (EGM2) (Thermo Scientific Fisher, Inc., Waltham, Mass.). Cell populations from mouse spleens were separated using the Pan T cell Isolation (130-095-130), CD4(L3T4) (130-049-201), CD8a(Ly-2) (130-049-401) CD11b (130-049-601), CD19 microbead kits (130-052-201) (MACS, Miltenyi Biotech Germany).

V6.5 mouse ES cells were cultured on gelatin-coated dishes with mouse embryonic fibroblast (MEF) feeder cells using standard mouse ES medium containing DMEM (high glucose), 15% ES cell-qualified FBS, 200 mM L-glutamine, non-essential amino acids (Life Technologies), Pen/Strep, 0.1 mM 2-mercaptoethanol, and 1000 U/ml leukemia inhibitory factor (LIF).

The thrombospondin-1-derived CD47-binding peptide 7N3 (1102-FIRVVMYEGKK-1112; SEQ ID NO: 1) and a corresponding inactive control peptide 604 (FIRGGMY-EGKK; SEQ ID NO: 2) were synthesized by Peptides International (Louisville, Ky.) (Barazi et al., *J Biol Chem* 277, 42859-42866, 2002). Human TSP1 was purified from the supernatant of thrombin-activated platelets obtained from the NIH Blood Bank as previously described (Roberts et al., *J Tissue Cult Methods* 16, 217-222, 19). A somatic mutant of the Jurkat human T lymphoma cell line lacking CD47, JinB8, was provided by Dr. Eric Brown (Reinhold et al., *Int Immunol* 11:707-718, 1999). Jurkat T cells, JinB8, Raji human Burkitt's lymphoma cells with c-Myc under the control of an IgH enhancer, B16 F10 murine melanoma, and Rat 1 fibroblasts expressing the conditional c-Myc fusion protein (MycER™; Littlewood et al., *Nucleic Acids Res* 23, 1686-1690, 1995) were cultured using RPMI 1640 medium containing 10% FBS, penicillin/streptomycin, and glutamine (Invitrogen, Rockville, Md.).

RNA Extraction and Real Time PCR:

Total RNA was extracted using TRIzol® reagent (Invitrogen, Rockville, Md.) 24-36 hours after transfection or as indicated. Harvested mouse tissues were frozen in liquid nitrogen or placed into RNA Later™ RNA Stabilization Reagent (Ambion, Life Technologies, Grand Island, N.Y.). Whole organs (lungs, spleen, kidney, testis, skeletal muscle, brain, heart, and liver) were homogenized in TRIzol® reagent, and RNA was isolated. cDNA was prepared using First Maxima First Strand cDNA Synthesis kit for RT-qPCR (Fermentas Life Sciences, Glen Burnie, Md.). Real Time PCR was performed using the primers listed herein as SEQ ID NOs: 3-34, and SYBR Green PCR master reaction mix (AB applied Sciences, Life Technologies, Grand Island, N.Y.) on an MJ Research OPTICON I instrument (Bio-Rad) with the following amplification program: 95° C. for 15 minutes, followed by 40 cycles of 95° C. for 15 seconds, 58° C. for 20 seconds, 72° C. for 25 seconds, and 7° C. for 1 minute. Melting curves were performed for each product from 30° C. to 95° C., reading every 0.5° C. with a 6-second dwell time. The fold changes in mRNA expression were calculated by normalizing to hypoxanthine phosphoribosyl-transferase (HPRT1) and TATA-box binding protein associated factor (TAF9) for mouse tissues and endothelial cells, or 13-2 microglobulin (B2M) mRNA levels for spleen and isolated splenocytes. B2M was used for normalization of mRNA levels in human cells. Note that the total RNA yield per cell was higher for all CD47-null and CD47-deficient cells and tissues as compared to WT. Equal amounts of total RNA from WT and CD47 null mouse correspondingly showed differences expression for many housekeeping genes, but the above noted reference genes showed minimal differences in Ct values.

Microarray Processing:

Samples were prepared according to Affymetrix protocols (Affymetrix, Inc.). RNA quality and quantity were ensured using the Bioanalyzer (Agilent Technologies) microfluidics-based platform and NanoDrop (Thermo Fisher Scientific, Inc.) micro-volume spectrophotometer, respectively. Per RNA labeling, 300 nanograms of total RNA was used in conjunction with the Affymetrix recommended protocol for the GeneChip 1.0 ST chips.

The hybridization cocktail containing the fragmented and labeled cDNAs were hybridized to Affymetrix Mouse GeneChip® 1.0 ST chips. The chips were washed and stained by the Affymetrix Fluidics Station using the standard format and protocols as described by Affymetrix. The probe arrays were stained with streptavidin phycoerythrin solution (Molecular Probes, Carlsbad, Calif.) and enhanced by using an antibody solution containing 0.5 mg/mL of biotinylated anti-streptavidin (Vector Laboratories, Burlingame, Calif.). An Affymetrix Gene Chip Scanner 3000 was used to scan the probe arrays. Gene expression intensities were calculated using GeneChip® Command Console® Software (AGCC) and Expression Console™ Software. CEL files generated by the Affymetrix AGCC program were imported in the Partek Genomic Suite software and RMA (Robust Multichip Analysis) normalization, log 2 transformation and probe summarization was performed. Anova pairwise comparisons and PCA (Principle Component Analysis) were performed within Partek Genomic Suite. The GEO accession numbers for the microarray data is GSE43133.

GeneSet Enrichment Analysis (GSEA) was used to test whether an established gene signature was significantly enriched for genes differentially expressed between WT, CD47 null, CD47 null EB-like clusters, and established embryonic stem cell lines. Description of the GeneSet enrichment analysis (GSEA) and the MSigDB can be found at www.broadinstitute.org/gsea/.

Teratoma Formation:

The v6.5 mouse ES cell line was used as a positive control for testing teratoma formation. These mES cells were cultured in DMEM medium containing 15% fetal bovine serum and 1000 IU/ml LIF (Leukemia Inhibitory Factor). For teratoma formation, the mES cells or CD47-/- endothelial cells were trypsinized, washed once in PBS, and finally resuspended in PBS at 5×106/ml for mES and 1×107/ml for CD47-/-. The cells suspension was chilled on ice and then mixed with 50% volume of cold Matrigel (4° C.). The cell-Matrigel mix was draw into a cold 1 ml syringe, and 0.15 ml was quickly injected subcutaneously into NOD.Cg-Prkdcscid Il2rgtmlWjl/SzJ mice near the region where the hind thigh and the abdomen meet. Therefore, about $5\times10^5$ mES cells or $1\times10^6$ CD47-/- cells from EB-like clusters were injected at each site. Two weeks after the injection, the mice were observed daily for tumor growth. When the tumor reached 2 cm in length, the mouse was euthanized, and the tumors were dissected out for morphological observation.

Colony Forming Assay:

Semisolid medium was prepared based on a previous method to quantify embryonic stem cell embryoid body formation (Stenberg et al., *Cytotechnology* 63, 227-237, 2011). Briefly, 1.5% Noble agar was autoclaved in DMEM low glucose medium. Glutamine and 2% FBS serum were added and kept warm at 50° C. A 1.5 ml volume was allowed to solidify in each Petri dish at RT for 15 min. The mouse lung endothelial cells were trypsinized and 200,000 cells/ml were suspended in EGM2 medium. For the top layer, 1.5% agar was diluted to 0.5% with 2×EGM2 medium, and 100 μl per ml cells were added, mixed very quickly, and 1.5 ml was poured on the top of the base agar layer. Fresh EGM2 medium (1.5 ml) was added after 20 days. Colony morphologies were scored after four weeks.

Cell Culture Medium for Macrophage Differentiation:

Mouse L929 cells (a kind gift from Alan Sher, NIH) were grown in DMEM Growth medium (DMEM with high glucose, 10% FBS, 2 mM L-Glutamine, Penicillin-Streptomycin; all from Life Technologies) at 37° C. under 5% $CO_2$ until 100% confluent. Conditioned medium was harvested and stored at -80° C.

CD47 deficient mouse cells were either cultured in the presence of Endothelial Basal Medium-2 (Lonza) or in the presence of 30% L929 conditioned medium in RPMI Growth Medium (RPMI 1640, 10% FBS, 2 mM L-Glutamine, Penicillin-Streptomycin; all from Life Technologies). Cells were cultured for ten days at 37° C. under 5% $CO_2$. The macrophage marker was tested using Flow Cytometry.

Antibodies/Reagents for Flow Cytometry:

Anti-mouse CD11c PE-Cy7, CD11b PE, and B220 PE were all purchased from BD Biosciences (San Jose, Calif.). Anti-mouse Ly-6C eFluor 450, Ly-6G PerCP-Cy5.5, and CD3e FITC were all purchased from eBioscience (San Diego, Calif.). Anti-Mouse Sca-1 PE-Cy5 was a kind donation from Thomas B. Nutman (NIH). Anti-mouse CD14 APC-Cy7, CD31 AlexaFluor647, CD64 APC, and anti-mouse/human Mac-2 PE were purchased from BioLegend (San Diego, Calif.). All flow cytometry antibodies were titrated for optimal performance. Anti-Rat/Anti-Hamster Ig κ compensation particles were purchased from BD Biosciences.

All cells were dislodged by incubating with Versene solution (Life Technologies) and then scraping. They were collected on ice and washed with buffer (PBS with 3% BSA; Life Technologies). All following staining steps were performed on ice and incubated in the dark. After washes buffer was decanted and cells were stained with all antibodies or each florescence minus one control. Compensation beads were used for single color controls, when possible, as directed by the manufacturer. Otherwise, single color controls were made using a mixture of cell. Cells and beads were washed thoroughly prior to acquisition. Data was acquired using a LSRII (BD Biosciences) and BD FACSDiva™ Software. Data was analyzed using FlowJo software (Tree Star, Inc., Ashland, Oreg.).

Cell Culture Medium for Neural Differentiation:

CD47 null mouse lung endothelial cells passaged for six months were seeded into six-well tissue culture plates using basal EBM medium supplemented with FGF2 and EGF (5-20 ng/ml), heparin and gentamycin sulfate. Embryoid bodies appeared after 24-36 hours. The cells were then plated onto non-tissue culture dishes in heparin-free differentiation medium. Neural precursor cells were visible after six days.

Cell Culture Medium for Smooth Muscle Cell Differentiation:

CD47 null mouse lung endothelial cells were plated into six-well tissue culture plates using Smooth Muscle Basal Medium (Lonza) supplemented with PDGF (10 ng/ml) and TGF-β1 (5 ng/ml). The embryoid bodies (EBs) were harvested and transferred to 1% gelatin (Sigma) coated plates. The EBs differentiated into smooth muscle cells after six days. The differentiated smooth muscle cells were stained for smooth muscle actin.

Cell Culture Medium for Hepatocyte Cell Differentiation:

Wild type and CD47 null endothelial cells were grown in DMEM+glutamine+p/s+1% ITS (Invitrogen)+HGF (R&D-20 ng/ml), Oncostatin M (R&D 10 ng/ml), 10 nM dexamethasone (Waco Pure Chemical Industries Ltd, Osaka, Japan) with slight modification of Ishkitiev et al., *J. Breath Res.* 6:017103, 2012. The embryoid bodies were stained for the hepatocyte marker AFP after 36 hours.

Cell Culture Medium for Mesenchymal Cell Differentiation:

The WT and CD47 null endothelial cells were grown in BD Mosaic™ hMSC SF culture medium along with BD Mosaic™ hMSC SF supplement (BD Biosciences). CD47 null cells formed embryoid bodies after 36 hours. The embryoid bodies were collected and differentiated by coating plates with BD Mosaic™ hMSC SF surface (BD Biosciences). For direct transdifferentiation, the plates were coated with BD Mosaic™ hMSC SF surface according to manufacturer's instructions. WT and CD47 null endothelial cells were directly plated on coated 6-well plates (BD biosciences). The trans-differentiated cells were stained using oil red after 10-days.

Oil Red O Staining for Mesenchymal Adipocytes:

Stock solution of Oil Red O (300 mg of oil red powder+100 ml of isopropanol) was prepared the day before staining according to the manufacturer's instructions. For a working solution, 3 parts of stock solution of Oil Red O and 2 parts of deionized water were mixed. The working solution was incubated for 10 minutes at RT and filtered with Whatman filter paper several times. The differentiated embryoid cells were cultured in 12-well plates for 10-days. To assess adipogenic phenotype, cells were washed with 1×DPBS and fixed with 1-2% Formalin overnight at 4° C. The formalin was removed from the wells, and the cells were washed with deionized water. Two ml of 60% of isopropanol was added to each well for 5 minutes. The cells were then incubated with 2 ml of Oil Red O solution for 5 minutes. The cells were rinsed with deionized water until clear. A 2 ml volume of hematoxylin stain was added for 1 minute and then washed with water immediately. The wells were covered with water, and images were taken using phase contrast illumination.

Immunostaining of Embryoid Bodies and Differentiated Cells:

EBs were placed on poly-D lysine coated Lab-Tek cover glass chambers and fixed with 4% paraformaldehyde for five minutes. EBs were gently washed with 1×PBS and permeabilized using 0.3% Triton X-100. The EBs were washed and blocked with 3% BSA for one hour. Primary SOX2 (Abcam) and nestin antibodies (Covance) (1:500) were used for immunostaining.

Differentiated neural cells were cultured overnight using Lab-Tek cover glass 4-well chambers. The cells were washed twice with 1×PBS, fixed using 4% paraformaldehyde for 5 min, and washed three times. The cells were permeabilized using 0.3% Triton X-100 in PBS. The cells were washed three times 5 minutes each and blocked with 5% BSA for one hour. Primary antibodies against GFAP (DAKO), S100b (Abcam), MAP2, beta tubulin III and smooth muscle actin (Sigma) were used. Secondary antibodies (Alexa Fluor® 488 Goat Anti-Mouse IgG1 or Alexa Fluor® 488 Goat Anti-Rabbit IgG, Invitrogen) were used. Confocal images were captured using Zeiss 710 Zeiss AIM software on a Zeiss LSM 710 Confocal system (Carl Zeiss Inc., Thornwood, N.Y.) with a Zeiss Axiovert 100M inverted microscope and 50 mW argon UV laser tuned to 364 nm, a 25 mW Argon visible laser tuned to 488 nm and a 1 mW HeNe laser tuned to 543 nm. A 63× Plan-Neofluar 1.4 NA oil immersion objective was used at various digital zoom settings.

Immunostaining and Differentiation of Cystic Embryoid Bodies:

CD47 null cell embryoid bodies were collected and transferred to gelatin coated T185 flask (Nunc) using RPMI complete media for 6 days. The embryoid bodies differentiated into heterogeneous colonies. The individual colonies were picked and transferred further into gelatin coated Willico dish. The colonies were cultured using appropriate differentiation media (neural smooth muscle, and hepatocyte) for 36 hours. The embryoid bodies were fixed with 4% PFA for 1-2 h at RT. The embryoid bodies were washed three times with 1×PBS (without Ca and Mg ions). The embryoid bodies were blocked with blocking buffer (3% BSA in PBS+0.2% Triton® X-100) for 1-2 hours. The primary antibodies (1:100 in blocking buffer) for neural (ectoderm), smooth muscle actin (mesoderm) and Alpha-fetoprotein (endoderm) markers used overnight at 4° C. The embryoid bodies were washed with blocking buffer three times. Secondary antibodies (1:1000 ratios of Alexa Fluor® 488 Goat Anti-Mouse IgG1 or Alexa Fluor® 488 Goat Anti-Rabbit IgG, Invitrogen) were used. The embryoid bodies were washed three times with 1×PBS. Embryoid bodies were dried using Kimwipes. VECTASHIELD from Vector Laboratories (Burlingame, Calif.) with DAPI used for mounting. The confocal images were captured using Zeiss 710 Zeiss AIM software on a Zeiss LSM 710 Confocal system as above mentioned. The Z-stack images were captured and exported as an Avi File using the ZEN software.

Sox2 Immunohistochemistry:

Lung and spleen tissues from WT and CD47−/− mice were fixed in 10% formalin. Tissue was paraffin embedded and cut into 5 μm thick sections. Immunostaining was performed using an antibody to SOX2 (1:100) or a non-specific control antibody and detected using the DAKO LASB Universal Kit. Stained sections were visualized and photographed under light microscope using the Q-Imaging system.

Western Blots

Equal number of lung endothelial cells from WT and CD47 null were plated in six-well plates overnight. Cell lysates were made from washed cells using NP-40 lysis buffer (50 mM Tris pH 8.0, 150 mM NaCl and 1% NP-40 along with ProteoBlock Protease inhibitor Cocktail (Fermentas, Glen Burnie, Md.). The lysates were centrifuged, and equal volumes of supernatant were boiled with 4× NuPAGE-LDS sample buffer (Invitrogen, Rockville, Md.) for 5 minutes at 95° C. Proteins were separated using 4-12% Bis-Tris gels (Invitrogen). N-terminal c-Myc antibody (Epitomics Inc., Burlingame, Calif.) was used at 1:1000 to perform western blots. Secondary anti-rabbit IgG conjugated to HRP was used at 1:5000. Super Signal West Pico chemiluminescent substrate (Thermo Scientific Fisher, Rockford) was used to detect bound antibodies. For protein normalization, the blots were stripped and reprobed using a β-actin antibody (Sigma Aldrich, St. Louis, Mo.).

Undifferentiated EBs were cultured in either complete RPMI or serum-free media with neural growth factors for 10-15 days. Similarly, lung endothelial cells from WT and CD47-null were plated for 10-15 days with EGM2 medium at 37° C. The endothelial cells and differentiated EBs were washed with 1×PBS, and cell lysates were made using RIPA buffer. The lysates were centrifuged, and equal volumes of supernatant were boiled with 4×NuPAGE-LDS sample buffer (Invitrogen) for 5 min at 95° C. Proteins were separated using 4-12% or 12% Bis-Tris gels (Invitrogen). Primary SOX2 (Abcam, Cambridge, Mass.), nestin (Covance, Princeton, N.J.; 1:500), KLF4, OCT4, SOX2 (Stemgent, Cambridge, Mass.), Tuj 1 (Neuron-specific class III beta-tubulin, Neuromics, Edina, Minn.), GFAP (DAKO, Carpinteria, Calif.) smooth muscle actin (Sigma-Aldrich, St. Louis, Mo.), and AFP (Cell Signaling, Danvers, Mass.) antibodies were used at 1:1000 to perform Western blots. Secondary anti-rabbit IgG or anti-mouse IgG conjugated to HRP were used at 1:5000. Super Signal West Pico chemiluminescent substrate (Thermo Scientific Fisher) was used to detect bound antibodies. For protein normalization, the blots were reprobed using a β-actin antibody (Sigma-Aldrich).

Single Cell Differentiation:

EB-like clusters were formed using serum free EBM media for 36 hour. A single EB-like cluster was dissociated in to single cell suspension using ACCUTASE™ (BD Biosciences) cell detachment solution and was plated at limiting dilution into 96-well plates and assessed for colony formation over 7 days. A colony was picked, expanded and plated further in to 4-Well LabTek Chambers using neural, smooth muscle and hepatocytes growth media. After 7 days, the cells were stained with antibodies against TUJI (ectoderm), smooth muscle actin (mesoderm), and AFP (endoderm). WT murine lung endothelial cells were also cultured under the same conditions but were unable to differentiate and were negative for these markers.

BrdU Staining for Asymmetric Cell Division:

Asymmetric cell division was analyzed as described with slight modifications. WT and CD47 null cells (passage 1) were labeled with BrdU (1 uM) for 5 days and then chased in BrdU-free medium for 24 h and followed by cytochalasin B at 2 μM for 24 hours. The BrdU labeled cells were fixed with 70% ethanol for 30 min. The cells were denatured with 2N HCl/0.5% Triton X-100 for 60 min. The cells were washed in PBS/0.5% TX-100/0.1% BSA. The cells were stained with mouse-anti-BrdU (Calbiochem) using a dilution of 1:100 overnight at 4° C. Secondary antibodies donkey-anti-mouse IgG-Alexa 594 or Alexa 488 (Invitrogen) were used (1:500) for 1 hour at RT. The cells were mounted using VECTASHIELD (Vector Laboratories). Images were acquired at 40× using an Olympus microscope. The total cells negative for BrdU and positive for DAPI were counted manually.

Continuous growing CD47-null cells were labeled with BrdU for 10 days. One hundred percent BrdU incorporation was confirmed using immunofluorescent detection of nuclear BrdU labeling with confocal microscopy. The BrdU labeled cells were chased for 2 consecutive cell divisions in BrdU-free medium (72 hours). The mitotic cells were obtained by gently shaking the flask. The mitotic cells were plated in glass bottom Micro Well dishes (MatTek Corporation) along with cytochalasin B for 24 hours. The cells formed EB like clusters and were stained with BrdU antibody and green fluorescent phalloidin conjugate. Images were captured using a Zeiss 780K confocal microscopy at 63×.

Transient CD47 Re- or Over-Expression:

Isolated mouse lung endothelial cells, Raji Burkitt's lymphoma cells, B16 melanoma cells, and Myc null Rat 1 fibroblast cells were plated overnight in six-well plates. The cells were transfected with CD47-FLAG expression plasmid (Kaur et al., J Biol Chem 286, 14991-15002, 2011) and/or human c-Myc-GFP plasmid (manuscript in preparation). The cells were transfected using Opti-MEM® I Reduced Serum Medium (Invitrogen) and the FuGENE® HD Transfection kit (Roche). The serum free medium was replaced with complete RPMI medium five hours after transfection. The cells were analyzed at 24-36 hours post transfection. The supernatants were analyzed for lactate dehydrogenase (LDH) release using CytoTox 96® Non-Radioactive Cytotoxicity Assay (Promega Corporation, Madison, Wis., USA).

JINB8 cells were transfected with CD47-V5 construct using Amaxa™ Nucleofector™ (Lonza) non-viral transfection technology. The transfection efficiency was determined by flow Cytometry. The CD47-V5 transfected cells were purified using magnetic beads bound with human CD47 antibody (B6H12). The transfected cells were loaded onto MACS column which was placed in the magnetic field of a MACS® separator (Miltenyi Biotec). The magnetic bead labeled CD47$^+$ cells were retained on the column. The unlabeled cells ran through and were depleted from CD47$^+$ cells. After removal of the column, the CD47$^+$ cells bound to magnetic beads were eluted. The pure population of CD47$^+$ cells was stably cultured using G418 (250 μg/ml). The pure population of CD47$^+$ and Jurkat cells were centrifuged and re-suspended in RPMI with 1% FBS at $10^6$ cells/ml. Cells were plated in 12 well plates and treated with 1 μg/ml (2.2 nM) thrombospondin-1, and total RNA was isolated using TRIzol®. The relative gene expression of c-MYC was measured using GAPDH as a control.

CD47 Knockdown in T Cells and in WT Mice:

A translation-blocking antisense morpholino oligonucleotide complementary to human and murine CD47 (CGTCACAGGCAGGACCCACTGCCCA; SEQ ID NO: 35) and a 5-base mismatch control morpholino (CGTgACAGcCAcGACCgACTGCgCA; SEQ ID NO: 36) were obtained from GeneTools, LLC (Philomath, Oreg.) as previously described (Isenberg et al., Circ Res 100, 712-720, 2007). Primary T cells isolated from c-Myc EGFP knock-in mouse were transfected using morpholinos (2.5 μM) along with Endoporter (GeneTools, LLC) delivery reagent according to manufacturer's instructions. Mice were treated by injection of 750 μl of 10 μM morpholino in saline as described (Maxhimer et al., Sci. Transl. Med. 1, 3ra7, 2009). Organs were harvested for mRNA isolation after 48 hours.

Modulation of Stem Cell Transcription Factors by Thrombospondin-1:

Jurkat and JinB8 cells were centrifuged and re-suspended in RPMI+1% FBS at $10^6$ cells/ml. Cells were plated in 12 well plates and treated with 1 μg/ml (2.2 nM) TSP1 using the indicated times and concentrations, and total RNA was isolated using TRIzol® reagent.

Cell Proliferation Assays:

Equal numbers of mouse lung endothelial cells from WT and CD47 (Passage 1) were plated in 96 well plates using RPMI+1% FBS. After 72 hours, net cell proliferation was assessed by the increase in formazan absorbance versus controls assessed at time 0 using Cell Titer 96R aqueous MTS kit (Promega, Madison, Wis.). DNA synthesis was measured using a BrdU Assay (EMD Biosciences, Billerica, Mass.).

Senescence-Associated β-Galactosidase Assay:

Senescent cells were detected in WT and CD47 null lung endothelial cells (Passage 3) by histological staining for a senescence-associated β-galactosidase (Debacq-Chainiaux et al., *Nat Protoc* 4, 1798-1806, 2009). The cells were dried, and images were taken using a phase contrast objective. The positive cell number was expressed as a percentage of the total cells.

Statistical Analysis:

Two-way ANOVA with replication was used for analyzing real time PCR. Student t-test was used for cell proliferation, cell cytotoxicity and senescence cell assays, which were performed in triplicate. All results are presented as mean±SD.

Results

Figure 1A:
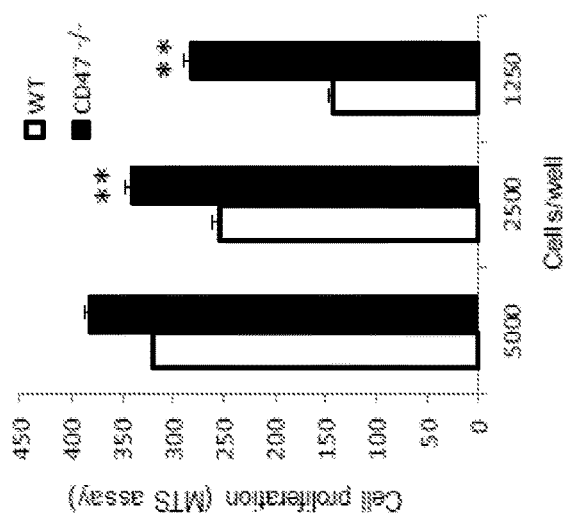
Figure 8C:
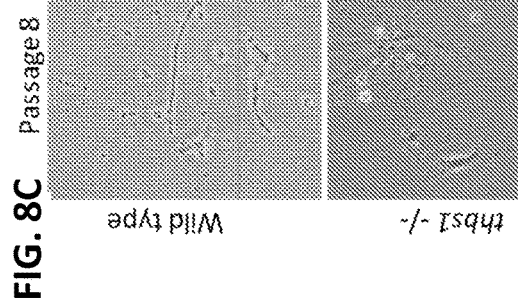
FIGS. 8A-D show continuous propagation of WT and CD47-null mouse lung endothelial cells.
Figure 8D:
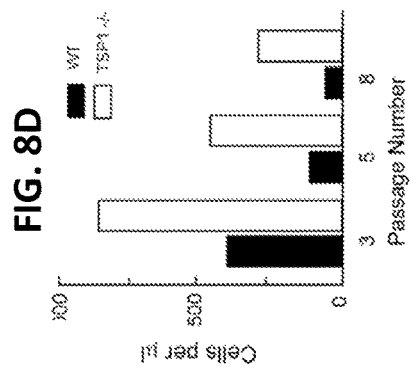
Figure 8A:
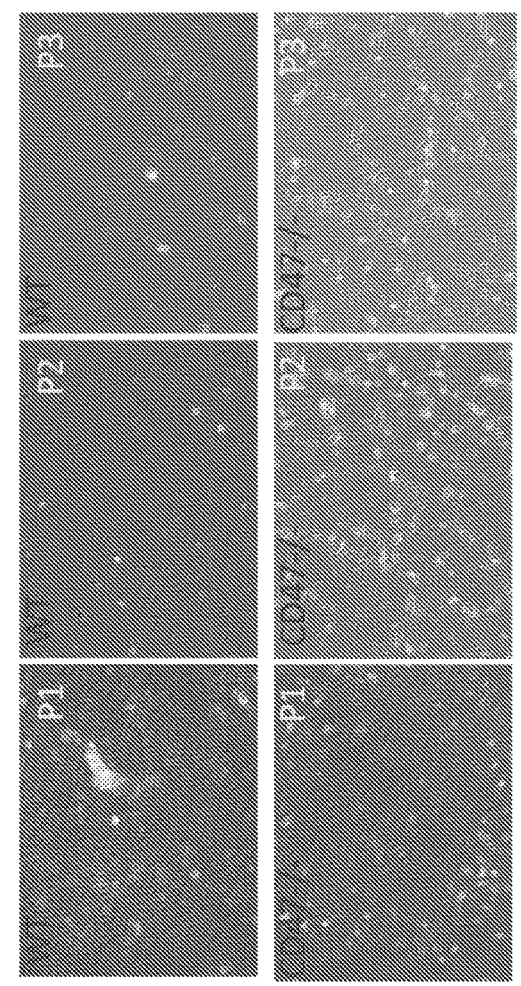
Figure 8B:
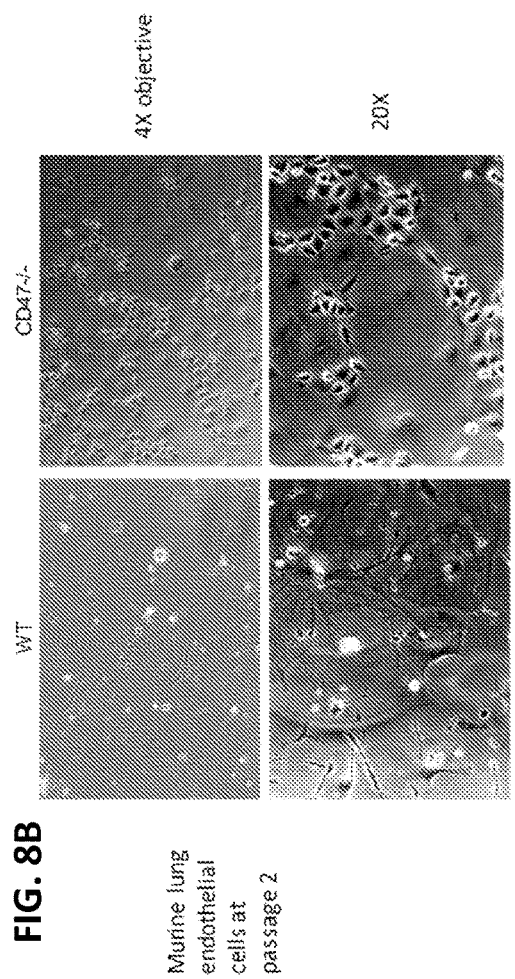

Loss of CD47 Allows Self-Renewal with Increased c-Myc Expression:

Primary cells isolated from CD47-null mice exhibit a remarkable advantage in adapting to the stress of tissue culture. Lung endothelial cells isolated from WT C57Bl/6 mice had limited survival and proliferative capacities in primary culture as assessed by reduction of [3-(4,5-dimethylthiazol-2-yl)-5-(3-carboxymethoxyphenyl)-2-(4-sulfophenyl)-2H-tetrazolium (MTS) and bromodeoxyuridine incorporation (FIGS. 1A, B) and rapidly became senescent upon passage (FIG. 8A). In contrast, CD47-null lung endothelial cells at first passage showed enhanced plating efficiency and proliferation at several cell densities (FIGS. 1A, B). Upon repeated passage, WT primary cells became flattened and vacuolated, whereas the CD47-null endothelial cells consistently maintained a well-differentiated cobblestone morphology for several months in continuous culture (FIG. 8B). Continuously proliferating cell lines were reproducibly obtained when primary CD47-null cells were repeatedly passaged but were rarely obtained from WT cultures. Similar enhanced cell culture potential was observed in CD47 null dermal papillary cells compared to wild type cells. The CD47-null cells generally lacked expression of the senescence-associated acidic β-galactosidase marker (Kurz et al., *J. Cell Sci.* 113:3613-3622, 2000) that rapidly appeared in the WT cells (FIG. 1C). High frequency generation of continuously proliferating cell lines was also observed for vascular smooth muscle cells and CD3$^+$ T cells isolated from CD47-null mice and for lung endothelial cells cultured from mice lacking the CD47 ligand thrombospondin-1 (FIGS. 8C, D).

Figure 2E:
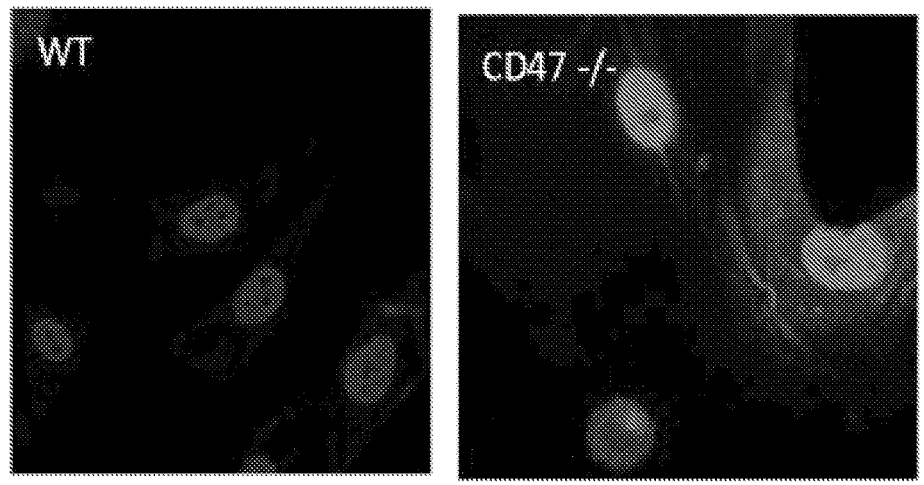
Figure 2F:
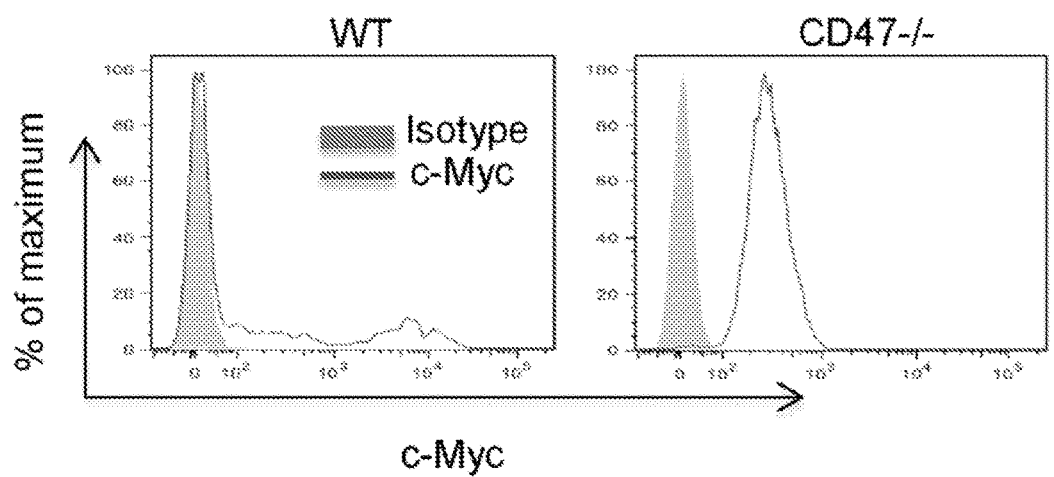
Figure 3A:
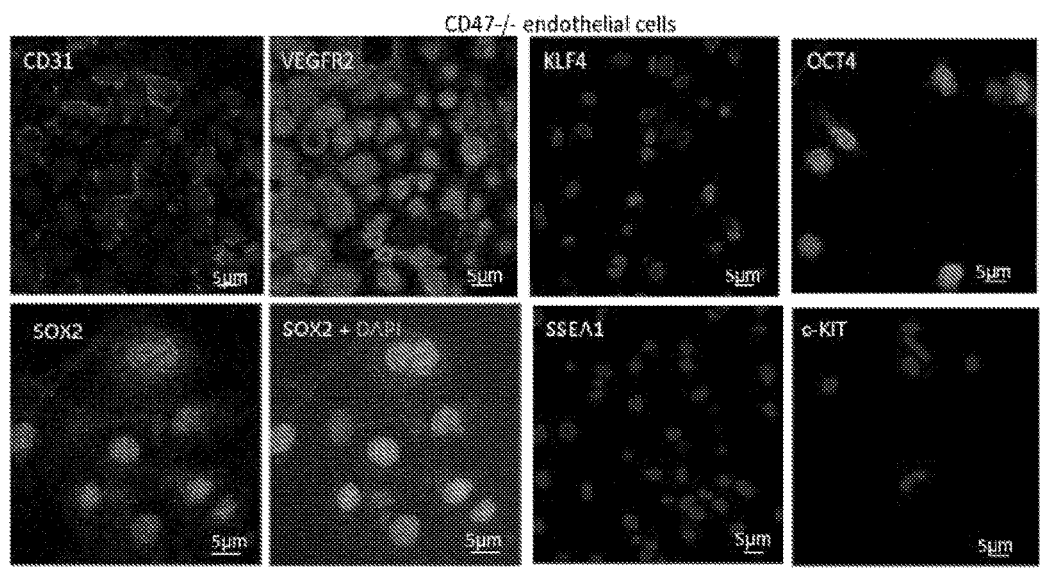

The ability of CD47-null and thrombospondin-1-null cells to continuously proliferate could reflect either increased escape from senescence or induction of a self-renewing stem cell phenotype. Several genes have been identified that enable primary cells to escape senescence and become immortalized including p53, Rb, p16-INK4A, and c-Myc (Wang et al., *Cell Cycle* 10:57-67, 2011). Of these, only c-Myc mRNA levels were significantly elevated relative to HPRT1 mRNA levels in the primary cell cultures and remained elevated upon repeated passage (FIGS. 2A, B). Protein levels for c-Myc were also elevated in primary CD47-null lung endothelial cells as detected by Western blotting (FIGS. 2C and 3E), immunofluorescence (FIG. 2E), and flow cytometry (FIG. 2F). Most c-Myc was nuclear, but filamentous cytoplasmic staining was also noted in the CD47-null cells, consistent with known association of c-Myc with microtubules (Alexandrova et al., *Mol. Cell Biol.* 15:5188-5195, 1995). Characteristic of a pure endothelial cell culture, the continuously growing CD47-null cells uniformly expressed VEGFR2 and heterogeneously expressed CD31 (Pusztaszeri et al., *J. Histochem. Cytochem.* 54:385-395, 2006) (FIG. 3A). Absence of vascular smooth muscle cell contamination was indicated by the lack of detectable α-smooth muscle actin expression, although this was detectable at low levels in WT endothelial cell cultures (FIG. 3E).

CD47 Coordinately Regulates Stem Cell Transcription Factors:

Because elevated c-Myc expression also promotes self-renewal of stem cells (Kim et al., *Proc. Natl. Acad. Sci. USA* 108:4876-4881, 2011) and is necessary under some conditions for embryonic stem cell self-renewal (Varlakhanova et al., *Differentiation* 80:9-19, 2010), we examined the expression of additional transcription factors that support stem cell reprogramming (Okita and Yamanaka, *Philos. Trans. R. Soc. Lond. B Biol. Sci.* 366:2198-2207, 2011) and found significant elevation of mRNA for Sox2, Klf4, and Oct4 and the stem cell marker nestin in primary CD47-null endothelial cells (FIG. 2D). Oct4 protein expression was detected by immunofluorescence in a majority of the CD47 null cells, but not in WT cells (FIG. 3A). Sox2 and Klf4 were detectable in a subset of CD47-null cells, whereas Klf4, Oct4, and c-Myc were undetectable by immunofluorescence in WT endothelial cells and Sox2 positive cells were rarely seen (FIG. 3A). Some Sox2 staining in CD47 null cells was cytoplasmic, consistent with its reported subcellular localization in early embryonic cells (Keramari et al., *PLoS One* 5:e13952, 2010), but the majority of staining was nuclear. Western blotting confirmed elevated Klf4 and Oct4 levels in CD47-null versus WT endothelial cells (FIG. 3E). Flow cytometry also confirmed increased Oct4 expression in CD47-null cells (FIG. 3F).

These data suggested that CD47-null endothelial cell cultures contain a larger fraction of stem cells, which characteristically exhibit asymmetric cell division (Sundaraman et al., *Circ. Res.* 110:1169-1173, 2012; Pine et al., *Proc. Natl. Acad. Sci. USA* 107:2195-2200, 2010). The frequency of asymmetric division was examined in WT and CD47-null endothelial cell cultures uniformly labeled using BrdU by chasing with unlabeled medium for 24 hours in the presence of cytochalasin B to inhibit cytokinesis. Asymmetric division was indicated by adjacent DAPI+ nuclei where only one cell retained BrdU staining (FIG. 3G, upper panel). Such cells were significantly more abundant in the CD47-null cultures (FIG. 3G, lower panel).

Figure 3B:
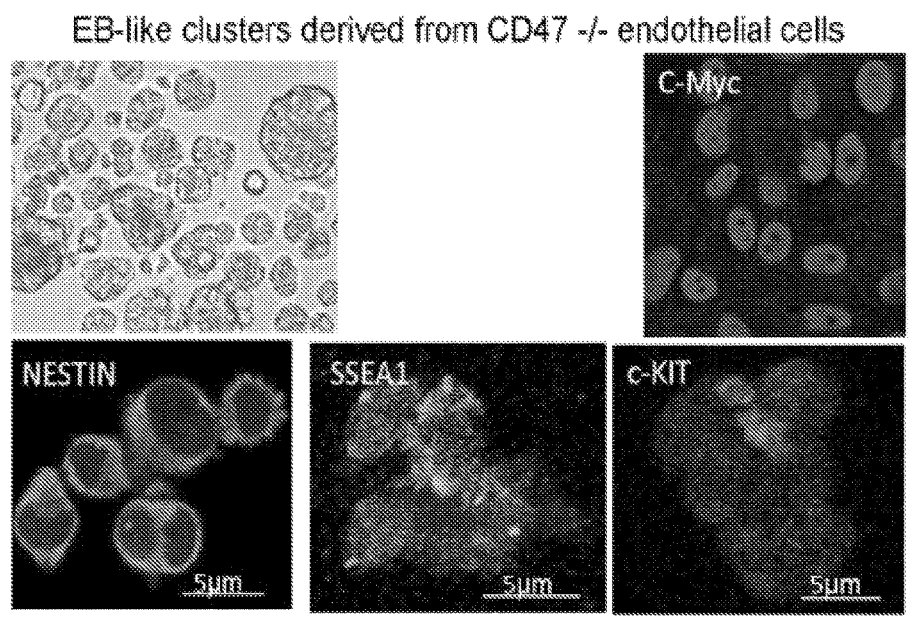
Figure 3H:
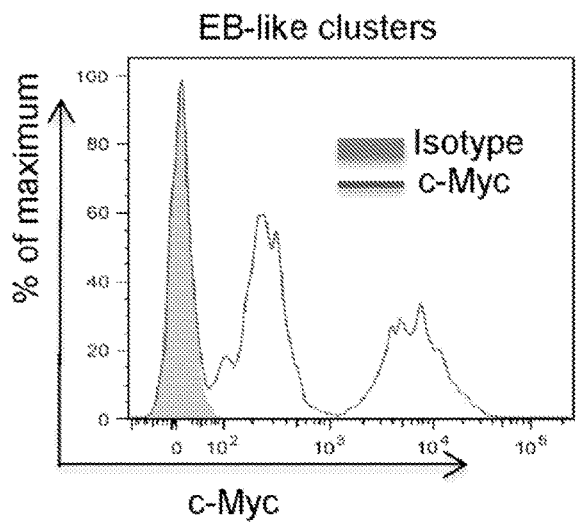
Figure 3I:
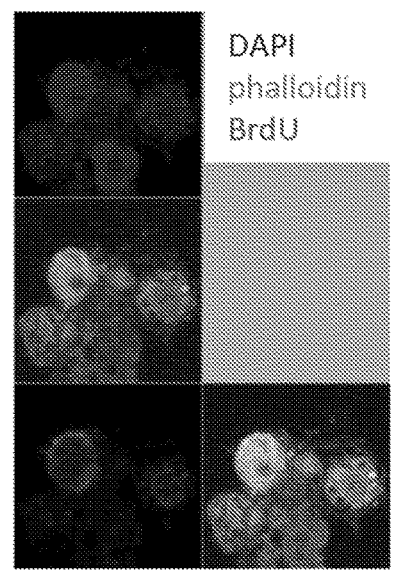

Efficient Cystic Embryoid Body Formation by CD47-Null Cells:

Ectopic expression of Klf4, Sox2, Oct4, and c-Myc, or ALK2 bearing an activating mutation, in human umbilical vein endothelial cells enables efficient generation of multipotent or induced pluripotent stem (iPS) cells (Panopoulos et al., *PLoS One* 6:e19743, 2011; Medici et al., *Nature Med.* 16:1400-1406, 2010), suggesting that self-renewal of the CD47-null endothelial cells might arise from increased numbers of stem cells in these cultures. Examination of characteristic stem cell markers revealed that continuously propagated CD47-null endothelial cells expressed Sca-1, and 24% of the cells were CD14$^+$/CD11$^+$ (FIGS. 3C and D), which are characteristic markers for endothelial precursor cells (Rehman et al., *Circulation* 107:1164-1169, 2003). However, CD47-null endothelial cells did not express detectable levels of the pluripotency marker SSEA-1 or the stem cell marker c-Kit (FIG. 3A). Because elevated expression of c-Myc, Sox2, Oct4 and Klf4 in some types of primary cells is sufficient to induce cystic EB formation (Itskovitz-Eldor et al., *Mol. Med.* 6:88-95, 2000), we examined whether loss of CD47 circumvents the need to artificially elevate these factors for inducing EBs. Indeed, transfer of primary CD47-null endothelial cells or CD47-null cells grown continuously for 6 months into serum-free medium in the absence of any feeder cells within 2 days induced efficient formation of floated cell aggregates that resembled EBs and continued to proliferate in this state (FIGS. 3B, 9A and B). These were never observed when WT endothelial cells were placed into the same medium, and WT cells did not survive in serum-free media. Cells in the EB-like clusters exhibited strong nuclear c-Myc staining by immunofluorescence (FIG. 3B) and flow cytometry indicated a subpopulation with stronger c-Myc expression than that observed in primary CD47-null endothelial cultures (compare FIG. 3H and FIG. 2F). Unlike CD47-null cells in endothelial cell medium, cells in the EB-like clusters expressed additional stem cell markers including alkaline phosphatase, nestin, SSEA-1 and c-Kit (FIGS. 3B, 10A-H). Consistent with their expression of stem cell markers, cells in EB-like clusters frequently exhibited asymmetric cell division (FIG. 3I).

Figure 3J:
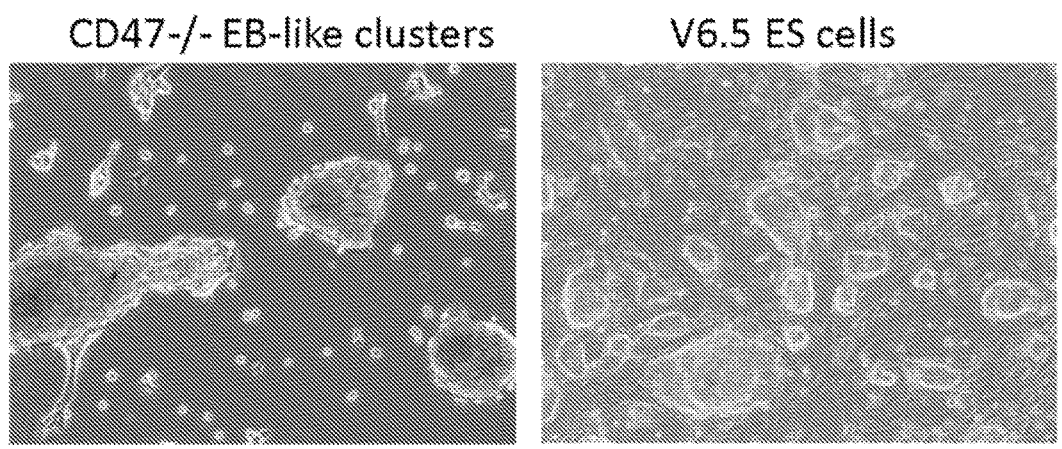
Figure 3K:
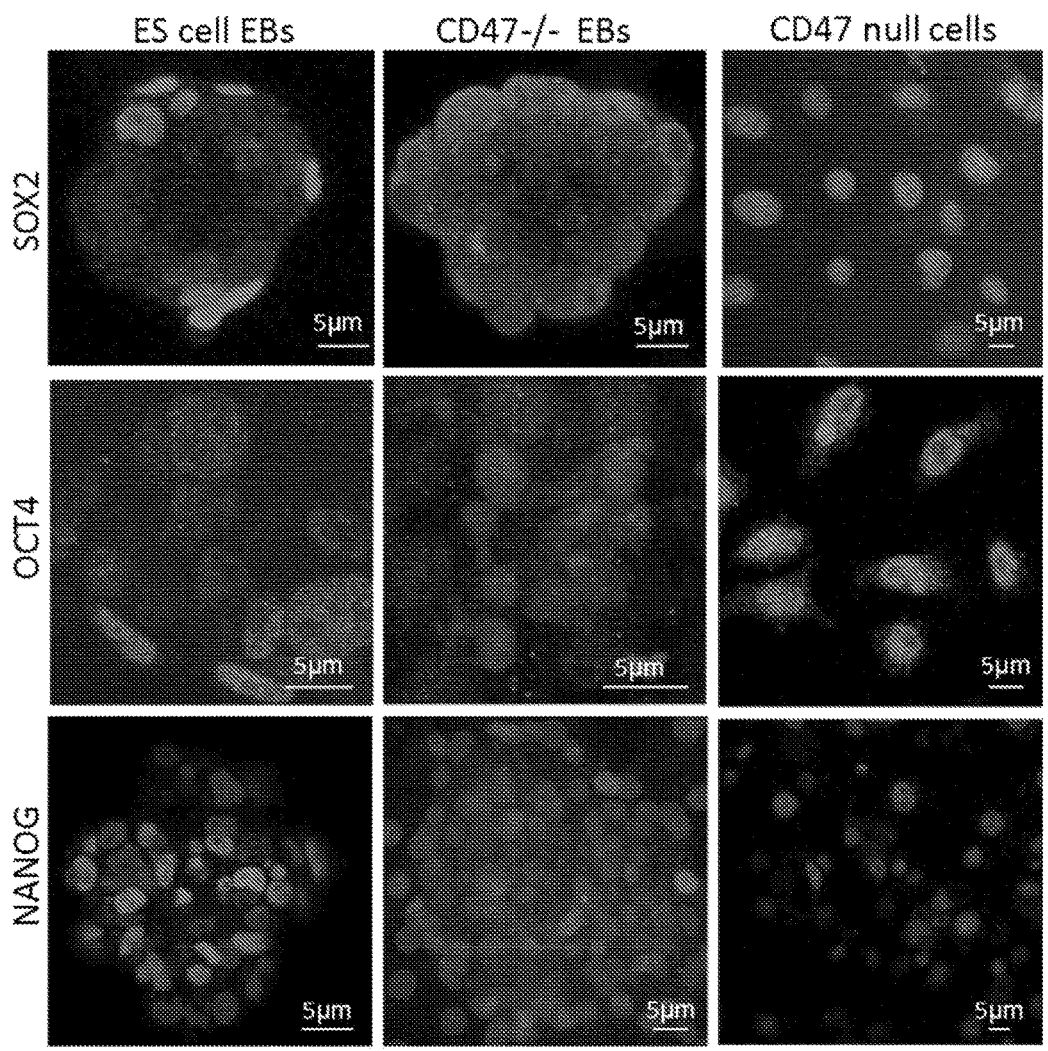

CD47-null cells were grown without feeder cells in ES medium containing LIF adopted colony morphologies similar to V6.5 mouse ES cells grown in the same medium with MEF feeder cells (FIG. 3J). Immunohistochemical analysis of these cells in ES medium demonstrated that CD47-null and V6.5 ES cells contained similar subpopulations that expressed elevated levels of nuclear Oct4, Sox2, and Nanog (FIG. 3K).

Figure 23B:
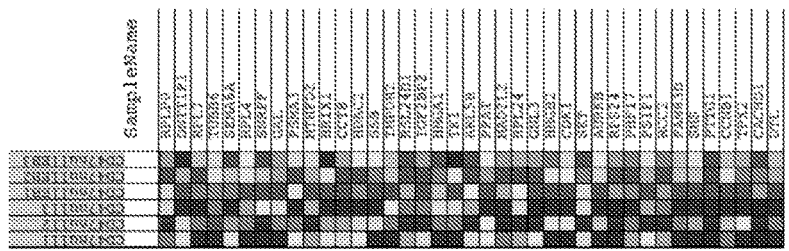
FIG. 23B shows GeneSet Enrichment Analysis (GSEA) for ES cell genes as defined by Bhattacharya et al. (*Blood* 103:2956-2964, 2004) that are induced when CD47 null endothelial cells are induced to form EB-like clusters.
Figure 23A:
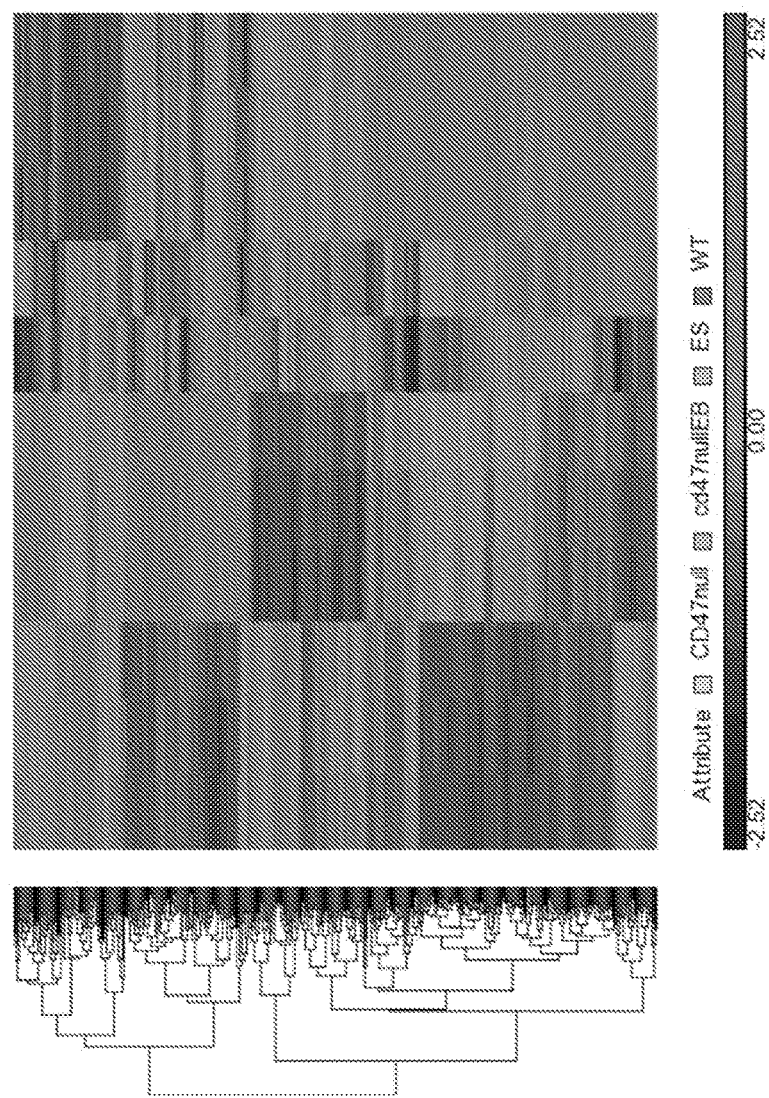
FIG. 23A is a hierarchical cluster analysis of microarray data comparing gene expression of WT and CD47-null endothelial cells, EB-like clusters derived from CD47-null endothelial cells by culture in serum-free medium for 36 hours, and V6.5 ES cells.

Microarray analyses (GEO accession number GSE43133) were performed to globally assess the stem cell character of CD47-null endothelial cells and EB-like clusters derived by culture in serum-free medium for 36 hours. A global principal component analysis revealed that CD47 null endothelial cells and EB-like clusters derived from them clustered near published iPS and ES cells, whereas WT cells did not. To characterize the changes in gene expression that accompany EB-like cluster formation in the CD47 null cells, we compared global gene expression in CD47 null EB-like clusters to that of CD47-null cells before removal of serum and endothelial growth factors and found 383 genes with significant changes. Of these, 255 clustered with genes that showed similar up- or down-regulation in the V6.5 ES cells (FIG. 23A). A GeneSet enrichment analysis (GSEA) identified 39 of these up-regulated genes that are included in the molecular signature for human ES cells defined by Bhattacharya et al. (*Blood* 103:2956-2964, 2004; FIG. 23B). The remaining genes included endothelial-specific genes that were significantly down-regulated (e.g., thrombomodulin) and epithelial/mesenchymal transition genes that were induced when CD47-null cells formed EB-like clusters. Notably, expression of Kdr, which encodes VEGFR2, decreased 10-fold, consistent with loss of VEGFR2 immunoreactivity in the CD47-null EB-like clusters.

Deletion of CD47 Permits Efficient Reprogramming:

To determine whether CD47-null EB-like clusters are competent to give rise to the three germ layers, 6 day-old undifferentiated EB-like clusters were plated on gelatin-coated Willico-dishes for 36 hours containing neural, smooth muscle, or hepatocyte differentiation media (FIGS. 4A-C). Appearance of cells expressing smooth muscle actin indicated mesoderm differentiation (FIG. 4A). Cells expressing neuron-specific βIII tubulin and glial fibrillary acidic protein (GFAP) indicated ectoderm differentiation (FIG. 4B). Cells expressing α-fetoprotein (AFP) indicated endoderm differentiation (FIG. 4C). Because each lineage could arise from different lineage-committed stem cells in the EB-like clusters, we expanded a single clone from CD47-null EB-like clusters and repeated the above differentiation study. Again, cells expressing characteristic markers of the three embryonic lineages were obtained (FIGS. 4D-F). Therefore, the CD47-null cells are multipotent.

Morphological differentiation of EBs provides another in vitro assessment of pluripotency (Sheridan et al., *Stem Cells Int.* 2012:738910, 2012). Differentiation of EB-like clusters in complete RPMI medium for 10-15 days resulted in morphological differentiation characteristic of all three embryonic germ layers (FIGS. 11A-G). Differentiation was accompanied by a loss of SSEA1 expression and decreased expression of other stem cell markers (not shown).

These results suggested that CD47-null EB-like clusters contain pluripotent cells. However, limited fibrotic responses and no teratoma formation was observed when CD47-null EB-like clusters were injected into NOD.Cg-Prkdcscid Il2rgtmlWjl/SzJ mice under conditions where v6.5 ES cells formed teratomas. Therefore, the CD47-null EB-like clusters may not be fully pluripotent. Alternatively, teratoma formation may have been prevented by SIRP-dependent clearance of the CD47-null cells.

Figure 12A:
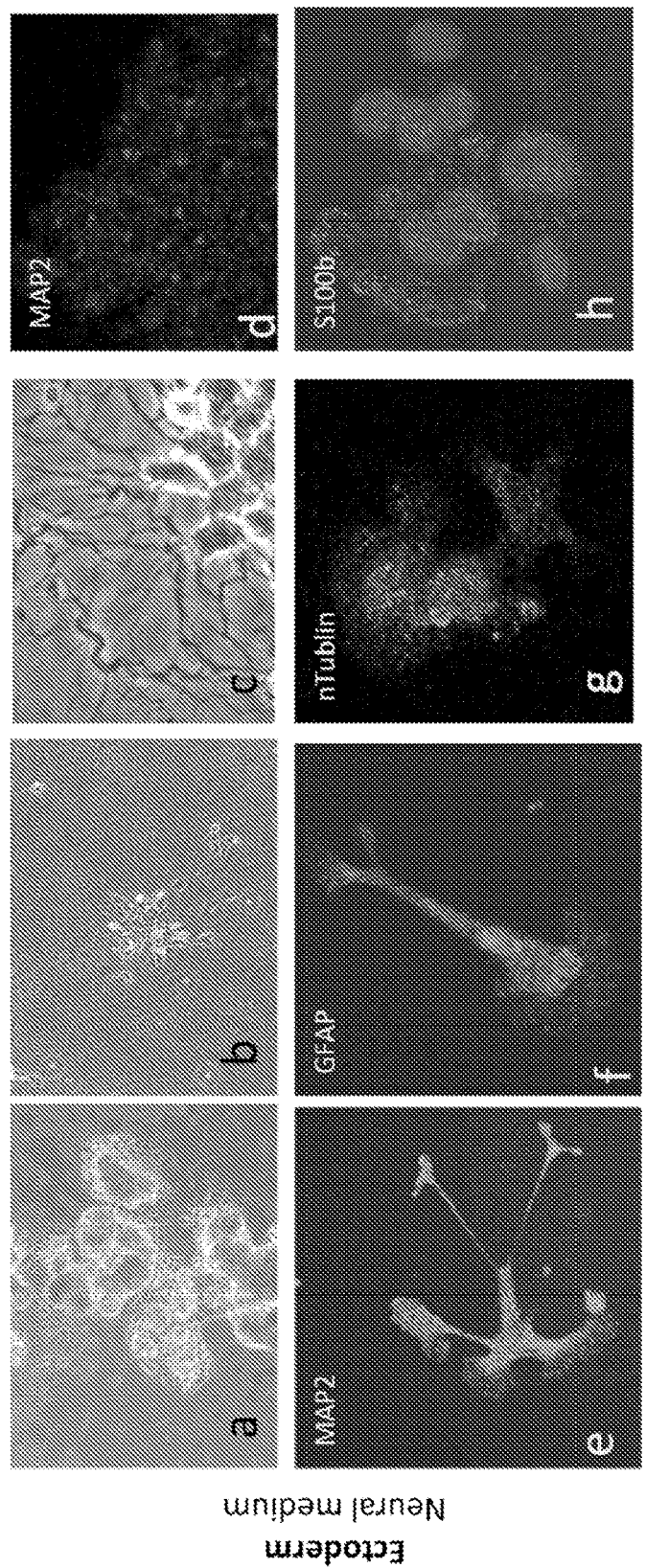
FIGS. 12A-C is a series of digital images of differentiation marker expression in cells derived from CD47-null embryoid bodies.

Further evidence for multipotency was obtained when differentiated CD47-null EBs were dispersed and cultured in neural medium on a gelatin coated substrate (FIG. 12A). Ectodermal differentiation was indicated by expression of the neuronal markers MAP2, glial fibrillary acidic protein (GFAP), neuron-specific beta III tubulin, and the astrocyte marker S100b respectively (FIG. 12A panels d-h). Some non-adherent colonies formed from these cells exhibited extensive neurite formation (FIG. 12A panels a-c).

Figure 12B:
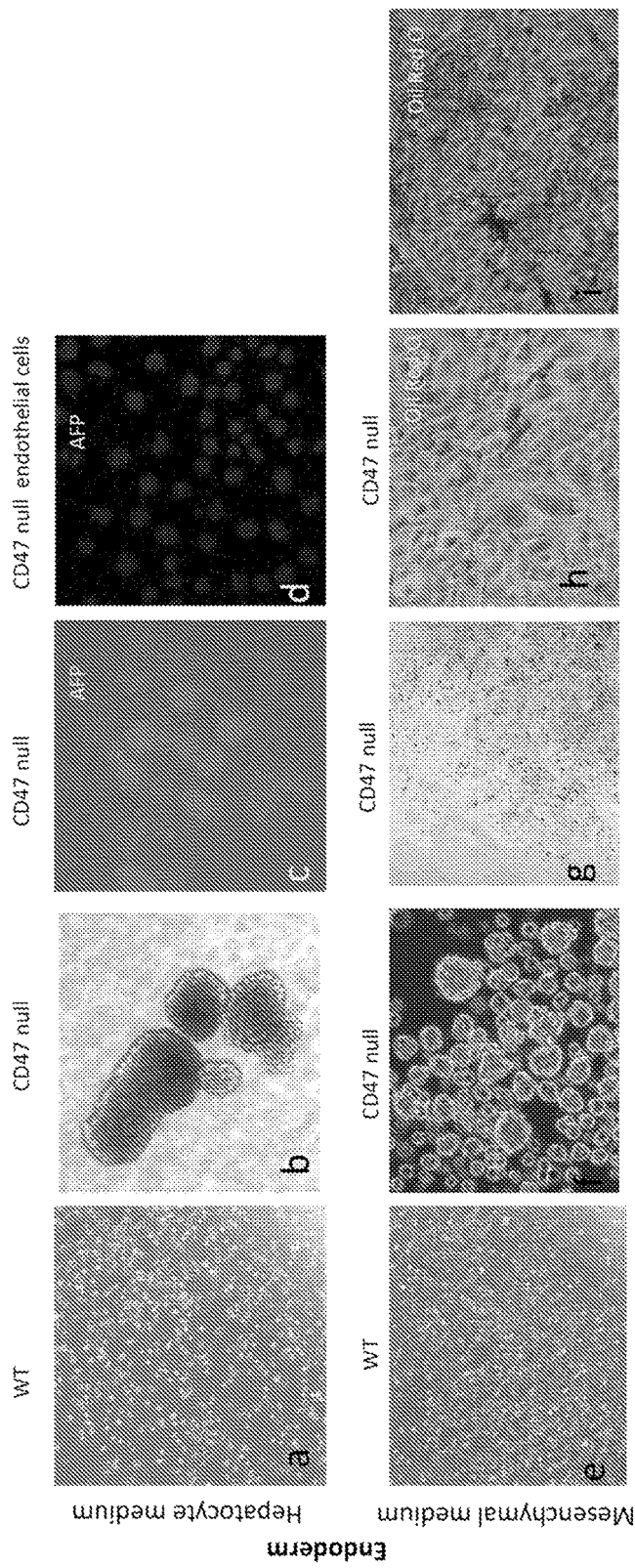

CD47 null endothelial cells cultured in hepatocyte growth medium developed into cystic EBs and then differentiated into cells that expressed the hepatocyte marker α-fetoprotein (AFP, FIG. 12B, panels a-c). The CD47-null endothelial cells from which these were derived did not express AFP (FIG. 12B, panel d). Although, a few WT endothelial cells survived in the hepatocyte medium, EB-like clusters never formed, and no expression of AFP was observed.

WT and CD47 null endothelial cells were cultured in mesenchymal cell medium for 10 days. Only CD47 null cells formed EB-like clusters. Some colonies of the mesenchymal differentiated cells exhibited oil Red O$^+$ lipid vacuoles characteristic of adipocytes (FIG. 12B panels e-i). We also attempted direct transdifferentiation of CD47-null endothelial cells into mesenchymal cells. Fewer cells were oil red-positive compared to those obtained via EBs.

Figure 12C:
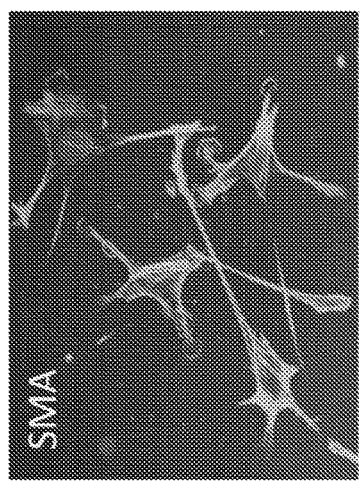

Dispersion of CD47-null EBs into serum-free smooth muscle medium containing platelet-derived growth factor and transforming growth factor-β1 resulted in differentiation of cells with typical vascular smooth muscle morphology and expressing the lineage marker smooth muscle actin (FIG. 12C).

Direct Hematopoietic Differentiation from Cultured CD47 Null Endothelial Cells:

Transfer of CD47-null endothelial cells into semisolid medium containing hematopoietic growth factors resulted in growth of colonies with phenotypes characteristic of myeloid (FIG. 13A) and erythroid colonies (FIGS. 13B, C). Colonies were obtained at frequencies of $2.6$-$8.3 \times 10^{-4}$ from three independent CD47-null endothelial cultures, whereas no large colonies were observed in equivalent cultures of WT lung endothelial cells (FIG. 13D).

To confirm the potential of CD47-null endothelial cell cultures to differentiate into the myeloid lineage, the cells were cultured with L929 conditioned medium as a source of macrophage colony stimulating factor (M-CSF) (Genovesi et al., *Vet. Immunol. Immunopathol.* 23:223-244, 1989). After 10 days a change in cell morphology was accompanied by a marked increase in the percentage of Mac2+ cells in treated CD47-null cells compared to the same cells in endothelial growth medium (FIGS. 13E-H). At the same time the treated cells showed loss of Sca-1 expression (compare FIG. 3C and FIG. 13I). Expression levels of other leukocyte and monocyte-specific markers including CD14, CD64, CD11c, Ly6C, Ly6G, CD11b, B220, and CD3e were unchanged. The cells were confirmed to lack CD47 expression (FIG. 13J).

Together, these results demonstrate that a population of multipotent cells is selectively maintained at high frequency in continuously cultured CD47-null, but not WT, endothelial cells. These cells support long term maintenance of viable endothelial cells in medium containing endothelial growth factors, but when deprived of serum CD47-null cells spontaneously generate cystic EBs that express pluripotency markers such as alkaline phosphate, SSEA-1 and c-Kit. These in turn can be induced to differentiate into cell types representative of all three embryonic germ layers when appropriate growth factors and cytokines are provided.

In Vivo Regulation of c-Myc and Tissue Stem Cell Abundance by CD47:

Increased expression of c-Myc mRNA compared to that in WT mice was detected in several organs from CD47-null mice (FIG. 5A). Because the highest elevation of c-Myc mRNA occurred in CD47-null spleen, we isolated several major cell types from this organ for further analysis. B cell (CD19$^+$) and CD4$^+$ T cell populations showed significant up-regulation of c-Myc mRNA, whereas CD8$^+$ T cells and monocytes did not (FIG. 5B). Nestin, Sox2, KLF4, and Oct4 mRNA levels were also markedly elevated in spleen from CD47-null mice (FIG. 5C). Consistent with the lesser elevation of c-Myc mRNA levels in lung, Oct4, Sox2, and nestin mRNA levels were moderately elevated in lung, but KLF4 was not elevated in this organ (FIG. 5D). Sox2 is normally expressed by Clara cells in conducting airways (Tompkins et al., *PLoS One* 4:e8248, 2009) and was similarly expressed in WT and CD47-null lung bronchiolar epithelium, but cells expressing higher levels of cytoplasmic Sox2 were selectively observed throughout the alveolar space of the CD47-null lung (FIGS. 5E-F).

Figure 13K:
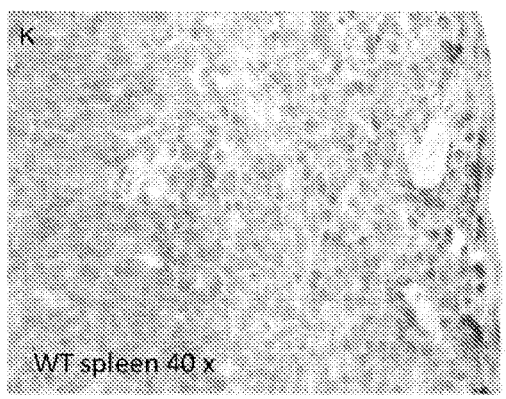
Figure 13L:
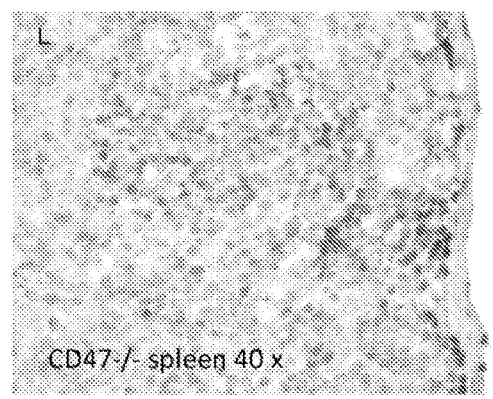

The spleen of adult mice contains a pool of multipotent CD45$^-$/Hox11$^+$ stem cells that reside in the sub-capsular red pulp and are capable of differentiating into diverse lineages (Faustman, *Discov. Med.* 5:447-449, 2005; Faustman and Davis, *Int. J. Biochem. Cell Biol.* 42:1576-1579, 2010). Consistent with these reports, we observed a limited number of cells with nuclear Sox2 protein expression in the sub-capsular region of WT mouse spleen (FIG. 5G) and sparse expression of Sox2-expressing cells in other compartments of the spleen. Similar subcapsular Sox2 immunoreactivity was seen in spleen sections from CD47-/- mice, but more extensive staining was observed in the adjacent red pulp (FIGS. 5H, 13K, L). These differences in Sox2 protein expression are consistent with the whole organ mRNA expression data and suggest that the absence of CD47 increases the number of tissue resident stem cells in vivo.

Figure 14A:
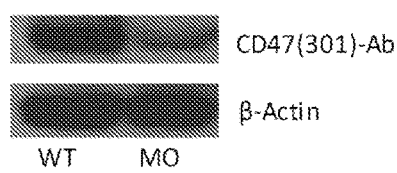
Figure 14B:
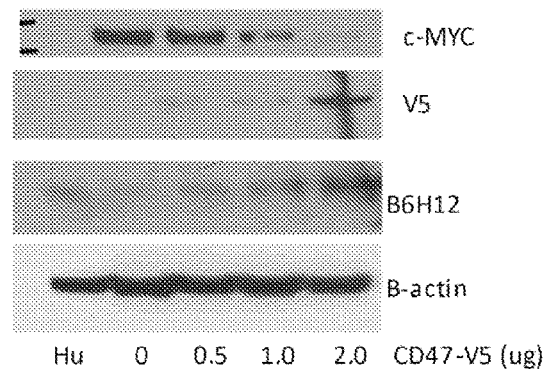
Figure 14C:
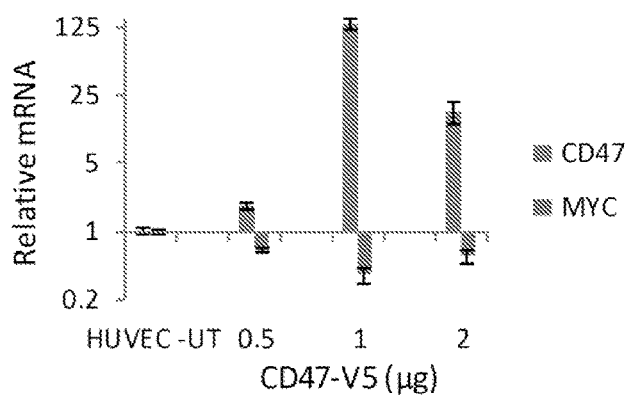

CD47 Expression Acutely Inhibits c-Myc Expression:

The above results establish a genetic linkage between CD47, maintenance of stem cells, and c-Myc expression. To clarify this relationship, WT splenic T cells from c-Myc-EGFP knock-in mice (Nie et al., *Cell* 151:68-79, 2012) were treated with a previously validated CD47-targeting antisense morpholino (Isenberg et al., *Circ. Res.* 100:712-720, 2007) and resulted in a 7-fold increase in c-Myc mRNA level at 24 h (FIG. 6A). Intraperitoneal injection of the CD47 morpholino into WT mice significantly decreased CD47 protein expression in vivo (FIG. 14A) and resulted in induction of c-Myc as well Oct4 and Sox2 mRNA levels in spleen at 48 hours (FIG. 6B).

Conversely, re-expression of CD47 in CD47-null endothelial cells by transiently transfecting a CD47 expression plasmid inhibited their proliferation and viability (FIG. 6C). c-Myc mRNA and protein levels fell when CD47 was re-expressed at a level sufficient to cause growth inhibition (FIGS. 6D-E, 14B-C). Growth suppression by transiently expressing CD47 could be bypassed by co-transfecting the cells with a c-Myc expression vector (FIG. 6C). Transient re-expression of CD47 in the null endothelial cells also decreased mRNA levels for KLF4, Sox2, and nestin (FIG. 6F). Notably, over-expressing c-Myc alone increased nestin and Oct4 mRNA expression, but co-expression of c-Myc with CD47 did not overcome the inhibitory effect of CD47 expression on KLF4, Sox2, or nestin, indicating that these CD47 signaling targets are Myc-independent.

Figure 7A:
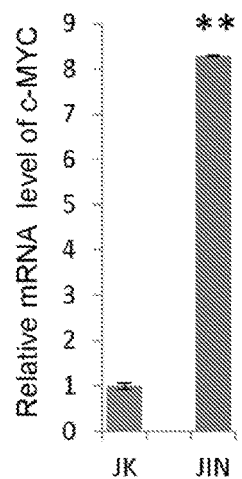
Figure 7B:
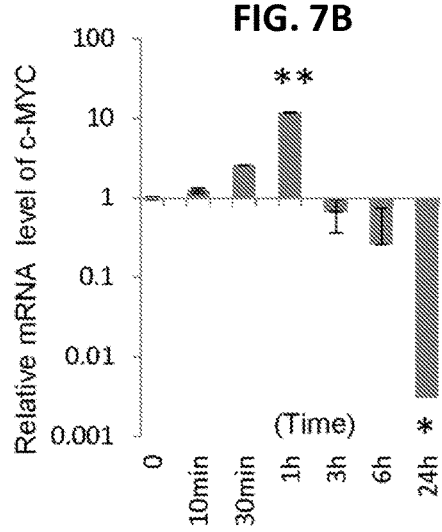
Figure 7C:
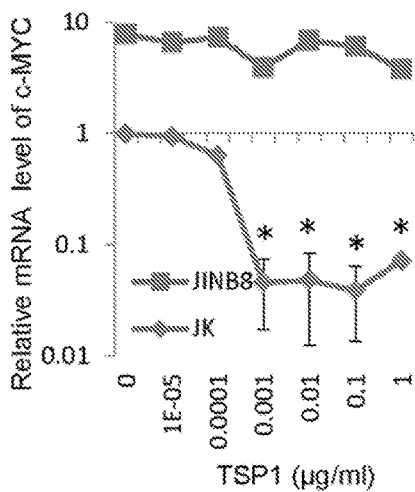
Figure 7D:
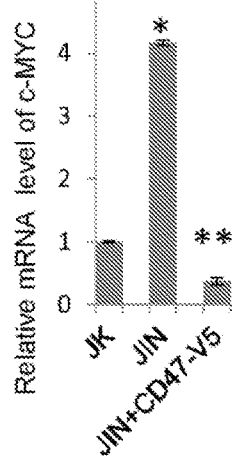

Thrombospondin-1 Controls c-Myc Via CD47:

The JinB8 somatic mutant of the Jurkat human T lymphoma cell line lacks CD47 (Reinhold et al., *Int. Immunol.* 11:707-718, 1999) and exhibited a similar over-expression of c-Myc mRNA relative to the parental Jurkat cells (FIG. 7A). Therefore, CD47 also negatively regulates c-Myc expression in human cells. Mice lacking the CD47 ligand thrombospondin-1 share most of the stress resistance phenotypes of CD47 null mice (Isenberg et al., *Am. J. Pathol.* 173:1100-1112, 2008; Roberts et al., *Matrix Biol.* 31:162-169, 2012), and muscle explants from thrombospondin-1-null mice exhibit increased vascular outgrowth into three-dimensional collagen gels relative to WT explants (Zhou et al., *Oncogene* 25:536-545, 2006). Consistent with these observations and the continuous growth of thrombospondin-1-null endothelial cells shown in FIG. 8, c-Myc levels in Jurkat T cells were transiently induced but then strongly inhibited by treatment with 2.2 nM thrombospondin-1 (FIG. 7B). Likewise treating low passage human renal tubular epithelial cells with TSP1 (2.2 nM) decreased expression of self-renewal transcription genes. Picomolar concentrations of thrombospondin-1 were sufficient to inhibit c-Myc expression in Jurkat cells at 24 hours, but the elevated c-Myc mRNA levels in Jurkat cells lacking CD47 were not significantly inhibited by thrombospondin-1 (FIG. 7C). Re-expression of CD47 in JinB8 cells reduced c-Myc mRNA expression (FIG. 7D) and restored the ability of thrombospondin-1 to inhibit c-Myc expression (FIGS. 14D-E). Therefore, CD47 is necessary for this activity of thrombospondin-1. The transient induction of c-Myc by thrombospondin-1 may be mediated by its other receptors expressed by Jurkat cells (Li et al., *J. Cell Biol.* 157:509-59, 2002).

Figure 7E:
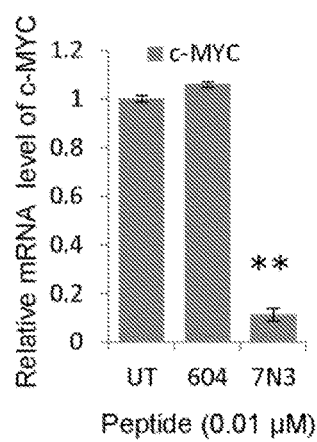

Similar suppression of c-Myc levels was observed in the presence of a CD47-binding peptide derived from thrombospondin-1 (peptide 7N3, FIG. 7E). A control peptide with a mutated CD47 binding motif (peptide 604) was inactive. Therefore, CD47 engagement is sufficient to inhibit c-Myc expression without the participation of other thrombospondin-1 receptors.

Endogenous thrombospondin-1 also controls expression of c-Myc mRNA in vivo (FIGS. 7F, G). c-Myc mRNA levels were elevated approximately 3-fold in thrombospondin-1-null spleen and lung tissues relative to the corresponding WT organs. Consistent with the data for CD47-null mice, Oct4, Sox2 and KLF4 mRNA levels were also elevated in thrombospondin-1-null spleen, but their levels were not significantly increased in lung.

Dysregulation of c-Myc Confers Resistance to CD47 Signaling:

One paradox that arises from the above results is that high CD47 expression appears to be a disadvantage for cells because it suppresses c-Myc expression, yet many tumor cells and some stem cells have been reported to have elevated CD47 expression (Chao et al., *Cancer Res.* 71:1374-1384, 2011; Chao et al., *Cell* 142:699-713, 2010; Majeti et al., *Cell* 138:286-299, 2009; Willingham et al., *Proc. Natl. Acad. Sci. USA* 109:6662-6667, 2012). One possible explanation is that other pathways that drive c-Myc expression could overcome the inhibitory effects of CD47 signaling. To examine whether c-Myc is the primary target of CD47 signaling that inhibits cell growth, we used Myc-null rat1 fibroblasts that constitutively express a tamoxifen activatable c-Myc-estrogen receptor chimeric protein (O'Connell et al., *J. Biol. Chem.* 278:12563-12573, 2003). In contrast to cells expressing only native c-Myc controlled by its endogenous promoter, transfecting the Myc-expressing Rat1 fibroblasts with the CD47 expression plasmid did not inhibit their growth (FIG. 7H).

We previously reported that blocking CD47 conferred radioprotection to normal cells and mice, but B16 melanomas grown in these mice were not protected and instead showed enhanced radiosensitivity when CD47 was blocked (Maxhimer et al., *Sci. Transl. Med.* 1:3ra7, 2009). This, combined with previous evidence that c-Myc expression is dysregulated in B16 cells (Huber et al., *Br. J. Cancer* 59:714-718, 1989), suggested that CD47 signaling might not regulate c-Myc in these cells. Consistent with this hypothesis, transiently over-expressing CD47 in B16 melanoma cells did not inhibit their growth (FIG. 7I).

Over-expression of CD47 also failed to inhibit growth or survival of Raji Burkitt's lymphoma cells where c-Myc expression is driven by enhancer regions donated by the translocated immunoglobulin heavy chain (Kanda et al., *J. Biol. Chem.* 275:32338-32346, 2000) (FIG. 7H). In agreement with these growth data, cell cytotoxicity (LDH release) was increased by re-expressing or over expressing CD47-FLAG in normal mouse lung endothelial cells but not in B16 melanoma, Raji Burkitt's lymphoma, and Myc null Rat 1 fibroblasts (FIGS. 14F-H). Together, these results establish that c-Myc is the dominant target of CD47 signaling for limiting cell growth and suggest that this regulation requires 5' regions of the c-Myc gene, which are absent in Raji cells.

Discussion

These results demonstrate that a population of multipotent stem cells is selectively maintained at high frequency in primary and continuously cultured CD47-null endothelial cells. These cells support long term maintenance of viable endothelial cells in medium containing endothelial growth factors, but when deprived of serum, CD47-null cells spontaneously generate EB-like clusters that express pluripotency markers including alkaline phosphatase, Nanog, and SSEA-1. These in turn can be induced to differentiate into cell types representative of all three embryonic germ layers when appropriate growth factors and cytokines are provided. In contrast to exhibiting these characteristics of iPS cells, the CD47-null EB-like clusters did not form teratomas in mice. Consistent with their lack of teratoma formation, no loss of the tumor suppressor gene PTEN or activation of oncogenes including Ras was found in CD47-null EB-like clusters. Loss of PTEN has been reported to increase teratoma formation by pluripotent stem cells (Lindgrean et al., *PLoS One* 6:e16478, 2011) and others have shown that stem cells can remain pluripotent when teratoma formation is suppressed (Vazquez-Martin et al., *Sci. Rep.* 2:964, 2012). Thus, while it is possible that the CD47-null EB-like clusters might not be fully pluripotent, but their lack of tumorigenicity provides an advantage for therapeutic applications.

These data further reveal that suppression of c-Myc expression is an important mechanism by which thrombospondin-1 signaling via CD47 controls cell growth and differentiation. c-Myc is now recognized to be a universal amplifier of the expression of actively transcribed genes in somatic and embryonic stem cells (Nie et al., *Cell* 151:68-79, 2012), so the ability of CD47 to control c-Myc expression identifies CD47 as cell surface receptor that globally regulates gene expression. Combined with its specific regulation of the stem cell transcription factors Oct4, Sox2 and Klf4, CD47 limits the growth, self-renewal, and reprogramming capacity of primary murine cells in tissue culture. Suppression of these major stem cell transcription factors by CD47 also occurs in vivo and can be modulated by targeting CD47. A corresponding increase in abundance of tissue stem cells, suggested by the increased expression of Sox2 in several organs of CD47-null mice, may contribute to the remarkable ability of tissues in these mice and in thrombospondin-1 null mice to recover from various injuries (Hayashi et al., *Hepatology* 55:1562-1573, 2012; Roberts et al., *Matrix Biol.* 31:162-169, 2012). In addition to the potential therapeutic utility of CD47 antagonists for treating such injuries, the present data suggest that antagonists of CD47 signaling could be used to increase the expansion of tissue stem cells for cell-based therapies and tissue engineering. CD47 antagonists could also be used to enhance the generation of lineage-committed or iPS cells and to circumvent the requirement for ectopic expression using plasmids or integrating retroviruses encoding tumor promoting genes such as c-Myc.

c-Myc expression greatly increases the frequency of iPS cells induced by combined ectopic expression of Oct3/4, Sox2, and Klf4 (Varlakhanova et al., *Differentiation* 80:9-19, 2010). Because data provided herein show that CD47 limits c-Myc expression and other studies have shown that thrombospondin-1 inhibits endothelial progenitor cell function via CD47 (Smadja et al., *Arterioscler. Thromb. Vasc. Biol.* 31:551-559, 2011), it is remarkable that CD47 expression is elevated on hematopoietic stem cells (Jaiswal et al., *Cell* 138:271-285, 2009). CD47 in this context was proposed to prevent clearance of stem cells by NK cells or macrophages expressing the CD47 counter-receptor SIRPα (Jaiswal et al., *Cell* 138:271-285, 2009; Kim et al., *Tumour Biol.* 29:28-34, 2008), but we propose that such stem cells must adapt to the cell-autonomous inhibitory effects of high CD47 expression that suppress c-Myc and other stem cell transcription factors. c-Myc expression is presumably maintained through other regulatory pathways to preserve viability. The loss of viability observed herein following the acute withdrawal of c-Myc due to CD47-ligation or restoring CD47 expression in null cells may be an example of oncogene addiction in normal cells. These results indicate that a downward excursion of Myc must be carefully managed to prevent cell death or senescence.

Previous studies have implicated thrombospondin-1 as an inhibitor of certain stem cell functions but have not invoked CD47 as the relevant receptor. Thrombospondin-1 null mice exhibited 5-fold more circulating endothelial lineage-committed stem cells (EPCs, CD13$^+$/VEGFR-2$^+$/CD45$^-$/CD117$^+$) than WT mice (Shaked et al., *Cancer Cell* 7:101-111, 2005). Because the elevation in EPCs was suppressed when the null mice were treated with a drug targeting the thrombospondin receptor CD36, the increased number of EPCs was attributed to loss of anti-angiogenic thrombospondin-1 signaling via CD36 in the null. Conversely, elevated thrombospondin-1 levels in diabetes and peripheral artery disease have been associated with suppression of vascular wound repair mediated by EPCs (Ii et al., *Circ. Res.* 98:697-704, 2006; Smadja et al., *Arterioscler. Thromb. Vasc. Biol.* 31:551-559, 2011). Notably, EPCs highly express CD47, and suppression of CD47 by RNAi enhanced their proliferation and angiogenic potential (Smadja et al., *Arterioscler. Thromb. Vasc. Biol.* 31:551-559, 2011). The authors attributed this to increased activity of the SDF-1/CXCR4 pathway, but the data presented herein reveal a broader role of CD47 to limit stem cell function by suppressing c-Myc and other stem cell transcription factors. Furthermore, because CD47-null stem cells show an enhanced capacity to differentiate along diverse lineages, it appears that the inhibitory function of CD47 in stem cell maintenance is not restricted to the endothelial lineage.

In light of the results presented herein, thrombospondin-1 and c-Myc can be seen to form a negative feedback loop in normal cells that limits the expression of both genes. This feedback would normally limit the expression of inhibitory thrombospondin-1 and thereby promote tissue renewal and regeneration. As an inhibitory cell surface receptor that controls self-renewal, CD47 may be critical for understanding how the microenvironment in the stem cell niche regulates stem cell differentiation. Without being bound by theory, it appears that CD47 may directly transmit a negative signal from the environment that inhibits self-renewal or proliferation, or lateral cross talk of CD47 with integrins and growth factor receptors in the plasma membrane (Frazier et al., *UCSD Nature Molecule Pages*, doi:10.1038/mp.a002870.01 2010; Kaur et al., *J. Biol. Chem.* 285:38923-38932, 2010) may negatively modulate these signals in stem cells. The present studies identify thrombospondin-1 as a potentially key environmental signal that inhibits stem cell self-renewal via CD47.

Figure 15:
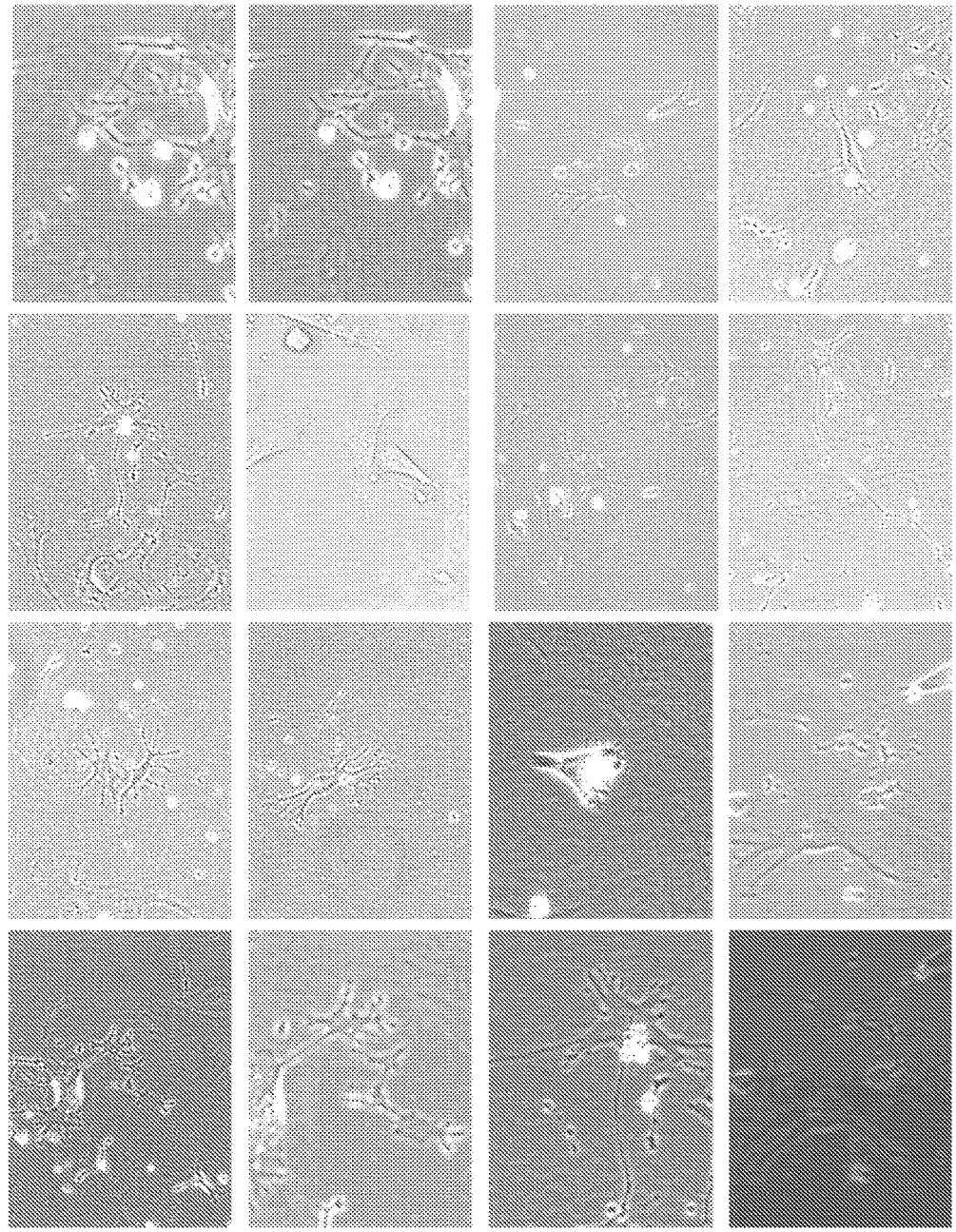
FIG. 15 is a series of digital images showing projecting neurites from CD47-null embryoid bodies cultured in neural medium on gelatin coated dishes to induce neuroepithelial differentiation.

Example 2: Efficient Neural Differentiation of CD47 Null Stem Cells Occurs without Malignant Transformation CD47-null embryoid bodies were cultured in neural medium on gelatin coated dishes as described in Example 1 to induce neuroepithelial differentiation. The neuroepithelial morphology of the resulting cells showed that this germ layer arises efficiently from CD47-null EBs. WT cells were not capable of forming EBs or subsequent reprogramming. The neural differentiation of the cells was further demonstrated by the presence of neurites projecting from the monolayers (FIG. 15).

The neuroepithelial differentiated CD47-null cells were stained with markers to confirm their phenotypes and to determine whether malignant transformation had occurred. The continuously growing CD47-null cells expressed the proliferation marker CDK2 but lacked over-expression of the transformation marker Ras. This demonstrates that blocking CD47 permits self-renewal without causing malignant transformation of the cells. Similarly, mouse CD47 null induced stem cells grown in neural differentiation medium maintained the neural marker N-cadherin but did not lose expression of the tumor suppressor PTEN. Therefore, the CD47 null cells are multipotent but are not transformed.

Example 3: Use of CD47 Ligands to Induce Self-Renewal in Primary Human Endothelial Cells This example describes use of CD47 binding peptides, CD47 antibodies (either anti-mouse or anti-human CD47), and CD47 antisense morpholino to induce stem cell properties and enable self-renewal. Also shown is activity to reprogram primary human endothelial cells.

Figure 16:
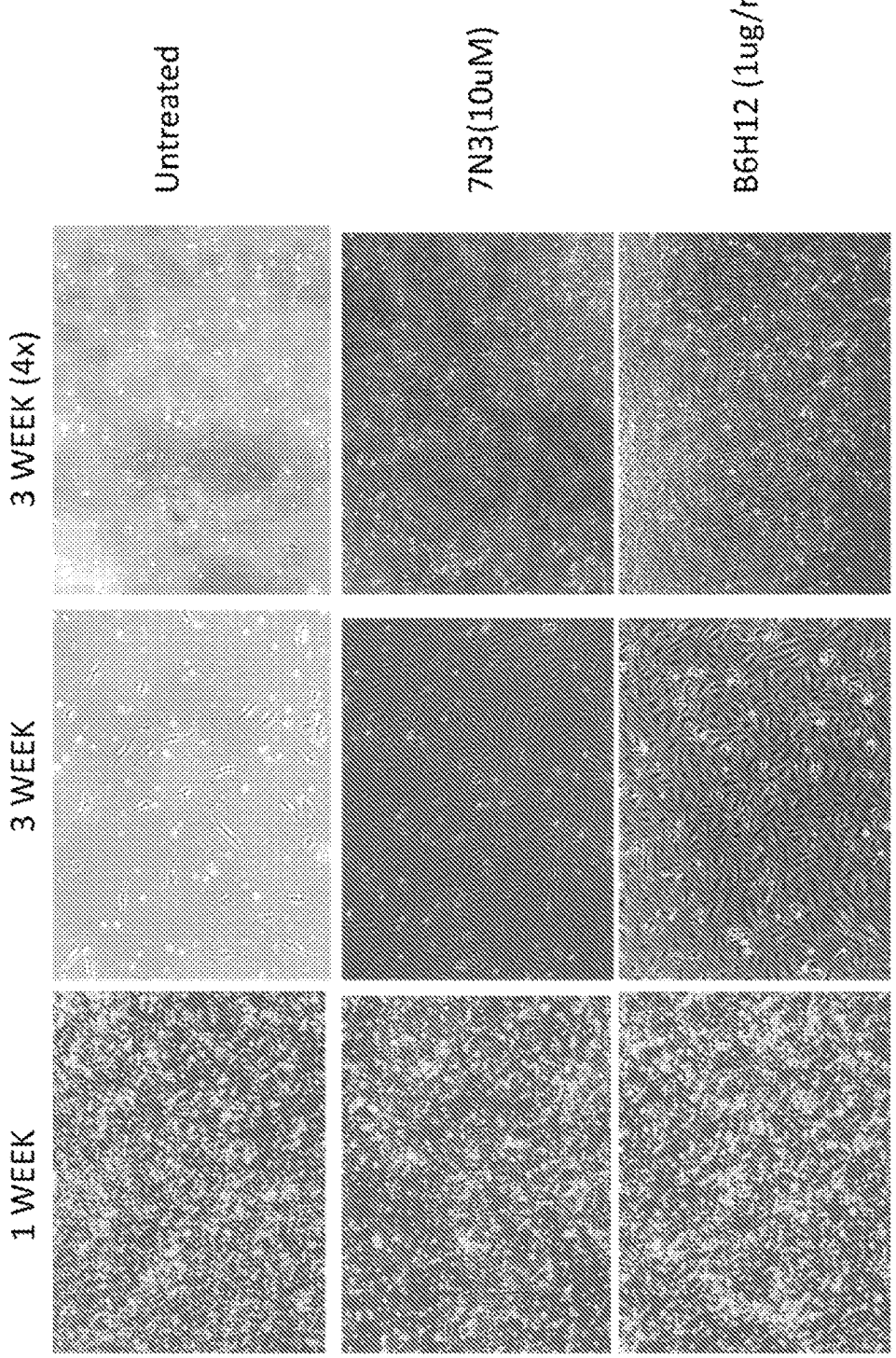
FIGS. 16A-C are digital images of human umbilical vein endothelial cells (HUVEC) in continuous culture (FIG. 16A), which become senescent. Treatment with the CD47-binding peptide 7N3 (10 µM.
Figure 17:
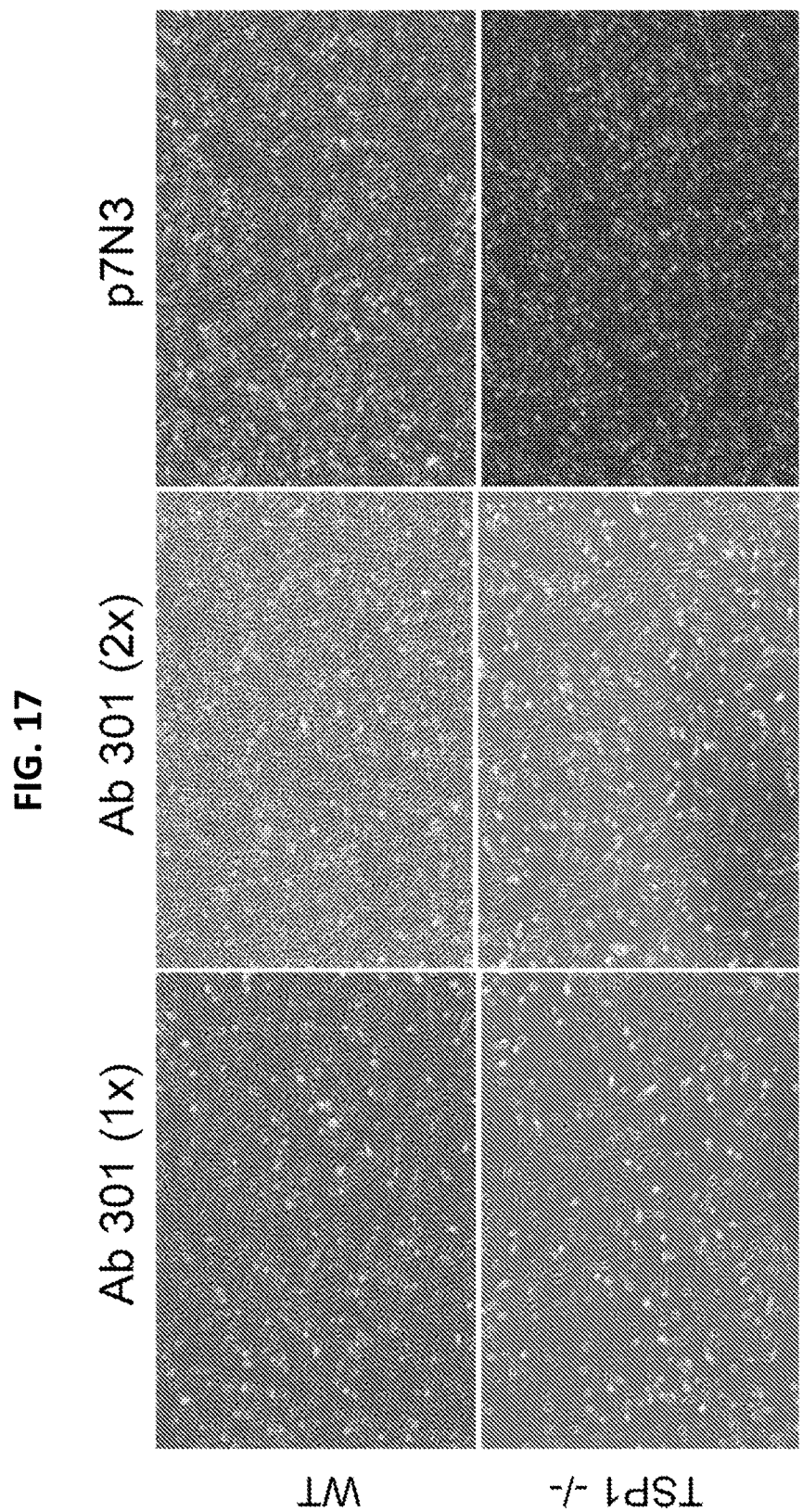
FIG. 17 is a series of digital images of primary WT or TSP1-null murine lung endothelial cells treated with a function blocking anti-mouse CD47 antibody (clone 301) or the peptide 7N3. Cells were treated once (1×) or twice (2×) with Ab301.

Human umbilical vein endothelial cells (HUVEC), which express CD47, normally become senescent with repeated passage in tissue culture (FIG. 16A). However, treatment with the CD47-binding peptide 7N3 (10 µM) or with the function blocking anti-human CD47 antibody B6H12 (1 µg/ml) dramatically increased the sustained proliferation of these cells (FIGS. 16B and C). Similar results were obtained with primary WT murine lung endothelial cells (which express CD47), using peptide 7N3 or a function blocking anti-mouse CD47 antibody (clone 301) to treat primary mouse lung endothelial cells (FIG. 17). Similar responses were seen on the TSP1 null cells, but their response was less than the WT cells. This demonstrates that the ability of the CD47 binding peptide 7N3 and CD47 blocking antibodies to induce self-renewal is not restricted to human cells and can be used in other mammalian species.

Figure 18:
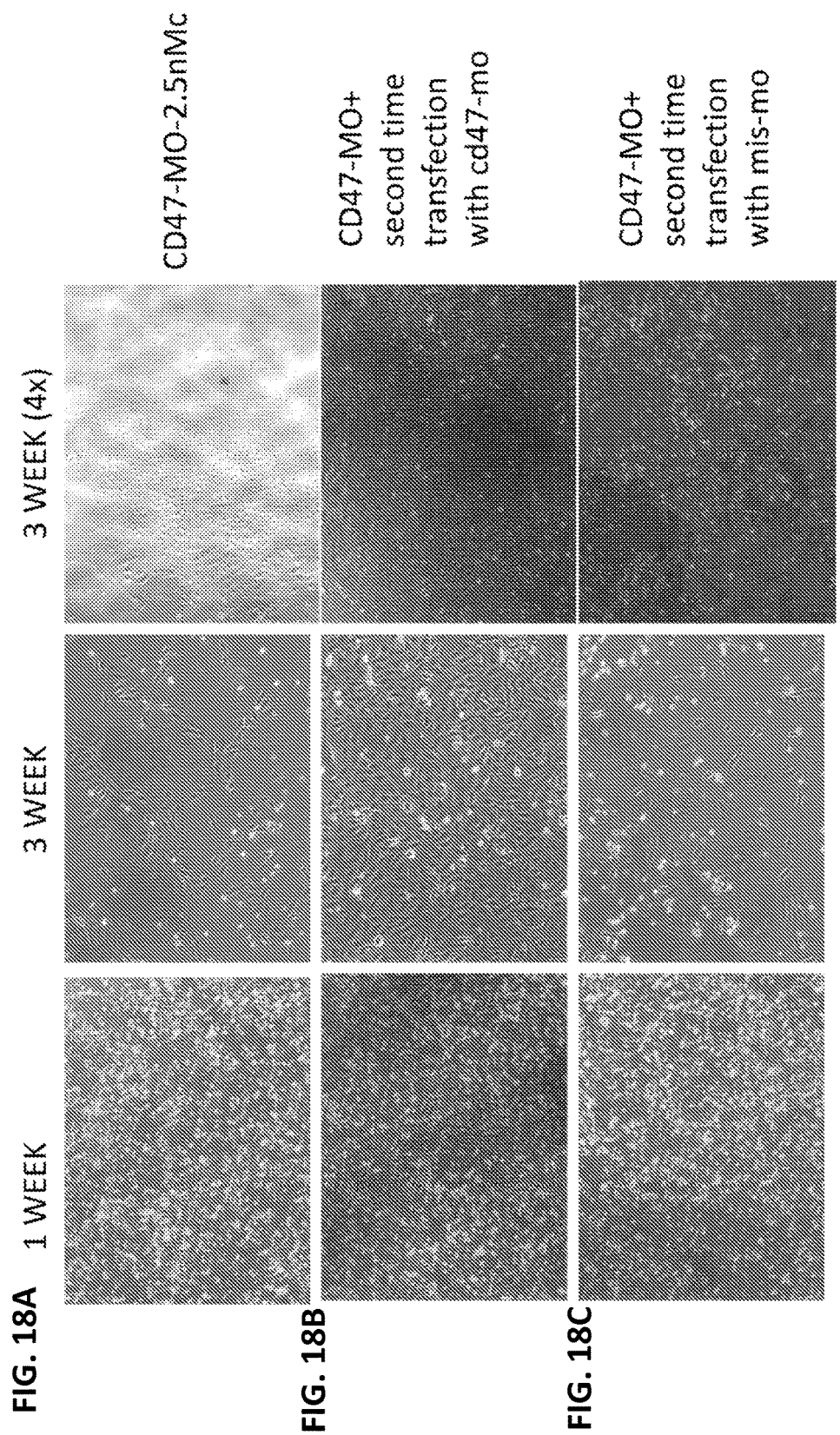
FIGS. 18A-C is a series of digital images of HUVEC cells cultured for 1-3 weeks after transfection with an antisense CD47 morpholino (FIG. 18A). In some cases, the cells were transfected a second time with either the antisense CD47 morpholino (FIG. 18B) or a mismatch control morpholino (mis-mo.
Figure 19:
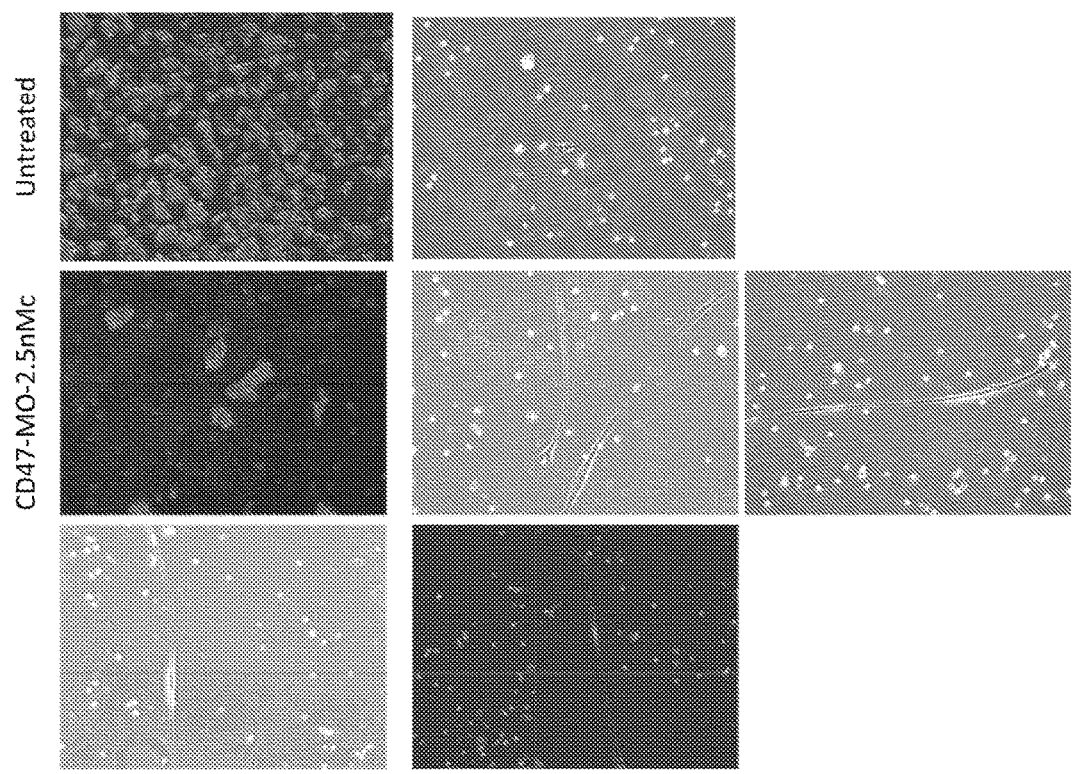
FIG. 19 is a series of digital images showing untreated HUVEC cells or HUVEC cells treated with CD47 morpholino which were directly transferred into neural differentiation medium. Treatment with CD47-morpholino resulted in sporadic appearance of cells with neuronal phenotypes.

Temporary suppression of CD47 expression using an antisense CD47 morpholino at 2.5 µM similarly enabled self-renewal in HUVEC (FIGS. 18A and B). A second treatment using the same concentration of CD47 morpholino showed an enhanced proliferative response. This demonstrates that antisense suppression of CD47 is sufficient to induce self-renewal. Direct transfer of the HUVEC cells transfected with the CD47 morpholino into neural differentiation medium resulted in sporadic appearance of cells with neuronal phenotypes (FIG. 19). Therefore, antisense suppression of CD47 is sufficient to induce reprogramming of primary endothelial cells of a mesodermal lineage into an ectodermal lineage.

A new vial of HUVEC at passage 1 was thawed and split in to two 25 cm$^3$ Nunc tissue culture flasks. One flask (P1) was treated with CD47-MO (2.5 µM). The other was kept as untreated. The HUVEC were transferred in to new Nunc tissue culture flask 75 cm$^3$ and cultured for 2 weeks using EGM2 medium. After 2 weeks, the HUVEC (untreated and CD47-MO treated) were assessed for generation of EBs, neural differentiation, and cardiomyocytes differentiation. HUVEC EBs: untreated and CD47-MO cells were cultured in serum free medium for EB formation. CD47-mo and untreated cells formed different phenotype cell aggregation after 3-6 days. Direct Neural Differentiation media: Equal numbers of HUVEC cells (untreated and cd47-mo) were cultured with neural basal media (same for mouse lung endothelial cells) for 6 days. CD47-MO treated cells survived better than untreated. After 6 days, the neural basal media was replaced with neural differentiation media (same used for mouse lung endothelial cells). None of the untreated HUVEC survived. The CD47-MO exhibited neural phenotype and their survival was observed up to 15 days, although their numbers were low.

Figure 20A:
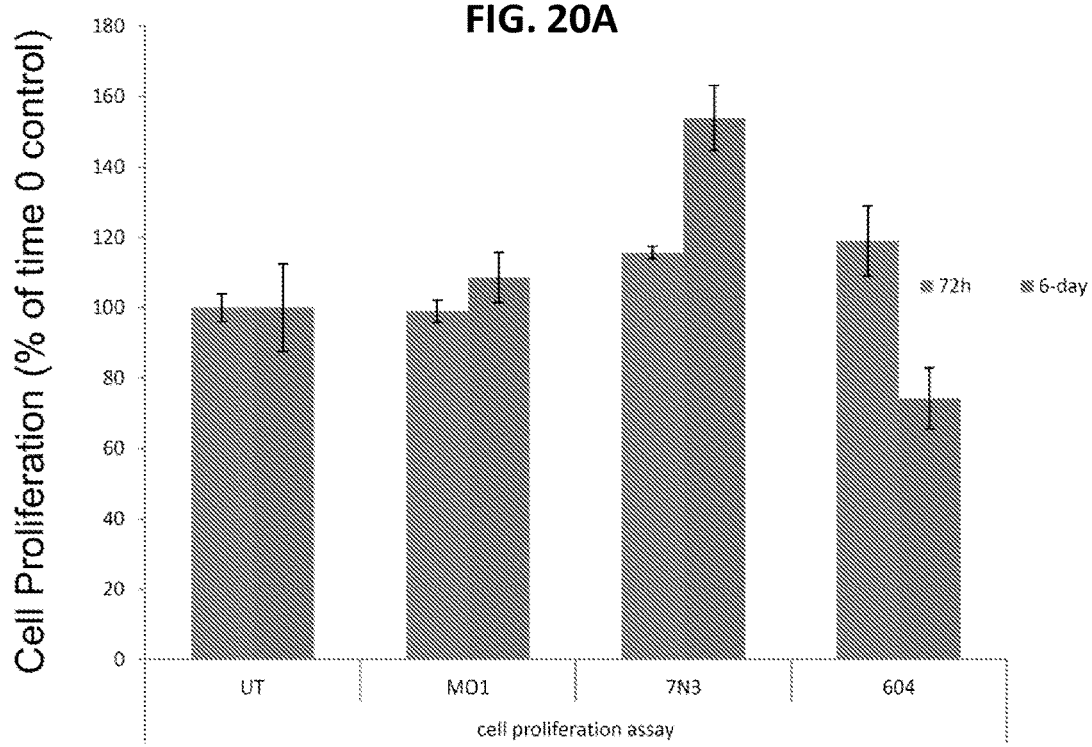
FIGS. 20A and B are a pair of graphs showing proliferation of untreated HUVEC cells (UT) or HUVEC cells treated with CD47-morpholino (MO1), 7N3 peptide, or control peptide 604 assessed using MTS assay. By 6 days post-treatment, cells treated with the CD47 binding peptide 7N3 showed enhanced proliferation, whereas control cells treated with the inactive peptide analog 604 showed decreased proliferation, cells treated with CD47 morpholino showed a slight but not significant enhancement of proliferation (FIG. 20A; left bars, 72 hours post-treatment; right bars, 6 days post-treatment). When the cells were analyzed at 3 weeks post-treatment, cells treated with CD47 morpholino showed significantly increased proliferation relative to control HUVEC (FIG. 20B).
Figure 20B:
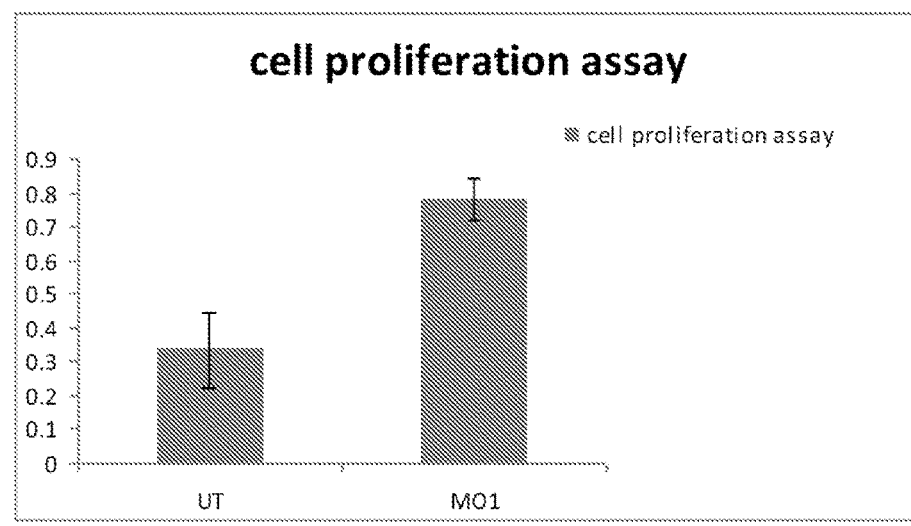

Proliferative capacities of the treated HUVEC (CD47 morpholino, 7N3 peptide, or 604 control peptide) were assessed using MTS assays. By 6 days post-treatment cells treated with the CD47 binding peptide 7N3 showed enhanced proliferation, whereas control cells treated with the inactive peptide analog 604 showed decreased proliferation (FIG. 22A). At 6 days, cells treated with CD47 morpholino showed a slight but not significant enhancement of proliferation (FIG. 20A). However, when the cells were analyzed at 3 weeks post-treatment cells treated with CD47 morpholino showed significantly increased proliferation relative to control HUVEC (FIG. 20B).

Figure 21A:
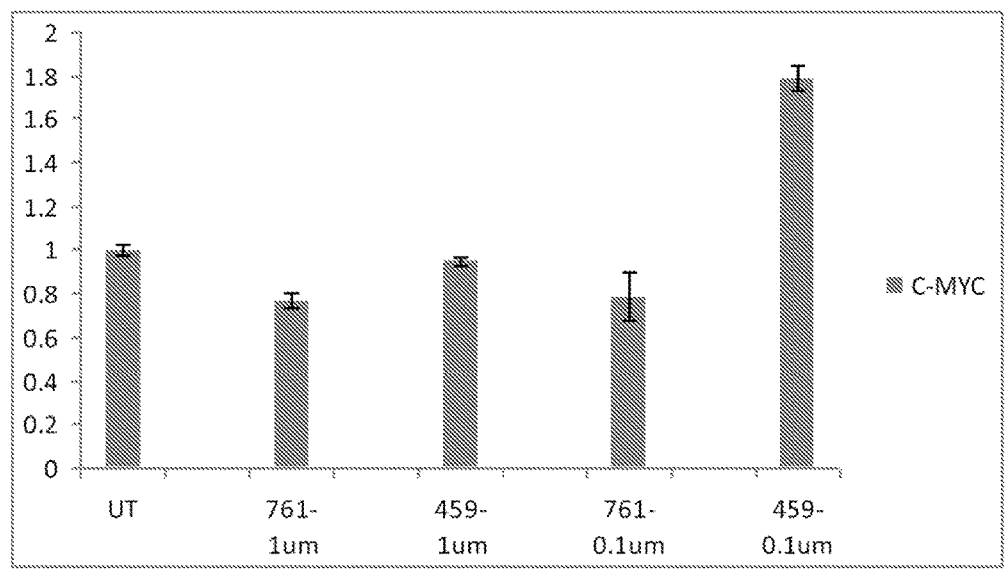
FIGS. 21A and B are a pair of graphs showing QPCR analysis of c-Myc mRNA expression. WT Jurkat T cells were treated with the CD47 binding peptide 459 (also known as peptide 4N1) or control peptide 761 at 1 µM or 0.1 µM (FIG. 21A). WT Jurkat T cells were also treated with the CD47-binding peptide 7N3 or the control peptide 604 at 1 µm or 10 µM (FIG. 21B).
Figure 21B:
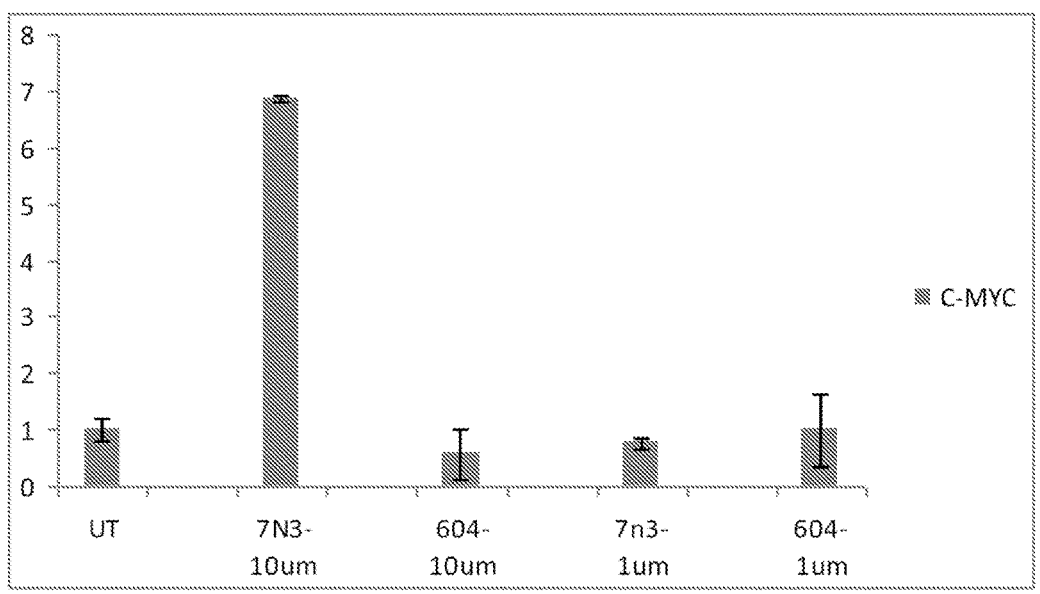

Treatment of WT Jurkat T cells with the CD47 binding peptide 459 (also known as peptide 4N1 with the sequence RFYVVMWK (SEQ ID NO: 37)) at 0.1 µM significantly increased expression of mRNA encoding the stem cell transcription factor c-Myc at 72 hours relative to Jurkat cells treated with the control peptide 761 (with the sequence RFYGGMWK (SEQ ID NO: 38)) (FIG. 21A). Treatment with the CD47-binding peptide 7N3 (FIRVVMYEGKK; SEQ ID NO: 1) resulted in a more dramatic increase in c-Myc expression, whereas the control peptide 604 (with the sequence FIRGGMYEGKK; SEQ ID NO: 2) did not (FIG. 21B).

Real time QPCR analysis of HUVEC after treatment with peptide 7N3 or the CD47 blocking antibody B6H12 and grown in EBM serum free (neural basal media) medium for 3 weeks showed high expression of mRNAs encoding c-Myc and other stem cell transcription factors including Sox2, Klf4, and Oct4 and expression of the stem cell marker nestin (Table 1). Control HUVEC did not survive after 3 weeks in the same serum free medium. Therefore, transient blocking of CD47 in primary human cells is sufficient to induce their conversion to self-renewing stem cells.

TABLE 1

Real-time PCR of HUVECs treated for three weeks with neural medium and 7N3 peptide or B6H12 antibody

| Gene | Treatment | C(t) |
| --- | --- | --- |
| c-Myc | 7N3 | 30.18728 |
|  |  | 18.48635 |
|  | B6H12 | 24.17887 |
|  |  | 24.59558 |
| sox2 | 7N3 | 28.08806 |
|  |  | 29.00019 |
|  | B6H12 | 30.36231 |
|  |  | 31.37936 |
| klf4 | 7N3 | 26.31469 |
|  |  | 26.16546 |
|  | B6H12 | 26.90761 |
|  |  | 28.41938 |
| nestin | 7N3 | 31.6104 |
|  |  | 31.32142 |
|  | B6H12 | 32.83383 |
|  |  | 32.9545 |
| 18S RNA | 7N3 | 6.115119 |
|  |  | 6.079316 |
|  | B6H12 | 6.229277 |
|  |  | 6.21683 |
| Oct4 | 7N3 | 34.47726 |
|  |  | 34.00265 |
|  | B6H12 | N/A |
|  |  | N/A |

Figure 22:
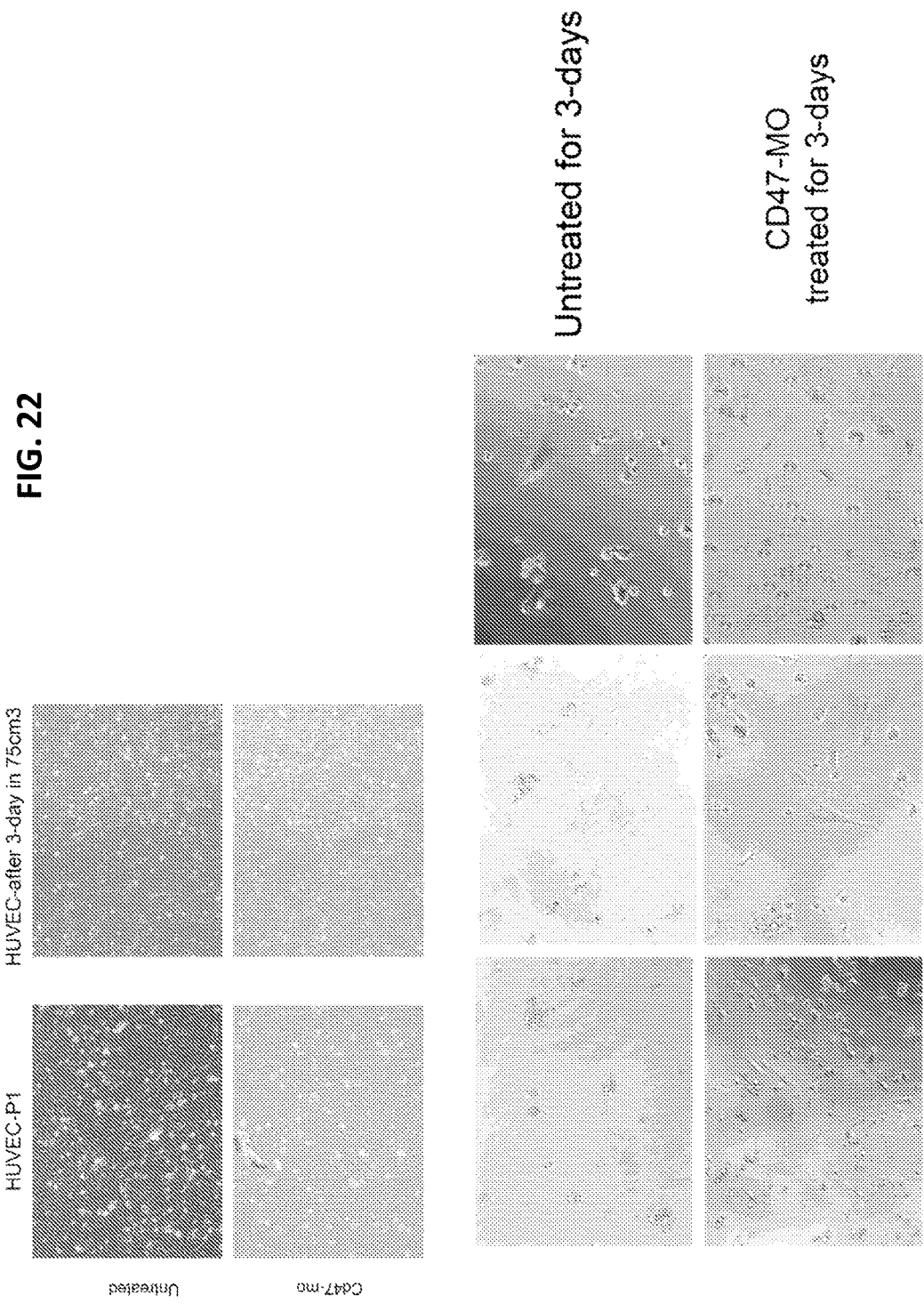
FIG. 22 is a series of digital images showing direct cardiomyocyte differentiation of HUVEC following antisense suppression of CD47 expression (CD47-MO). The untreated HUVEC were unable to survive in this medium after 3 days, but the treated cells survived and underwent differentiation.

Finally, equal numbers of HUVEC (untreated and cd47-mo treated at passage 1) were plated in 6-well plates with EGM2 media for 24 hours. The next day, EGM2 medium was replaced with cardiomyocyte differentiation media (Millipore). The untreated HUVECs were unable to survive in this medium after 3 days, but the treated cells survived and underwent differentiation (FIG. 22). CD47-MO cells survived up to 10 days. Thus, antisense suppression of CD47 is sufficient to induce reprogramming of primary endothelial cells into cardiomyocyte lineage.

Though this example is provided using one specific primary cell type, this is exemplary only and it is expected that other obtainable primary human cell types can also be used, such as skin fibroblasts, bone marrow cells, adipose tissue, mucosal tissue biopsies, umbilical cord, placenta, etc.

Figure 24:
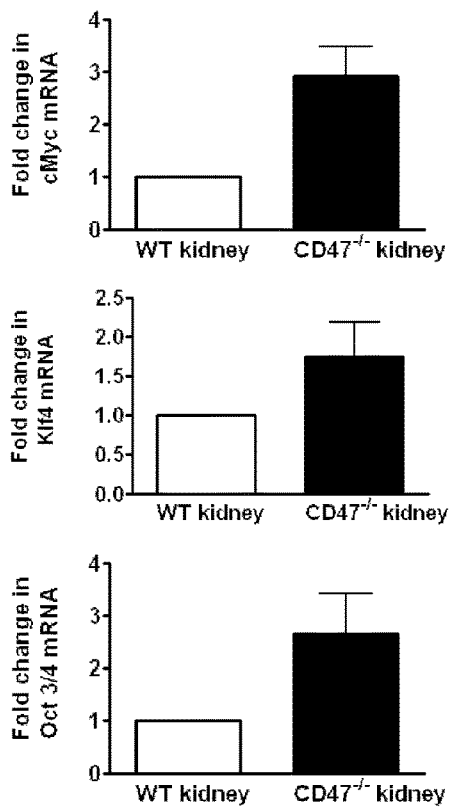
FIG. 24 is a series of graphs showing increased self-renewal transcription gene levels in kidneys from WT and CD47−/− mice. RT-PCR analysis of c-Myc (top panel), Klf4 (middle panel), and Oct3/4 (bottom panels) in kidneys from WT and CD47−/− male age matched mice (n=4 of each strain).

Example 4: Repopulation of Decellularized Tissue Matrix is Enhanced by CD47 Blockade Self-Renewal Genes are Upregulated in Kidneys Lacking CD47:

Renal failure is the leading indication for visceral organ transplantation worldwide. There are no currently successful bio-engineered renal organ platforms. CD47 controls multiple pro-survival signals in wound injury. It is not clear if this is true under basal non-injury conditions. mRNA levels of freshly harvested kidneys were assessed from CD47+/+ and CD47−/− animals and significant increases were found in multiple self-renewal stem cell transcription factors including c-Myc, Klf4, Oct3/4 (FIG. 24) and Sox2. These results show that in the absence of injury CD47 limits self-renewal transcription factors and stem-cell/pluripotent potential and defines a role for CD47 in this process. It has previously been shown that the TSP1-CD47 axis is upregulated in numerous diseases and in acute wound conditions. In acute kidney injury and pulmonary hypertension this has been most recently been shown (Rogers et al., *J. Am. Soc. Nephrol.* 23:1538-1550, 2012; Bauer et al., *Cardiovasc. Res.* 93:682-693, 2012).

Figure 25:
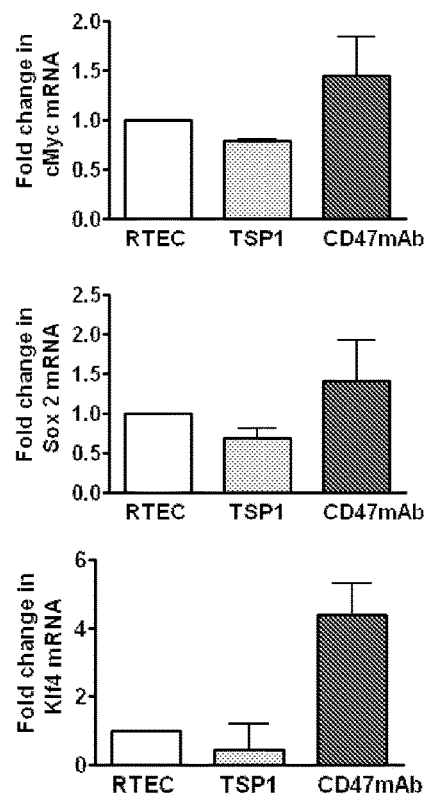
FIG. 25 is a series of graphs showing that blockade of CD47 elevates self-renewal transcription factors in human renal cells. Human rTEC were treated with TSp1 (2.2 nmol/L)±a CD47 monoclonal Ab (clone B6H12, 1 µg/ml) and RT-PCR performed for the indicated targets (top, c-Myc; middle, Sox2; bottom, Klf4). Results are the mean (±S.E.M.) of three separate experiments.

TSP1 Inhibits Self-Renewal Signals in Primary Human Renal Tubular Epithelial Cells, and CD47 Blockade Therapy Elevates Self-Renewal Genes in Human Renal Cells:

It is not clear what role the TSP1-CD47 signal cascade played on self-renewal signaling in specific renal cell types. We wanted to confirm in human cells that activation of CD47 inhibits self-renewal genes. Renal tubular epithelial cells (rTEC) are a primary source of injury in the kidney. Human rTEC were treated with a low concentration of exogenous TSP1 (2.2 nmol/L) and found suppression of self-renewal genes including cMyc and Sox2 and Klf4 (FIG. 25). Conversely treating rTEC with a CD47 antibody that prevents TSP1 activation of CD47 (anti-CD47 B6H12 antibody) elevated self-renewal genes significantly including cMyc, Sox2 and Klf4 (FIG. 25) and Oct3/4 and the stem cell marker nestin. Thus, in human renal cells CD47 blockade increases the stem cell-pluripotent capacity of renal cells.

Figure 26:
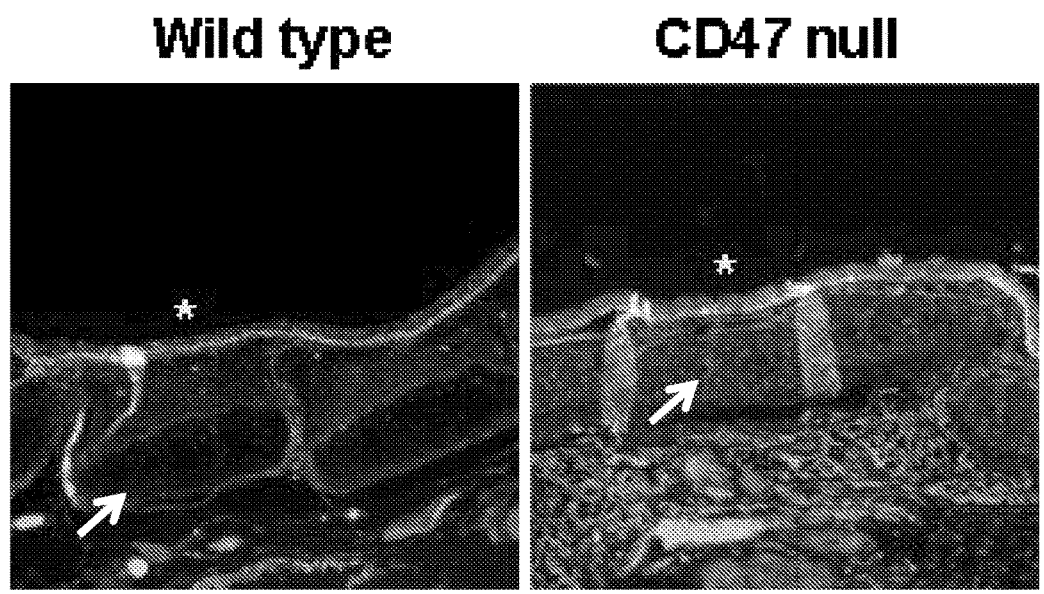
FIG. 26 is a pair of digital images showing that lack of CD47 signaling provides for complete generation of a trachea. Orthotopic tracheal transplantation of decellularized tracheal scaffolds, WT-to-CD47-null and WT-to-WT, was performed. Eight weeks after transplantation decellularized tracheas in both WT and CD47-null mice displayed basal layer K5+ cells (layer below asterisk). However, decellularized transplants in CD47-null mice display much more overall cellular repopulation and complete cartilage restoration (arrows) as compared to transplants in WT.

Restoration of Decellularized Trachea is Enhanced in the Absence of CD47:

Strategies developed to improve cell survival, engraftment, and angiogenesis of decellularized tracheal scaffolds have the potential to eliminate a major hurdle to wide spread utilization and clinical translation of this approach with likely applications to bioengineered skin, heart valves and joints. The trachea is the only vital organ not amenable in any particle fashion to transplantation. Attempts at bioengineering tracheas have been to date fraught with complications and delayed healing. Furthermore, cartilage has been believed to be non-renewable. We hypothesized that activated CD47 inhibited cell self-renewal and restoration of decellularized tracheal matrix scaffolds. Eight weeks post-procedure decellularized WT tracheas orthotopically transplanted into CD47-null mice displayed modest cell repopulation. In contrast WT scaffolds transplanted in the CD47−/− environment displayed dramatic cell repopulation and complete restoration of cartilage compared to transplants in WT animals (FIG. 26).

Figure 27:
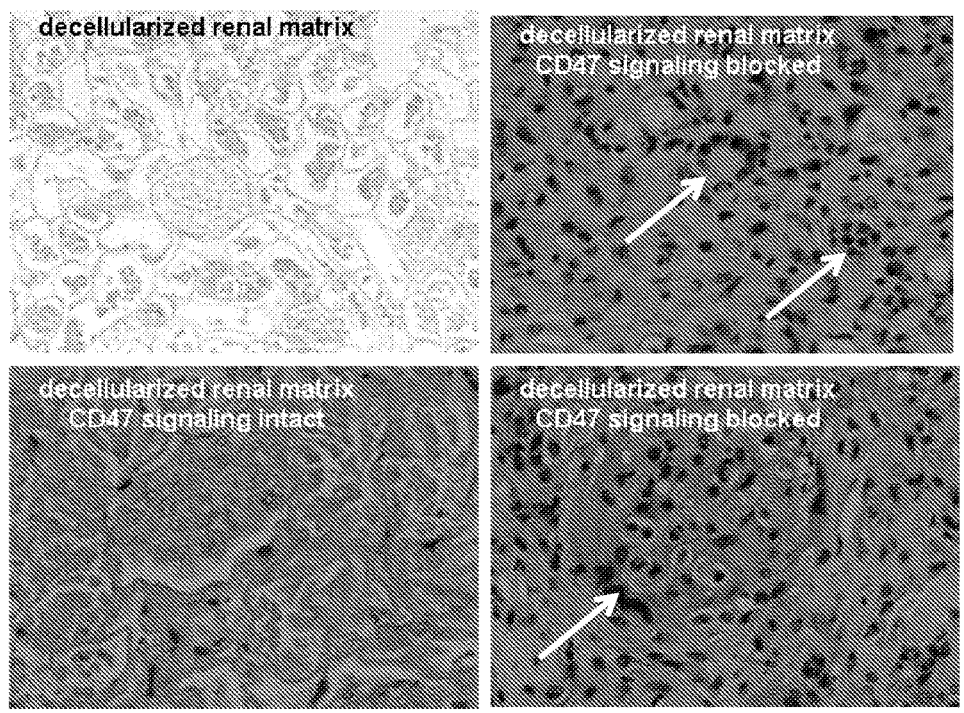
FIG. 27 is a series of digital images showing that eliminating CD47 signaling leads to nephro-genesis in decellularized matrix. Decellularized matrix in WT animals with intact CD47 signaling shows minimal restoration (left panels). The same matrix in animals with CD47 signaling blocked display complete restoration with tubular and glomerular like structures and functional vessels (containing red blood cells) (arrows; right panels).

Blockade of CD47 Signaling Results in Nephro-Genesis in Decellularized Matrix:

To further explore the implications of this in complex 3D organs we decellularized rat kidneys and implanted them in subcutaneous (ectopic) locations in mice. In some animals we blocked CD47 signaling. At 4 weeks following implantation the matrix was removed and tissue sections prepared and stained with H&E. As can been seen (FIG. 27), the matrix removed from animals with intact CD47 signaling showed minimal cellular repopulation. Conversely, matrix from animals with blocked CD47 signaling showed complete cellular restoration and recapitulation of normal appearing renal tubules and glomeruli and patent blood vessels containing red blood cells (RBCS) (arrows) (FIG. 27). These data demonstrate complete and rapid restoration without over-activity and no evidence of cellular disorganization. In addition, these results occurred with the matrix placed in an ectopic subcutaneous location, indicating that tissue engineering in vivo is a viable alternative with ease of application. Finally the restoration of a vasculature in the matrix clears a further hurdle to the application of decellularized scaffolds to organ and tissue engineering.

In view of the many possible embodiments to which the principles of the disclosure may be applied, it should be recognized that the illustrated embodiments are only examples and should not be taken as limiting the scope of the invention. Rather, the scope of the invention is defined by the claims. We therefore claim as our invention all that comes within the scope and spirit of these claims.

We claim:

1. A method for inducing multipotent or lineage-committed stem cells, comprising:
   obtaining primary endothelial cells from a mammal;
   transferring the primary endothelial cells into serum free media; and
   contacting the cultured primary endothelial cells with an agent that blocks CD47 signaling, thereby inducing multipotent or lineage-committed stem cells.

2. The method of claim 1, further comprising identifying and isolating a subset of multipotent or lineage committed stem cells that express stem cell marker genes comprising at least one of c-Myc, Sox2, Klf4, and Oct4.

3. The method of claim 1, wherein the induced multipotent stem cells form embryoid bodies.

4. The method of claim 1, wherein the agent that blocks CD47 signaling comprises an anti-CD47 antibody or a fragment thereof that retains CD-47 specific binding activity, a CD47-binding peptide, a CD47 antisense oligonucleotide, a CD47 morpholino, an anti-TSP1 antibody or fragment thereof that retains TSP1 specific binding activity, a TSP1-binding peptide, a TSP1 antisense oligonucleotide, or a TSP1 morpholino.

5. The method of claim 1, wherein the primary endothelial cells comprise human umbilical vein endothelial cells.

6. The method of claim 1, wherein the endothelial cells comprise at least one endothelial cell type selected from the group consisting of lung, human umbilical vein, cardiac valve, vascular, lymphatic, and microvascular endothelial cells.

7. A method for generating differentiated cells, comprising:
   obtaining primary endothelial cells from a mammal;
   culturing the primary endothelial cells;
   contacting the cultured primary endothelial cells with an agent that blocks CD47 signaling thereby inducing multipotent or lineage-committed stem cells;
   isolating from the contacted cells, multipotent or lineage-committed stem cells that express at least one of c-Myc, Sox2, Klf4, and Oct4; and,
   culturing the isolated multipotent or lineage-committed stem cells in cell differentiation medium to produce differentiated cells.

8. The method of claim 7, wherein the multipotent or lineage-committed stem cells form embryoid bodies.

9. The method of claim 7, wherein culturing the multipotent or lineage-committed stem cells in cell differentiation medium comprises culturing the multipotent or lineage-committed stem cells in neural cell differentiation medium, smooth muscle cell differentiation medium, hepatocyte cell differentiation medium, or mesenchymal cell differentiation medium.

10. The method of claim 7, wherein the differentiated cells comprise mesoderm-derived lineage cells comprising at least one of smooth muscle cells, endothelial cells, hematopoietic cells, and myeloid cells.

11. The method of claim 7, wherein the agent that blocks CD47 signaling comprises an anti-CD47 antibody or a fragment thereof that retains CD-47 specific binding activity, a CD47-binding peptide, a CD47 antisense oligonucleotide, a CD47 morpholino, an anti-TSP1 antibody or a fragment thereof that retains TSP1 specific binding activity, a TSP1-binding peptide, a TSP1 antisense oligonucleotide, or a TSP1 morpholino.

12. A method for inducing multipotent cells, comprising:
   obtaining endothelial cells from a mammal;
   transferring the endothelial cells into serum free media; and
   contacting the cultured endothelial cells with an agent that blocks CD47 signaling which is selected from the group consisting of an anti-CD47 antibody or a fragment thereof that retains CD-47 specific binding activity, a CD47-binding peptide, a CD47 antisense oligonucleotide, a CD47 morpholino, an anti-TSP1 antibody or a fragment thereof that retains TSP1 specific binding activity, a TSP1-binding peptide, a TSP1 antisense oligonucleotide, or a TSP1 morpholino,
   thereby inducing embryoid-like multipotent cells that express at least one of c-Myc, Sox2, Klf4, Oct4, and neuronal markers, hepatocyte markers and adipocyte markers, but do not form teratomas.

13. The method of claim 12, further comprising culturing the embryoid-like multipotent cells in a cell differentiation medium selected from neural cell differentiation medium, smooth muscle cell differentiation medium, hepatocyte cell differentiation medium, or mesenchymal cell differentiation medium.

14. The method of claim 12, wherein the endothelial cells comprise at least one endothelial cell type selected from the group consisting of lung, human umbilical vein, cardiac valve, vascular, lymphatic, and microvascular endothelial cells.

* * * * *

SEQUENCE LISTING

```
<160> NUMBER OF SEQ ID NOS: 38

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide 7N3

<400> SEQUENCE: 1

Phe Ile Arg Val Val Met Tyr Glu Gly Lys Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide 604

<400> SEQUENCE: 2

Phe Ile Arg Gly Gly Met Tyr Glu Gly Lys Lys
1               5                   10

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide primer - Nestin
      Forward

<400> SEQUENCE: 3
gtgcttaaga ccctggatcc a                                             21

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide primer - Nestin
      Reverse

<400> SEQUENCE: 4
gcacaactcc acagactgca ccca                                          24

<210> SEQ ID NO 5
<211> LENGTH: 24
<212> TYPE: DNA
<213> ORGANISM: Artificial Sequence
<220> FEATURE:
```

<223> OTHER INFORMATION: Synthetic oligonucleotide primer - Klf4 Forward

<400> SEQUENCE: 5
gctccgatga actgaccagg cact                                    24

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide primer - Klf4 Reverse

<400> SEQUENCE: 6
tgtgtaaggc aaggtggtcc gac                                     23

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide primer - Socs2
      Forward

<400> SEQUENCE: 7
gctctgtggt caagtccgag gcca                                    24

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer - Socs2
      Reverse

<400> SEQUENCE: 8
tgctgatcat gtcccggagg                                         20

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide primer - Oct4 Forward

<400> SEQUENCE: 9
ccaggctatg gaagccccca ct                                      22

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer - Oct4 Reverse

<400> SEQUENCE: 10
gaaaggcctc gccctcagga                                         20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer - Myc Forward

<400> SEQUENCE: 11
tcaaaaaagc caccgcctac a                                       21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer - Myc Reverse

<400> SEQUENCE: 12
cgaagctgtt cgagtttgtg                                           20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer - E2F Forward

<400> SEQUENCE: 13
tttggtctcg aggagggtga                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer - Myc Reverse

<400> SEQUENCE: 14
aatccagagg ggtcaggtcc                                           20

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide primer - p16INK4a
      Forward

<400> SEQUENCE: 15
ttcgaactgc gaggacccca ct                                        22

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer - p16INK4a
      Reverse

<400> SEQUENCE: 16
atcgcgcaca tccagccgag                                           20

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide primer - TRP53
      Forward

<400> SEQUENCE: 17
ctggagacag cagggctcac tcc                                       23

<210> SEQ ID NO 18
<211> LENGTH: 20

```
<212> TYPE: DNA
<213> ORGANISM: Artificial Sequence
<220> FEATURE:
<223> OTHER INFORMATION: Synthetic oligonucleotide primer - TPR53
      Reverse

<400> SEQUENCE: 18
tgagtcaggc cccactttct                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide primer - RB Forward

<400> SEQUENCE: 19
agaaggtctg ccaacaccca                                              20

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide primer - RB Reverse

<400> SEQUENCE: 20
ctggaacttt tcagatgtcc ca                                           22

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide primer - HPRT1
      Forward

<400> SEQUENCE: 21
gttaagcagt acagccccaa a                                            21

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide primer - HPRT1
      Reverse

<400> SEQUENCE: 22
agggcatatc caacaacaaa ctt                                          23

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide primer - murine B2M
      Forward

<400> SEQUENCE: 23
tgtccttcag caaggactgg                                              20

<210> SEQ ID NO 24
<211> LENGTH: 23
<212> TYPE: DNA
<213> ORGANISM: Artificial Sequence
<220> FEATURE:
```

```
<223> OTHER INFORMATION: Synthetic oligonucleotide primer - murine B2M
      Reverse

<400> SEQUENCE: 24
ggcatgctta actctgcagg ggt                                              23

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide primer - human B2M
      Forward

<400> SEQUENCE: 25
tcctgaattg ctatgtgtct gggt                                             24

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide primer - human B2M
      Reverse

<400> SEQUENCE: 26
gatagaaaga ccagtccttg tt                                               22

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide primer - human Myc
      Forward

<400> SEQUENCE: 27
cgtccaagca gaggagcaaa agct                                             24

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide primer - human Myc
      Reverse

<400> SEQUENCE: 28
cgcacaagag ttccgtagct g                                                21

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide primer - FBP Forward

<400> SEQUENCE: 29
ggagatcagc agaatccagc ccca                                             24

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide primer - FBP Reverse
```

<400> SEQUENCE: 30
cagtcggagc aggaactgcc t                                                   21

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide primer - human HPRT1
      Forward

<400> SEQUENCE: 31
attgtaatga ccagtcaaca g                                                   21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide primer - human HPRT1
      Reverse

<400> SEQUENCE: 32
gcattgtttt gccagtgtca a                                                   21

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide primer - TAF9 Forward

<400> SEQUENCE: 33
actcccacac taggcacac                                                      19

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide primer - TAF9 Reverse

<400> SEQUENCE: 34
tgagaagtag gcatctgtac tgt                                                 23

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide - CD47 morpholino

<400> SEQUENCE: 35
cgtcacaggc aggacccact gccca                                               25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide - control morpholino

<400> SEQUENCE: 36
cgtgacagcc acgaccgact gcgca                                               25

```
<210> SEQ ID NO 37
<211> LENGTH: 8
<212> TYPE: PRT
<213> ORGANISM: Artificial Sequence
<220> FEATURE:
<223> OTHER INFORMATION: Synthetic peptide - 4N1

<400> SEQUENCE: 37

Arg Phe Tyr Val Val Met Trp Lys
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide - 761

<400> SEQUENCE: 38

Arg Phe Tyr Gly Gly Met Trp Lys
1               5
```